United States Patent
Dazai et al.

(10) Patent No.: US 8,227,170 B2
(45) Date of Patent: Jul. 24, 2012

(54) RESIST COMPOSITION, METHOD OF FORMING RESIST PATTERN, POLYMERIC COMPOUND, AND COMPOUND

(75) Inventors: Takahiro Dazai, Kawasaki (JP); Daiju Shiono, Kawasaki (JP); Tomoyuki Hirano, Kawasaki (JP); Tasuku Matsumiya, Kawasaki (JP); Daichi Takaki, Kawasaki (JP); Takayoshi Mori, Kawasaki (JP); Junichi Tsuchiya, Kawasaki (JP)

(73) Assignee: Tokyo Ohka Kogyo Co., Ltd., Kawasaki-shi (JP)

(*) Notice: Subject to any disclaimer, the term of this patent is extended or adjusted under 35 U.S.C. 154(b) by 314 days.

(21) Appl. No.: 12/685,579

(22) Filed: Jan. 11, 2010

(65) Prior Publication Data
US 2010/0178609 A1 Jul. 15, 2010

(30) Foreign Application Priority Data
Jan. 14, 2009 (JP) .................. 2009-006006

(51) Int. Cl.
| G03F 7/039 | (2006.01) |
| G03F 7/20 | (2006.01) |
| G03F 7/30 | (2006.01) |
| C08F 28/06 | (2006.01) |
| C07D 327/04 | (2006.01) |

(52) U.S. Cl. ............ 430/270.1; 430/325; 430/326; 430/910; 526/257; 549/31; 549/40

(58) Field of Classification Search .............. None
See application file for complete search history.

(56) References Cited

U.S. PATENT DOCUMENTS

| 4,458,001 A | 7/1984 | Taylor |
| 5,945,517 A | 8/1999 | Nitta et al. |
| 6,153,733 A | 11/2000 | Yukawa et al. |
| 6,388,101 B1 | 5/2002 | Hada et al. |
| 7,074,543 B2 | 7/2006 | Iwai et al. |
| 7,078,562 B2 | 7/2006 | Furukawa et al. |
| 7,186,495 B2 | 3/2007 | Maeda et al. |
| 2002/0012874 A1 | 1/2002 | Namba |
| 2009/0226842 A1 | 9/2009 | Shimizu et al. |
| 2010/0062364 A1 | 3/2010 | Dazai et al. |
| 2010/0086873 A1 | 4/2010 | Seshimo et al. |
| 2010/0136478 A1* | 6/2010 | Kawaue et al. ............ 430/270.1 |
| 2010/0136480 A1 | 6/2010 | Motoike et al. |
| 2010/0183981 A1 | 7/2010 | Matsumiya et al. |
| 2010/0196821 A1 | 8/2010 | Dazai et al. |
| 2010/0209848 A1 | 8/2010 | Dazai et al. |
| 2010/0233623 A1 | 9/2010 | Kurosawa et al. |
| 2010/0233624 A1 | 9/2010 | Kakinoya et al. |
| 2010/0233625 A1 | 9/2010 | Hirano et al. |
| 2010/0233626 A1 | 9/2010 | Shimizu et al. |
| 2011/0236824 A1 | 9/2011 | Hirano et al. |

FOREIGN PATENT DOCUMENTS

| JP | H09-208554 | 8/1997 |
| JP | H10-207069 | 8/1998 |
| JP | H11-035551 | 2/1999 |
| JP | H11-035552 | 2/1999 |
| JP | H11-035573 | 2/1999 |
| JP | H11-322707 | 11/1999 |
| JP | 2000-26446 | 1/2000 |
| JP | 2003-241385 | 8/2003 |
| JP | 2005-037888 | 2/2005 |
| JP | 2005-336452 | 12/2005 |
| JP | A-2006-016379 | 1/2006 |
| JP | 2006-259582 | 9/2006 |
| JP | A-2007-031355 | 2/2007 |
| WO | WO 2004/074242 | 9/2004 |

OTHER PUBLICATIONS

Office Action in U.S. Appl. No. 12/461,687 mailed Sep. 12, 2011.
Notice of Allowance issued in U.S. Appl. No. 12/461,687 on Jan. 25, 2012.
Office Action issued in U.S. Appl. No. 12/717,870 on Sep. 14, 2011.
Office Action issued in U.S. Appl. No. 12/717,870 on Jan. 26, 2012.

* cited by examiner

*Primary Examiner* — Sin J. Lee
(74) *Attorney, Agent, or Firm* — Knobbe Martens Olson & Bear LLP

(57) ABSTRACT

A resist composition including a base component (A) which exhibits changed solubility in an alkali developing solution under action of an acid, and an acid generator component (B), wherein the base component (A) includes a polymeric compound (A0) containing a structural unit (a0) represented by the general formula (a0-1) shown below:

[Chemical Formula 1]

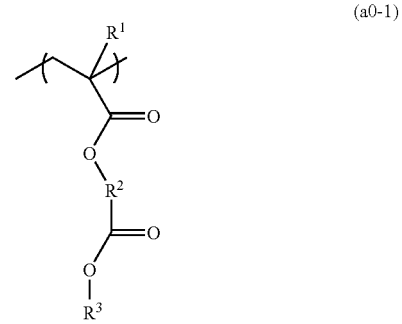

(a0-1)

(wherein, $R^1$ represents a hydrogen atom, an alkyl group or a halogenated alkyl group; $R^2$ represents a bivalent linking group containing at least one kind of polar groups selected from the group consisting of —O—, —C(=O)—, —C(=O)—O—, a carbonate linkage (—O—C(=O)—O—), —S—, —S(=O)$_2$—, —S(=O)$_2$—O—, —NH—, —NR$^{04}$— (wherein, $R^{04}$ represents an alkyl group or an acyl group), and —NH—C(=O)—; and $R^3$ represents a cyclic group containing a sulfonyl group within the ring skeleton).

20 Claims, No Drawings

RESIST COMPOSITION, METHOD OF FORMING RESIST PATTERN, POLYMERIC COMPOUND, AND COMPOUND

TECHNICAL FIELD

The present invention relates to a novel polymeric compound which can be used as a base component of a resist composition, a compound which provides a structural unit constituting the polymeric compound, a resist composition including the polymeric compound, and a method of forming a resist pattern using the resist composition.

The application claims priority from Japanese Patent Application No. 2009-006006 filed on Jan. 14, 2009, the disclosure of which is incorporated by reference herein.

BACKGROUND ART

Lithography techniques include processes in which, for example, a resist film formed from a resist material is formed on top of a substrate, the resist film is selectively exposed with irradiation such as light, an electron beam or the like through a mask in which a predetermined pattern has been formed, and then a developing treatment is conducted, thereby forming a resist pattern of the prescribed shape in the resist film.

Resist materials in which the exposed portions change to become soluble in a developing solution are termed positive materials, whereas resist materials in which the exposed portions change to become insoluble in a developing solution are termed negative materials.

In recent years, in the production of semiconductor elements and liquid crystal display elements, advances in lithography techniques have led to rapid progress in the field of miniaturization.

Typically, these miniaturization techniques involve shortening the wavelength of the exposure light source. Conventionally, ultraviolet radiation typified by g-line and i-line radiation has been used; however, nowadays, KrF excimer lasers and ArF excimer lasers are starting to be introduced in mass production of semiconductor elements. Furthermore, research is also being conducted into lithography techniques that use $F_2$ excimer lasers, electron beams (EB), extreme ultraviolet radiation (EUV), and X-rays.

Resist materials are required to have lithography properties such as sensitivity to the aforementioned light source and enough resolution to reproduce patterns with very fine dimensions.

As resist materials which fulfill the aforementioned requirements, there is used a chemically-amplified resist containing a base component that displays changed solubility in an alkali developing solution under action of an acid, and an acid generator that generates an acid upon exposure.

For example, as the chemically-amplified positive resist composition, a resist composition containing a resin component (a base resin) that exhibits increased solubility in an alkali developing solution under action of an acid and an acid generator component is commonly used. If the resist film formed using the resist composition is selectively exposed during formation of a resist pattern, then within the exposed portions, an acid is generated from the acid generator, and the action of this acid causes an increase in the solubility of the resin component in an alkali developing solution, making the exposed portions soluble in the alkali developing solution.

Resins (acrylic resins) that contain structural units derived from (meth)acrylate esters within the main chain thereof are now widely used as base resins for resists that use ArF excimer laser lithography, as they exhibit excellent transparency in the vicinity of 193 nm (for example, see Patent Document 1).

Here, the term "(meth)acrylic acid" is a generic term that includes either or both of the acrylic acid having a hydrogen atom bonded to the α-position and the methacrylic acid having a methyl group bonded to the α-position.

The term "(meth)acrylate ester" is a generic term that includes either or both of an acrylate ester having a hydrogen atom bonded to the α-position and a methacrylate ester having a methyl group bonded to the α-position. The term "(meth)acrylate" is a generic term that includes either or both of an acrylate having a hydrogen atom bonded to the α-position and a methacrylate having a methyl group bonded to the α-position.

Also, as base resins for chemically amplified resists, base resins containing a plurality of structural units are now used in order to improve lithography properties and the like.

For example, in case of using a positive-type resist, a base resin is typically used which includes a structural unit having an acid dissociable, dissolution inhibiting group which dissociates under action of an acid generated from an acid generator, and further includes a structural unit having a polar group such as a hydroxyl group, a structural unit having a lactone structure, or the like.

Of these structural units, the structural unit having a lactone structure is generally considered to contribute to the improvement of the adhesion of the resist film with a substrate, the improvement of compatibility with an alkali developing solution, and the improvement of lithography properties (For example, see Patent Documents 2 and 3).

DOCUMENTS OF RELATED ART

Patent Documents

[Patent Document 1] Japanese Unexamined Patent Application, First Publication No. 2003-241385.
[Patent Document 2] Japanese Unexamined Patent Application, First Publication No. Hei10-207069.
[Patent Document 3] Japanese Unexamined Patent Application, First Publication No. 2000-26446.

SUMMARY OF THE INVENTION

Problems to be Solved by the Invention

The demand for a novel material which can be used for lithography has been increased, since it is expected that lithography technology will further make progress and the field of application will be broadened.

For example, as miniaturization of the resist pattern has progressed more and more, the dimension of the resist pattern becomes smaller, and thus it is demanded to further improve resolution, regarding conventionally-used chemically amplified resist compositions.

The present invention takes the above circumstances into consideration, with an object of providing a novel polymeric compound which exhibits excellent resolution and can be used as a base component of a resist composition, a compound useful as a monomer of the polymeric compound, a resist composition including the polymeric compound, and a method of forming a resist pattern using the resist composition.

Means for Solving the Problems

To achieve the above object, the present invention employs the following constitutions.

Specifically, a first aspect of the present invention is a resist composition including a base component (A) which exhibits changed solubility in an alkali developing solution under action of an acid, and an acid generator component (B) which generates an acid upon exposure, wherein the base component (A) includes a polymeric compound (A0) which contains a structural unit (a0) represented by the general formula (a0-1) shown below.

[Chemical Formula 1]

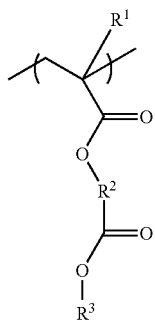

(a0-1)

(In the formula (a0-1), $R^1$ represents a hydrogen atom, a lower alkyl group of 1 to 5 carbon atoms, or a halogenated lower alkyl group of 1 to 5 carbon atoms; $R^2$ represents a bivalent linking group containing at least one kind of polar groups selected from the group consisting of —O—, —C(=O)—, —C(=O)—O—, a carbonate linkage (—O—C(=O)—O—), —S—, —S(=O)$_2$—, —S(=O)$_2$—O—, NH—, NR$^{04}$— (wherein, R$^{04}$ represents an alkyl group or an acyl group), and —NH—C(=O)—; and $R^3$ represents a cyclic group containing a sulfonyl group within the ring skeleton.)

A second aspect of the present invention is a method of forming a resist pattern, which includes: forming a resist film on a substrate using the resist composition of the first aspect of the present invention; exposing the resist film; and developing the resist film with an alkali to form a resist pattern.

A third aspect of the present invention is a polymeric compound containing a structural unit (a0) represented by the general formula (a0-1) shown below.

[Chemical Formula 2]

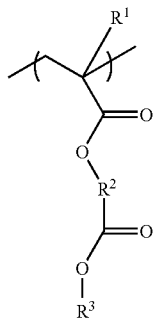

(a0-1)

(In the formula (a0-1), $R^1$ represents a hydrogen atom, a lower alkyl group of 1 to 5 carbon atoms, or a halogenated lower alkyl group of 1 to 5 carbon atoms; $R^2$ represents a bivalent linking group containing at least one kind of polar groups selected from the group consisting of —O—, —C(=O)—, —C(=O)—O—, a carbonate linkage (—O—C(=O)—O—), —S—, —S(=O)$_2$—, —S(=O)$_2$—O—, NH—, NR$^{04}$— (wherein, R$^{04}$ represents an alkyl group or an acyl group), and —NH—C(=O)—; and $R^3$ represents a cyclic group containing a sulfonyl group within the ring skeleton.)

A fourth aspect of the present invention is a compound represented by the general formula (a0″-1) shown below.

[Chemical Formula 3]

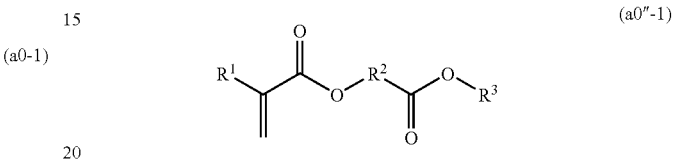

(a0″-1)

(In the formula (a0″-1), $R^1$ represents a hydrogen atom, a lower alkyl group of 1 to 5 carbon atoms, or a halogenated lower alkyl group of 1 to 5 carbon atoms; $R^2$ represents a bivalent linking group containing at least one kind of polar groups selected from the group consisting of —O—, —C(=O)—, —C(=O)—O—, a carbonate linkage (—O—C(=O)—O—), —S—, —S(=O)$_2$—O—, —NH—, —NR$^{04}$— (wherein, R$^{04}$ represents an alkyl group or an acyl group), and —NH—C(=O)—; and $R^3$ represents a cyclic group containing a sulfonyl group within the ring skeleton.)

In the present specification and claims, the term "aliphatic" is a relative concept used in relation to the term "aromatic", and defined as a group, a compound or the like that has no aromaticity.

The term "alkyl group" is a concept containing a linear, branched and cyclic monovalent saturated hydrocarbon group, unless another definition is particularly provided.

The term "alkylene group" is a concept containing a linear, branched, and cyclic bivalent saturated hydrocarbon group, unless another specific definition is provided. The same definition can also be applied to an alkylene group included in an alkoxy group.

The term "halogenated alkyl group" means a group in which a part or all of hydrogen atoms in an alkyl group are substituted with halogen atoms, and examples of the halogen atom include a fluorine atom, a chlorine atom, a bromine atom, and an iodine atom.

The term "fluorinated alkyl group" or "fluorinated alkylene group" means a group in which a part or all of hydrogen atoms in the alkyl group or alkylene group are substituted with fluorine atoms.

The terms "lower alkyl group" and "halogenated lower alkyl group" mean "an alkyl group of 1 to 5 carbon atoms" and "a halogenated alkyl group of 1 to 5 carbon atoms", respectively.

The term "structural unit" means a monomer unit that contributes to the formation of a polymeric compound (resin, polymer, copolymer).

The term "exposure" is used as a general concept involving irradiation with any form of radiation.

Effects of the Invention

According to the present invention, there can be provided a novel polymeric compound which excels in resolution and can be used as a base component of a resist composition, a compound useful as a monomer of the polymeric compound, a resist composition including the polymeric compound, and a method of forming a resist pattern using the resist composition.

BEST MODE FOR CARRYING OUT THE INVENTION

Resist Composition

The resist composition of the first aspect of the present invention includes a base component (A) which exhibits changed solubility in an alkali developing solution under action of an acid (hereinafter, referred to as "component (A)"), and an acid generator component (B) which generates an acid upon exposure (hereinafter, referred to as "component (B)").

In a resist film formed by using the resist composition, an acid is generated from the component (B) when a selective exposure is conducted in the formation of the resist pattern, and the acid thus generated from the component (B) causes the solubility of the component (A) in an alkali developing solution to be changed. As a result, whereas the exposed portions of the resist film exhibit changed solubility in an alkali developing solution, the unexposed portions do not exhibit changed solubility in an alkali developing solution. Therefore, if the resist composition is a positive resist composition, the exposed portions are dissolved to be removed by a developing treatment with alkali, thereby forming a resist pattern. On the other hand, if the resist composition is a negative resist composition, the unexposed portions are dissolved to be removed by a developing treatment with alkali, thereby forming a resist pattern.

The resist composition of the present invention may be a negative resist composition or a positive resist composition.

Also, the resist composition of the present invention preferably further includes a nitrogen-containing organic compound component (D) (hereinafter, referred to as "component (D)"), in addition to the components (A) and (B).

<Component (A)>

In the resist composition of the present invention, the component (A) includes the polymer compound (A0) containing the structural unit (a0) represented by the general formula (a0-1).

As the component (A), the polymeric compound (A0) may be used alone, or an organic compound which has conventionally been used as a base component for a chemically amplified resist may be used together with the polymeric compound (A0).

Here, the term "base component" means an organic compound which has a film-forming capability, and the molecular weight thereof is preferably 500 or more. When the molecular weight of the organic compound is 500 or more, the film-forming capability can be improved, and a nano-level resist pattern can easily be formed.

The organic compounds whose molecular weight is 500 or more can be classified broadly into a low molecular weight organic compound whose molecular weight is within a range from 500 to less than 2,000 (hereinafter, referred to as "low molecular weight compound"), and a resin (polymeric material) whose molecular weight is 2,000 or more. As the low molecular weight compound, a non-polymer is typically used. In the case of using a resin (polymer, copolymer), the polystyrene equivalent molecular weight determined by gel permeation chromatography (GPC) is used as "molecular weight". Hereinafter, in the case of merely using the term "resin", it means a resin with a molecular weight of 2,000 or more.

As the organic compound above, a resin component which exhibits changed solubility in an alkali developing solution under action of an acid can be used, and also a low molecular weight compound component which exhibits changed solubility in an alkali developing solution under action of an acid can be used.

If the resist composition of the present invention is a negative resist composition, a base component which is soluble in an alkali developing solution is used as the component (A), and a cross-linking agent component is further blended in the negative resist composition.

In the negative resist composition, when acid is generated from the component (B) upon exposure, the action of this acid causes cross-linking reaction between the base component and the cross-linking agent component, thereby changing the negative resist composition to a poorly-soluble state in an alkali developing solution. Therefore, in the formation of a resist pattern, when a resist film obtained by applying the negative resist composition on a substrate is subjected to selective exposure, the exposed area becomes poorly-soluble in an alkali developing solution, while the unexposed area remains soluble in the alkali developing solution, and hence a resist pattern can be formed by a developing treatment with an alkali.

A resin (hereinafter referred to as "alkali-soluble resin") which is soluble in an alkali developing solution is typically used as the component (A) of the negative resist composition.

As the alkali-soluble resin, it is preferable to use a resin having a structural unit derived from at least one kind selected from the group consisting of α-(hydroxyalkyl)acrylic acids and lower alkyl esters of α-(hydroxyalkyl)acrylic acids; or a resin having a fluorinated alcohol disclosed in Japanese Unexamined Patent Application, First Publication No. 2005-336452 or Japanese Unexamined Patent Application, First Publication No. 2006-259582, because it enables formation of a satisfactory resist pattern with minimal swelling.

In the resist composition of the present invention, the polymeric compound (A0) may be used as the alkali-soluble resin, a resin component (base resin) typically used as a base component for a chemically amplified resist may be used as the alkali-soluble resin, or both of them may be used together as the alkali-soluble resin.

Here, the term "α-(hydroxyalkyl)acrylic acid" means one or both of the acrylic acid in which a hydrogen atom is bonded to the carbon atom at the α-position to which the carboxyl group is bonded, and an α-hydroxyalkylacrylic acid in which a hydroxyalkyl group (preferably a hydroxyalkyl group of 1 to 5 carbon atoms) is bonded to the carbon atom at the α-position.

As the cross-linking agent component, usually, an amino-based cross-linking agent such as a glycoluril that contains a methylol group or an alkoxymethyl group is preferable, because it enables a satisfactory resist pattern with minimal swelling to be formed. The blend quantity of the cross-linking agent component is preferably within a range from 1 to 50 parts by weight, relative to 100 parts by weight of the alkali-soluble resin.

If the resist composition of the present invention is a positive resist composition, a base component (hereinafter, referred to as "component (A')") which exhibits increased solubility in an alkali developing solution under action of an acid is used as the component (A).

The component (A') is poorly-soluble in an alkali developing solution before exposure, and when an acid is generated from the component (B) upon exposure, the action of the acid causes an increase in the solubility of the component (A') in an alkali developing solution. Therefore, in the formation of a resist pattern, when a resist film obtained by applying the positive resist composition on the substrate is subjected to selective exposure, the exposed area becomes soluble in an alkali developing solution, while the unexposed area remains poorly-soluble in alkali developing solution, and hence a resist pattern can be formed by a developing treatment with an alkali.

In the resist composition of the present invention, the component (A) is preferably a base component (component (A')) which exhibits increased solubility in an alkali developing solution under action of an acid. That is, the resist composition of the present invention is preferably a positive resist composition.

The component (A') may be a resin component (A1) (hereinafter, sometimes referred to as "component (A1)") which exhibits increased solubility in an alkali developing solution under action of an acid, a low molecular weight compound component (A2) (hereinafter, sometimes referred to as "component (A2)") which exhibits increased solubility in an alkali developing solution under action of an acid, or a mixture of them.

[Component (A1)]

In the resist composition of the present invention, the polymeric compound (A0) may be used as the component (A1), a resin component (base resin) typically used as a base component for a chemically-amplified resist may be used as the component (A1), or both of them may be used as the component (A1).

In the present invention, the component (A1) preferably contains a structural unit derived from an acrylate ester.

Here, the term "structural unit derived from an acrylate ester" in the present specification and claims means a structural unit formed by cleavage of the ethylenic double bond of an acrylate ester.

The term "acrylate ester" is a concept containing an acrylate ester in which a hydrogen atom is bonded to a carbon atom at the α-position, and an α-substituted acrylate ester in which a substituent (an atom or group other than a hydrogen atom) is bonded to the carbon atom at the α-position. Examples of the substituent bonded to the carbon atom at the α-position include an alkyl group of 1 to 5 carbon atoms, a halogenated alkyl group of 1 to 5 carbon atoms, and a hydroxyalkyl group of 1 to 5 carbon atoms. Here, the carbon atom at the α-position of an acrylate ester means the carbon atom to which the carbonyl group is bonded, unless another definition is provided.

In the acrylate ester, specific examples of the lower alkyl group for the substituent at the α-position include linear or branched lower alkyl groups such as a methyl group, an ethyl group, a propyl group, an isopropyl group, an n-butyl group, an isobutyl group, a tert-butyl group, a pentyl group, an isopentyl group, and a neopentyl group.

Specific examples of the halogenated lower alkyl group for the substituent include groups in which a part of or all of the hydrogen atoms of the "lower alkyl group for the substituent at the α-position" described above are substituted with halogen atoms. Examples of the halogen atom include a fluorine atom, a chlorine atom, an iodine atom, and a bromine atom. Of these, a fluorine atom is preferable.

In the present invention, the group which is bonded to the α-position of an acrylate ester is preferably a hydrogen atom, a lower alkyl group or a halogenated lower alkyl group; more preferably a hydrogen atom, a lower alkyl group or a fluorinated lower alkyl group; and still more preferably a hydrogen atom or a methyl group, in terms of industrial availability.

Of these, in the resist composition of the present invention, the component (A1) particularly preferably contains a polymeric compound (A0).

(Polymeric Compound (A0))

The polymeric compound (A0) contains a structural unit (a0) represented by the general formula (a0-1) shown below.

Also, the polymeric compound (A0) preferably contains the above structural unit (a0) and a structural unit (a1) derived from an acrylate ester which has an acid dissociable, dissolution inhibiting group.

Also, the polymeric compound (A0) preferably further includes a structural unit (a3) derived from an acrylate ester which has a polar group-containing aliphatic hydrocarbon group, in addition to the structural units (a0) and (a1).

[Chemical Formula 4]

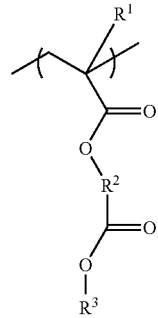

(a0-1)

(In the formula (a0-1), $R^1$ represents a hydrogen atom, a lower alkyl group of 1 to 5 carbon atoms, or a halogenated lower alkyl group of 1 to 5 carbon atoms; $R^2$ represents a bivalent linking group containing at least one kind of polar groups selected from the group consisting of —O—, —C(=O)—, —C(=O)—O—, a carbonate linkage (—O—C(=O)—O—), —S—, —S(=O)$_2$—, —S(=O)$_2$—O—, —NH—, —NR$^{04}$— (wherein, $R^{04}$ represents an alkyl group or an acyl group), and —NH—C(=O)—; and $R^3$ represents a cyclic group containing a sulfonyl group within the ring skeleton.)

Structural Unit (a0)

In the above formula (a0-1), $R^1$ represents a hydrogen atom, a lower alkyl group of 1 to 5 carbon atoms, or a halogenated lower alkyl group of 1 to 5 carbon atoms.

The lower alkyl group for $R^1$ is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an isopentyl group and a neopentyl group.

The halogenated lower alkyl group for $R^1$ is a group in which a part or all of the hydrogen atoms in the above lower alkyl group are substituted with halogen atoms. Examples of the halogen atom include a fluorine atom, a chlorine atom, an iodine atom, and a bromine atom. Of these, a fluorine atom is preferable.

$R^1$ is preferably a hydrogen atom, a lower alkyl group, or a fluorinated lower alkyl group, and most preferably a hydrogen atom or a methyl group in terms of industrial availability.

In the above formula (a0-1), $R^2$ represents a bivalent linking group containing at least one kind of polar groups selected from the group consisting of —O—, —C(=O)—, —C(=O)—O—, a carbonate linkage (—O—C(=O)—

O—), —S—, —S(=O)₂—, —S(=O)₂—O—, —NH—, —NR$^{04}$— (wherein, R$^{04}$ represents an alkyl group or an acyl group), and —NH—C(=O)—.

If R² is —NR$^{04}$— (wherein, R$^{04}$ represents an alkyl group or an acyl group), R$^{04}$ preferably has 1 to 10 carbon atoms, more preferably 1 to 8 carbon atoms, and still more preferably 1 to 5 carbon atoms.

Examples of R² include the above polar groups and combined groups of the above polar groups with bivalent hydrocarbon groups.

Examples of the bivalent hydrocarbon group include a hydrocarbon group which may contain a substituent. Of these, a linear or branched aliphatic hydrocarbon group is preferable.

(Hydrocarbon Group which May Contain a Substituent)

The expression that a hydrocarbon group "contains a substituent group" means that a part or all of the hydrogen atoms in the hydrocarbon group are substituted with groups or atoms other than hydrogen atoms.

The hydrocarbon group may be an aliphatic hydrocarbon group, or may be an aromatic hydrocarbon group. The aliphatic hydrocarbon group means a hydrocarbon group which contains no aromaticity.

The aliphatic hydrocarbon group may be saturated or unsaturated, and is preferably saturated.

Specific examples of the aliphatic hydrocarbon group include a linear or branched aliphatic hydrocarbon group, and an aliphatic hydrocarbon group containing a ring within the structure.

The linear or branched aliphatic hydrocarbon group preferably has 1 to 10 carbon atoms, more preferably 1 to 8 carbon atoms, still more preferably 1 to 5 carbon atoms, and most preferably 1 to 2 carbon atoms.

As the linear aliphatic hydrocarbon group, a linear alkylene group is preferable, and specific examples thereof include a methylene group [—CH₂—], an ethylene group [—(CH₂)₂—], a trimethylene group [—(CH₂)₃—], a tetramethylene group [—(CH₂)₄—], and a pentamethylene group [—(CH₂)₅—].

The branched aliphatic hydrocarbon group is preferably a branched alkylene group, and specific examples thereof include alkylalkylene groups such as alkylmethylene groups (for example, —CH(CH₃)—, —CH(CH₂CH₃)—, —C(CH₃)₂—, —C(CH₃)(CH₂CH₃)—, —C(CH₃)(CH₂CH₂CH₃)—, or —C(CH₂CH₃)₂—); alkylethylene groups (for example, —CH(CH₃)CH₂—, —CH(CH₃)CH(CH₃)—, —C(CH₃)₂CH₂—, —CH(CH₂CH₃)CH₂—, or —CH(CH₂CH₃)₂—CH₂—); alkyltrimethylene groups (for example, —CH(CH₃)CH₂CH₂— or —CH₂CH(CH₃)CH₂—); and alkyltetramethylene groups (for example, —CH(CH₃)CH₂CH₂CH₂— or —CH₂CH(CH₃)CH₂CH₂—). Of these, alkylmethylene groups are preferable. The alkyl group in the alkylalkylene group is preferably a linear alkyl group of 1 to 5 carbon atoms, more preferably a linear alkyl group of 1 to 3 carbon atoms, and most preferably a methyl group.

The chain-like (linear or branched) aliphatic hydrocarbon group may or may not contain a substituent. Examples of the substituent include a fluorine atom, a fluorinated lower alkyl group of 1 to 5 carbon atoms, and an oxygen atom (=O).

Examples of the aliphatic hydrocarbon group containing a ring within the structure include a cyclic aliphatic hydrocarbon group (a group in which two hydrogen atoms have been removed from an aliphatic hydrocarbon ring); and a group in which the above cyclic aliphatic hydrocarbon group is bonded to the terminal of the aforementioned chain-like (linear or branched) aliphatic hydrocarbon group or is present within the aforementioned chain-like aliphatic hydrocarbon group.

The cyclic aliphatic hydrocarbon group preferably has 3 to 20 carbon atoms, and more preferably 3 to 12 carbon atoms.

The cyclic aliphatic hydrocarbon group may be a polycyclic group or may be a monocyclic group.

The monocyclic group is preferably a group in which two hydrogen atoms have been removed from a monocycloalkane of 3 to 6 carbon atoms, and examples of the monocycloalkane include cyclopentane and cyclohexane.

The polycyclic group is preferably a group in which two hydrogen atoms have been removed from a polycycloalkane of 7 to 12 carbon atoms, and examples of the polycycloalkane include adamantane, norbornane, isobornane, tricyclodecane, and tetracyclododecane.

The cyclic aliphatic hydrocarbon group may or may not contain a substituent.

Examples of the substituent include a lower alkyl group of 1 to 5 carbon atoms, a fluorine atom, a fluorinated lower alkyl group of 1 to 5 carbon atoms, and an oxygen atom (=O).

Examples of the aromatic hydrocarbon group include bivalent aromatic hydrocarbon groups in which one hydrogen atom has been further removed from an aromatic hydrocarbon nucleus of a monovalent aromatic hydrocarbon group such as a phenyl group, a biphenyl group, a fluorenyl group, a naphthyl group, an anthryl group or a phenanthryl group; aromatic hydrocarbon groups in which a part of the carbon atoms constituting the ring of the above bivalent aromatic hydrocarbon group are substituted with hetero atoms such as an oxygen atom, a sulfur atom, and a nitrogen atom; aromatic hydrocarbon groups in which one hydrogen atom has been further removed from an aromatic hydrocarbon nucleus of an arylalkyl group such as a benzyl group, a phenethyl group, a 1-naphthylmethyl group, a 2-naphthylmethyl group, a 1-naphthylethyl group, or a 2-naphthylethyl group.

The aromatic hydrocarbon group may or may not contain a substituent. Examples of the substituent include a lower alkyl group of 1 to 5 carbon atoms, a fluorine atom, a fluorinated lower alkyl group of 1 to 5 carbon atoms, and an oxygen atom (=O).

R² may or may not contain an acid dissociable portion within the structure.

The term "acid dissociable portion" means a portion within the structure of R² which dissociates under action of an acid generated upon exposure. When R² contains an acid dissociable portion, it is preferable to contain an acid dissociable portion which has a tertiary carbon atom.

Of these, suitable examples of R² include —O—, —C(=O)—, —C(=O)—O—, —O—C(=O)—O—, —NH—C(=O)—, —NR$^{04}$— (wherein R$^{04}$ represents an alkyl group or an acyl group). —S—, —S(=O)₂—, —S(=O)₂—O—, a group represented by the formula: -A-O—B—, and a group represented by the formula: -[A-C(=O)—O]$_q$—B—, and R² is particularly preferably a group represented by the formula: -[A-C(=O)—O]$_q$—B—.

Here, A and B each independently represents a bivalent hydrocarbon group which may contain a substituent; and q represents an integer of 0 to 3.

In -A-O—B— or -[A-C(=O)—O]$_q$—B—, A and B each independently represents a bivalent hydrocarbon group which may contain a substituent.

Examples of the bivalent hydrocarbon group which may contain a substituent for A and B include the same groups as those described above as "(hydrocarbon group which may contain a substituent)".

A is preferably a linear aliphatic hydrocarbon group, more preferably a linear alkylene group, still more preferably a linear alkylene group of 1 to 5 carbon atoms, and particularly preferably a methylene group or an ethylene group.

B is preferably a linear or branched aliphatic hydrocarbon group, and more preferably a methylene group, an ethylene group or an alkylmethylene group.

Also, in a group represented by the formula -[A-C(=O)—O—]$_q$—B—, q represents an integer of 0 to 3, more preferably an integer of 0 to 2, still more preferably 0 or 1, and most preferably 1.

In the above formula (a0-1), $R^3$ represents a cyclic group containing a sulfonyl group within the ring skeleton (ring structure).

The cyclic group for $R^3$ refers to a cyclic group containing a ring which has —$SO_2$— within the ring skeleton, and this ring is counted as the first ring. A cyclic group in which the only ring structure is this ring is referred to as a monocyclic group, and a cyclic group containing other ring structures is referred to as polycyclic group regardless of the structure of the other rings. The cyclic group for $R^3$ may be a monocyclic group, or may be a polycyclic group.

Of these, $R^3$ is particularly preferably a cyclic group containing —O—$SO_2$— within the ring skeleton, that is, a sultone ring.

The cyclic group for $R^3$ is preferably 3 to 30 carbon atoms, more preferably 4 to 20 carbon atoms, still more preferably 4 to 15 carbon atoms, and particularly preferably 4 to 12 carbon atoms.

Here, the number of carbon atoms described above means the number of carbon atoms constituting the ring skeleton, and does not include the number of carbon atoms included in a substituent.

The cyclic group for $R^3$ may be an aliphatic cyclic group, or may be an aromatic cyclic group. Of these, an aliphatic cyclic group is preferable.

Examples of the aliphatic cyclic group for $R^3$ include groups in which a part of the carbon atoms constituting the ring skeleton of the cyclic aliphatic hydrocarbon group described above are substituted with —$SO_2$— or —O—$SO_2$—.

Specific examples of the monocyclic group include: groups in which one hydrogen atom has been eliminated from a monocycloalkane in which —$CH_2$— constituting the ring skeleton has been substituted with —$SO_2$—; and groups in which one hydrogen atom has been eliminated from a monocycloalkane in which —$CH_2$—$CH_2$— constituting the ring skeleton has been substituted with —O—$SO_2$—. Also, specific examples of the polycyclic group include: groups in which one hydrogen atom has been eliminated from a polycycloalkane (bicycloalkane, tricycloalkane, tetracycloalkane, or the like) in which —$CH_2$— constituting the ring skeleton has been substituted with —$SO_2$—; and groups in which one hydrogen atom has been eliminated from a polycycloalkane in which —$CH_2$—$CH_2$— constituting the ring skeleton has been substituted with —O—$SO_2$—.

The cyclic group for $R^3$ may contain a substituent. Examples of the substituent include an alkyl group, an alkoxy group, a halogen atom, a halogenated alkyl group, a hydroxyl group, an oxygen atom (=O), —COOR", —OC(=O)R", a hydroxyalkyl group, and a cyano group. Here, R" represents a hydrogen atom or an alkyl group.

The alkyl group for the substituent is preferably an alkyl group of 1 to 6 carbon atoms. The alkyl group is preferably a linear or branched alkyl group. Specific examples thereof include a methyl group, an ethyl group, a propyl group, an isopropyl group, an n-butyl group, an isobutyl group, a tert-butyl group, a pentyl group, an isopentyl group, a neopentyl group, and a hexyl group. Of these, a methyl group or an ethyl group is preferable, and a methyl group is particularly preferable.

The alkoxy group for the substituent is preferably an alkoxy group of 1 to 6 carbon atoms. The alkoxy group is preferably a linear or branched alkoxy group. Specific examples thereof include groups in which an oxygen atom (—O—) has been bonded to an alkyl group described above as the alkyl group for the substituent.

Examples of the halogen atom for the substituent include a fluorine atom, a chlorine atom, a bromine atom, and an iodine atom. Of these, a fluorine atom is preferable.

Examples of the halogenated alkyl group for the substituent include a group in which a part or all of the hydrogen atoms within an alkyl group described above as the alkyl group for the substituent are substituted with the above halogen atoms. The halogenated alkyl group is preferably a fluorinated alkyl group, and particularly preferably a perfluoroalkyl group.

Each of R" within the above —COOR" and —OC(=O)R" is preferably a hydrogen atom, or a linear, branched, or cyclic alkyl group of 1 to 15 carbon atoms.

In the case that R" is a linear or branched alkyl group, R" preferably has 1 to 10 carbon atoms, more preferably 1 to 5 carbon atoms, and still more preferably a methyl group or an ethyl group.

In the case that R" is a cyclic alkyl group, R" preferably has 3 to 15 carbon atoms, more preferably 4 to 12 carbon atoms, and most preferably 5 to 10 carbon atoms. Specific examples of the cyclic alkyl group include groups in which one or more hydrogen atoms have been removed from a monocycloalkane or a polycycloalkane such as a bicycloalkane, tricycloalkane or tetracycloalkane, in which a fluorine atom or a fluorinated alkyl group may or may not be included as a substituent. Specific examples include groups in which at least one hydrogen atom has been removed from a monocycloalkane such as cyclopentane or cyclohexane; and groups in which at least one hydrogen atom has been removed from a polycycloalkane such as adamantane, norbornane, isobornane, tricyclodecane or tetracyclododecane.

The hydroxyalkyl group for the substituent preferably has 1 to 6 carbon atoms, and specific examples thereof include groups in which at least one hydrogen atom of the alkyl group described above for the substituent has been substituted with a hydroxyl group.

More specific examples of $R^3$ include groups represented by the general formulae (3-1) to (3-4) shown below.

[Chemical Formula 5]

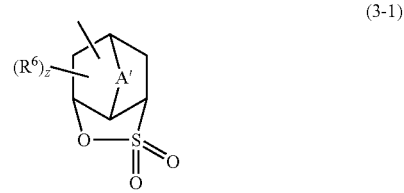

(3-1)

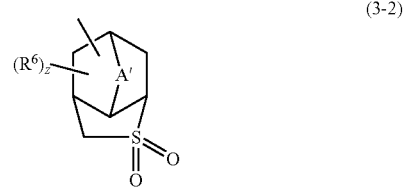

(3-2)

(3-3)

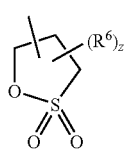

(3-4)

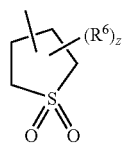

(In the above formulae, A' represents an oxygen atom, a sulfur atom, or an alkylene group of 1 to 5 carbon atoms which may contain an oxygen atom or a sulfur atom; z represents an integer of 0 to 2; $R^6$ represents an alkyl group, an alkoxy group, a halogenated alkyl group, a hydroxyl group, —COOR″, —OC(=O)R″, a hydroxyalkyl group or a cyano group; and R″ represents a hydrogen atom or an alkyl group.)

In the above formulae (3-1) to (3-4), A' represents an oxygen atom, a sulfur atom, or an alkylene group of 1 to 5 carbon atoms which may contain an oxygen atom (—O—) or a sulfur atom (—S—).

The alkylene group of 1 to 5 carbon atoms for A' is preferably a linear or branched alkylene group, and examples thereof include a methylene group, an ethylene group, an n-propylene group, and an isopropylene group.

When the alkylene group for A' contains an oxygen atom or a sulfur atom, a group in which —O— or —S— is located at the terminal of the alkylene group or between carbon atoms of the alkylene group can be mentioned as an example. Specific examples thereof include —O—CH$_2$—, —CH$_2$—O—CH$_2$—, —S—CH$_2$— and —CH$_2$—S—CH$_2$—.

A' is preferably —O— or an alkylene group of 1 to 5 carbon atoms, more preferably an alkylene group of 1 to 5 carbon atoms, and most preferably a methylene group.

z may be any of an integer of 0 to 2, and most preferably 0.

Here, when z is 2, a plurality of $R^6$ may be the same, or may be different from each other.

Examples of the alkyl group, the alkoxy group, the halogenated alkyl group, —COOR″, —OC(=O)R″, and a hydroxyalkyl group for $R^6$ include the same groups as the alkyl group, the alkoxy group, the halogenated alkyl group, —COOR″, —OC(=O)R″, and a hydroxyalkyl group, respectively, described above as the substituent which the cyclic group for $R^3$ may contain.

Specific cyclic groups represented by the above general formulae (3-1) to (3-4) are shown below. Here, in the formulae, the term "Ac" represents an acetyl group.

[Chemical Formula 6]

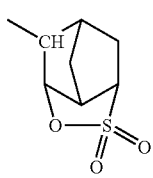

(3-1-1)

[Chemical Formula 7]

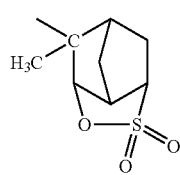

(3-1-2)

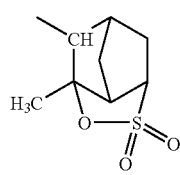

(3-1-3)

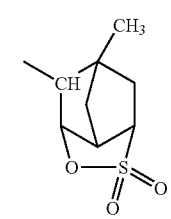

(3-1-4)

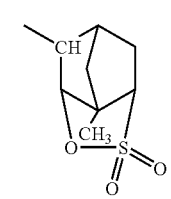

(3-1-5)

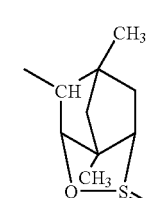

(3-1-6)

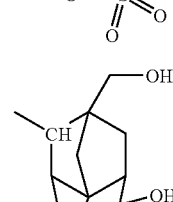

(3-1-7)

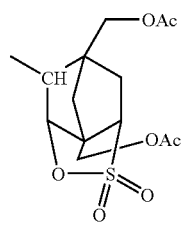

(3-1-8)

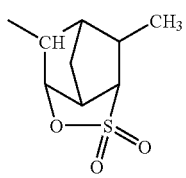

(3-1-9)

(3-1-10) 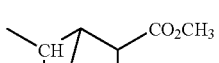
(3-1-11) 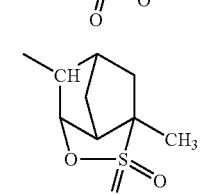
(3-1-12) 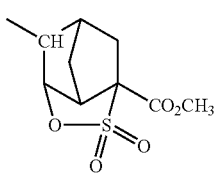
(3-1-13) 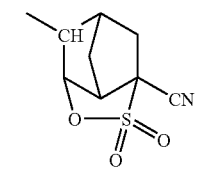
(3-1-14) 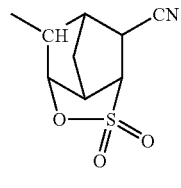
(3-1-15) 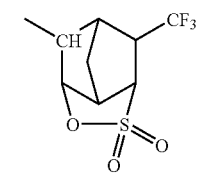
(3-1-16) 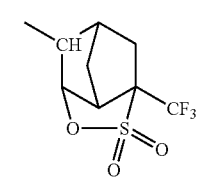
(3-1-17) 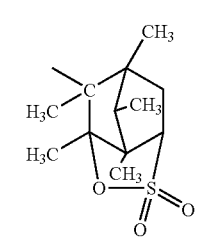
[Chemical Formula 8]
(3-1-18) 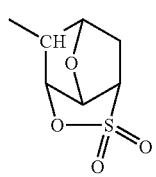
(3-1-19) 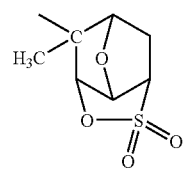
(3-1-20) 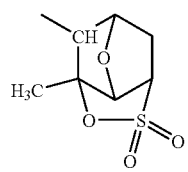
(3-1-21) 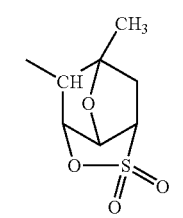
(3-1-22) 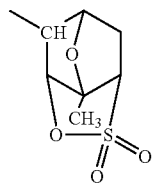
(3-1-23) 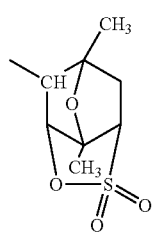
(3-1-24) 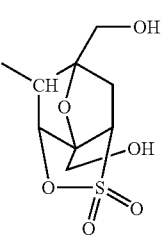

(3-1-25) 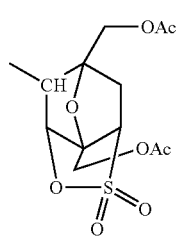

(3-1-26) 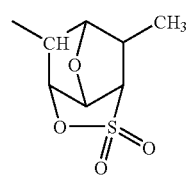

(3-1-27) 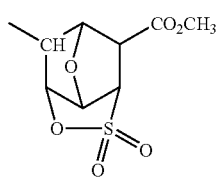

(3-1-28) 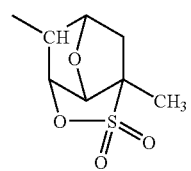

(3-1-29) 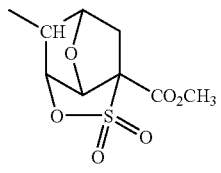

(3-1-30) 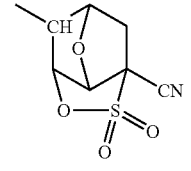

(3-1-31) 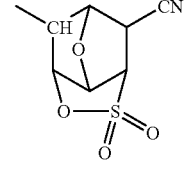

(3-1-32) 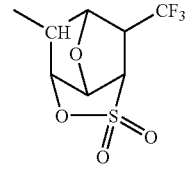

(3-1-33) 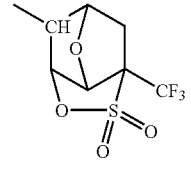

[Chemical Formula 9]

(3-2-1) 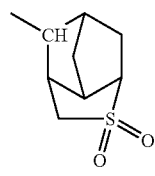

(3-2-2) 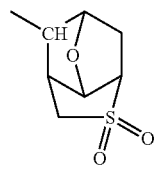

(3-3-1) 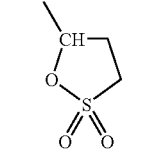

(3-4-1) 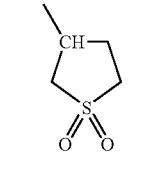

Of these, $R^3$ is preferably a cyclic group represented by the general formula (3-1), (3-3) or (3-4), and particularly preferably a cyclic group represented by the general formula (3-1).

Specifically, $R^3$ is preferably a cyclic group represented by the formulae (3-1-1), (3-1-18), (3-3-1) or (3-4-1), and $R^3$ is most preferably a cyclic group represented by the formula (3-1-1).

In the present invention, the structural unit (a0) is particularly preferably a structural unit represented by general formula (a0-1-11) shown below.

[Chemical Formula 10]

(a0-1-11) 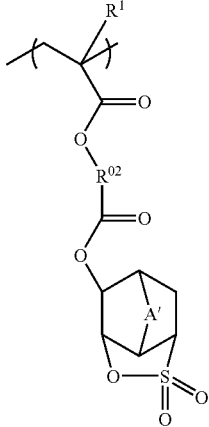

(In the formula, $R^1$ is as defined above; $R^{02}$ represents a linear or branched alkylene group or -A-C(=O)—O—B— (wherein A and B are as defined above); and A' is as defined above.)

The linear or branched alkylene group for $R^{02}$ preferably has 1 to 10 carbon atoms, more preferably 1 to 8 carbon atoms, still more preferably 1 to 5 carbon atoms, still more preferably 1 to 3 carbon atoms, and most preferably 1 or 2 carbon atoms.

In -A-C(=O)—O—B—, A and B each is preferably a linear or branched alkylene group, more preferably an alkylene group of 1 to 5 carbon atoms, and particularly preferably a methylene group or an ethylene group. Specific examples thereof include —(CH$_2$)$_2$—C(=O)—O—(CH$_2$)$_2$— and —(CH$_2$)$_2$—O—C(=O)—(CH$_2$)$_2$—.

A' is preferably a methylene group, an oxygen atom (—O—), or a sulfur atom (—S—).

As the structural unit (a0), one type of structural unit may be used, or two or more types may be used in combination.

The proportion of the structural unit (a0) in the polymeric compound (A0) is preferably 1 to 65 mol %, more preferably 5 to 50 mol %, still more preferably 10 to 40 mol %, and most preferably 20 to 40 mol %, based on the combined total of all the structural units that constitute the polymeric compound (A0), because it excels in resolution when a resist pattern is formed using a resist composition containing the polymeric compound (A0).

Structural Unit (a1)

Structural unit (a1) is a structural unit which does not correspond with the above structural unit (a0), and which is derived from an acrylate ester which has an acid dissociable, dissolution inhibiting group.

As the acid dissociable, dissolution inhibiting group in the structural unit (a1), any of the groups that have been proposed as acid dissociable, dissolution inhibiting groups for the base resins of chemically amplified resists can be used, provided the group has an alkali dissolution-inhibiting effect that renders the entire component (A1) poorly-soluble in an alkali developing solution, and then following dissociation by action of acid, causes the entire component (A1) to change to an alkali-soluble state. Generally, groups that form either a cyclic or chain-like tertiary alkyl ester with the carboxyl group of the (meth)acrylic acid or the like; and acetal-type acid dissociable, dissolution inhibiting groups such as alkoxyalkyl groups are widely known.

Here, the term "tertiary alkyl ester" means a structure in which an ester is formed by substituting the hydrogen atom of a carboxyl group with a chain-like or cyclic alkyl group, and a tertiary carbon atom within the chain-like or cyclic alkyl group is bonded to the oxygen atom at the terminal of the carbonyloxy group (—C(=O)—O—). In the tertiary alkyl ester, the bond between the oxygen atom and the tertiary carbon atom is cleaved under action of an acid.

Here, the chain-like or cyclic alkyl group may contain a substituent.

Hereinafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of the tertiary alkyl ester-type acid dissociable, dissolution inhibiting groups include aliphatic branched, acid dissociable, dissolution inhibiting groups and aliphatic cyclic group-containing acid diccociable, dissolution inhibiting groups.

Here, the term "aliphatic branched" means to contain a branched structure having no aromaticity. The "aliphatic branched, acid dissociable, dissolution inhibiting group" is not limited to groups (hydrocarbon groups) composed of carbon atoms and hydrogen atoms, and is preferably a hydrocarbon group.

Further, the "hydrocarbon group" may be either saturated or unsaturated, and is preferably saturated.

As the aliphatic branched, acid dissociable, dissolution inhibiting group, a group represented by the formula "—C(R$^{71}$)(R$^{72}$)(R$^{73}$)" can be used. In the formula, R$^{71}$ to R$^{73}$ each independently represents a linear alkyl group of 1 to 5 carbon atoms. The group represented by —C(R$^{71}$)(R$^{72}$)(R$^{73}$) preferably has 4 to 8 carbon atoms, and specific examples thereof include a tert-butyl group, a 2-methyl-2-butyl group, a 2-methyl-2-pentyl group, and a 3-methyl-3-pentyl group. Of these, a tert-butyl group is particularly preferable.

The term "aliphatic cyclic group" means a monocyclic or polycyclic group which has no aromaticity.

The "aliphatic cyclic group" within the structural unit (a1) may or may not contain a substituent. Examples of the substituent include a lower alkyl group of 1 to 5 carbon atoms, a lower alkoxy group of 1 to 5 carbon atoms, a fluorine atom, a fluorinated lower alkyl group of 1 to 5 carbon atoms, and an oxygen atom (=O).

The basic ring of the "aliphatic cyclic group" exclusive of substituents is not limited to groups (hydrocarbon groups) composed of carbon atoms and hydrogen atoms, and is preferably a hydrocarbon group.

Further, the "hydrocarbon group" may be either saturated or unsaturated, and is preferably saturated. The "aliphatic cyclic group" is preferably a polycyclic group.

Examples of the aliphatic cyclic groups include groups in which one or more hydrogen atoms have been removed from a monocycloalkane or a polycycloalkane such as a bicycloalkane, tricycloalkane or tetracycloalkane in which a lower alkyl group, a fluorine atom or a fluorinated lower alkyl group may or may not be included as a substituent. Specific examples thereof include groups in which at least one hydrogen atom has been removed from a monocycloalkane such as cyclopentane or cyclohexane; and groups in which at least one hydrogen atom has been removed from a polycycloalkane such as adamantane, norbornane, isobornane, tricyclodecane or tetracyclododecane. Also, the aliphatic cyclic group may be a group in which at least one hydrogen atom has been removed from a monocycloalkane in which a part of the carbon atoms constituting the ring have been substituted with ether oxygen atoms (—O—), or may be a group in which at least one hydrogen atom has been removed from a polycycloalkane in which a part of the carbon atoms constituting the rings have been substituted with ether oxygen atoms (—O—).

Examples of aliphatic cyclic group-containing acid dissociable, dissolution inhibiting groups include: (i) groups having a tertiary carbon atom within the ring skeleton of a monovalent aliphatic cyclic group; and (ii) groups having a monovalent aliphatic cyclic group and a branched alkylene group containing a tertiary carbon atom bonded to the monovalent aliphatic cyclic group.

Specific examples of "(i) groups having a tertiary carbon atom within the ring skeleton of a monovalent aliphatic cyclic group" include groups represented by the general formulae (1-1) to (1-9) shown below.

Specific examples of "(ii) groups having a monovalent aliphatic cyclic group and a branched alkylene group containing a tertiary carbon atom bonded to the monovalent aliphatic cyclic group" include groups represented by general formulae (2-1) to (2-6) shown below.

[Chemical Formula 11]

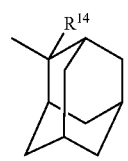

(1-1)

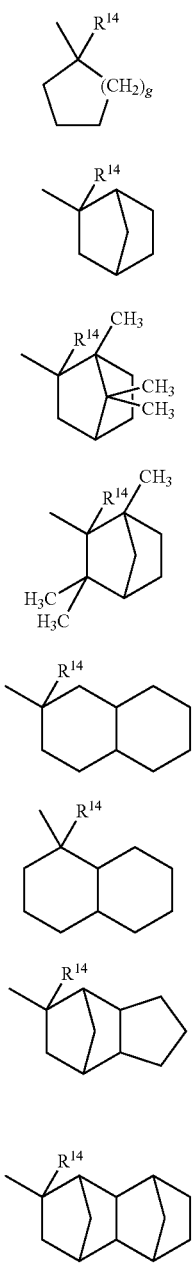

(In the above formulae, $R^{14}$ represents an alkyl group; and g represents an integer of 0 to 8.)

[Chemical Formula 12]

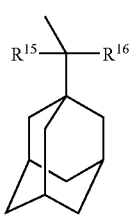

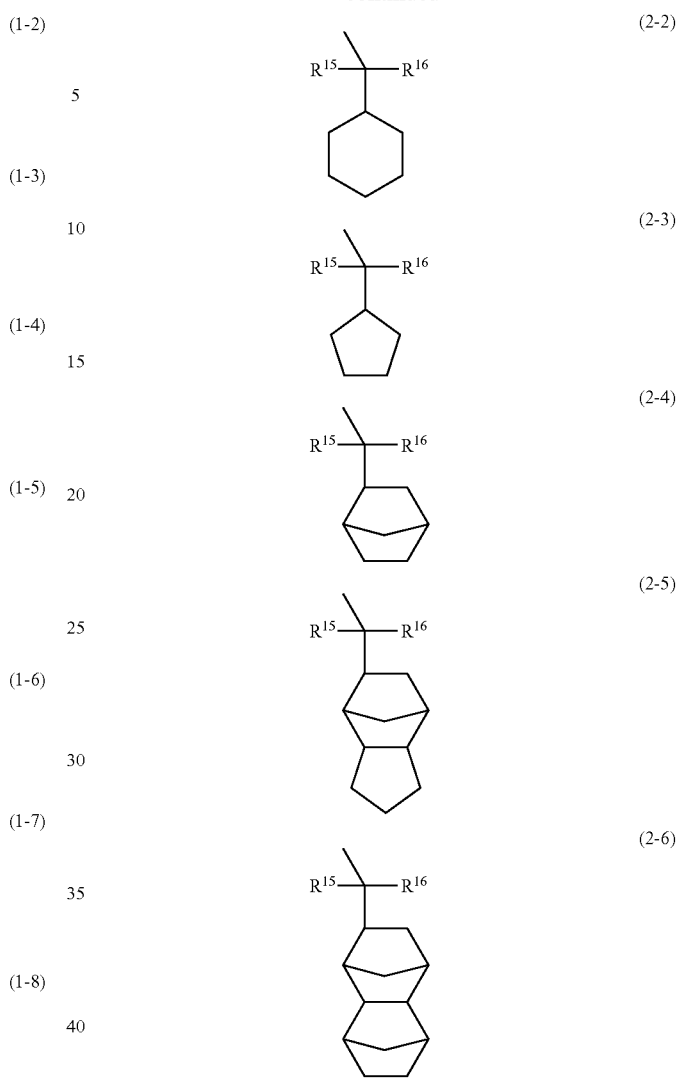

(In the above formulae, $R^{15}$ and $R^{16}$ each independently represents an alkyl group.)

The alkyl group for $R^{14}$ is preferably a linear or branched alkyl group.

The linear alkyl group for $R^{14}$ preferably has 1 to 5 carbon atoms, more preferably 1 to 4 carbon atoms, and still more preferably 1 or 2 carbon atoms. Specific examples thereof include a methyl group, an ethyl group, an n-propyl group, an n-butyl group, and an n-pentyl group. Of these, a methyl group, an ethyl group or an n-butyl group is preferable, and a methyl group or an ethyl group is more preferable.

The branched alkyl group for $R^{14}$ preferably has 3 to 10 carbon atoms, and more preferably 3 to 5 carbon atoms. Specific examples thereof include an isopropyl group, an isobutyl group, a tert-butyl group, an isopentyl group, and a neopentyl group. Of these, an isopropyl group is most preferable.

g is preferably an integer of 0 to 3, and more preferably an integer of 1 to 3, and still more preferably 1 or 2.

As the alkyl group for $R^{15}$ and $R^{16}$, the same alkyl groups as those described above for $R^{14}$ can be used.

In the above formulae (1-1) to (1-9) and (2-1) to (2-6), a part of carbon atoms constituting the ring(s) may be substituted with ether oxygen atoms (—O—).

Also, in the above formulae (1-1) to (1-9) and (2-1) to (2-6), a hydrogen atom bonded to a carbon atom constituting the ring(s) may be substituted with a substituent. Examples of the substituent include a lower alkyl group, a fluorine atom, and a fluorinated alkyl group.

An "acetal-type acid dissociable, dissolution inhibiting group" generally replaces a hydrogen atom at the terminal of an alkali-soluble group such as a carboxy group or a hydroxyl group, so as to be bonded to an oxygen atom. When an acid is generated upon exposure, the generated acid acts to break the bond between the acetal-type acid dissociable, dissolution inhibiting group and the oxygen atom to which the acetal-type, acid dissociable, dissolution inhibiting group is bonded.

Examples of the acetal-type acid dissociable, dissolution inhibiting groups include groups represented by the general formula (p1) shown below.

[Chemical Formula 13]

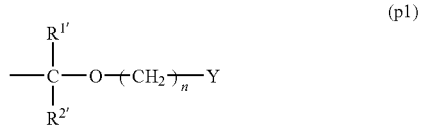

(p1)

(In the formula, $R^{1\prime}$ and $R^{2\prime}$ each independently represents a hydrogen atom or a lower alkyl group; n represents an integer of 0 to 3; and Y represents a lower alkyl group or an aliphatic cyclic group.)

In the above formula (p1), n is preferably an integer of 0 to 2, more preferably 0 or 1, and most preferably 0.

As the lower alkyl group for $R^{1\prime}$ and $R^{2\prime}$, the same lower alkyl groups as those described above for R can be used. As the lower alkyl group for $R^{1\prime}$ or $R^{2\prime}$, a methyl group or an ethyl group is preferable, and a methyl group is most preferable.

In the present invention, at least one of $R^{1\prime}$ and $R^{2\prime}$ is preferably a hydrogen atom. That is, it is preferable that the acid dissociable, dissolution inhibiting group (p1) be a group represented by the general formula (p1-1) shown below.

[Chemical Formula 14]

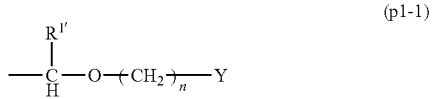

(p1-1)

(In the formula, $R^{1\prime}$, n, and Y are as defined above.)

As the lower alkyl group for Y, the same lower alkyl group as those described above for R can be used.

As the aliphatic cyclic group for Y, any of the aliphatic monocyclic or polycyclic groups which have been proposed for conventional ArF resists and the like can be used by being appropriately selected. For example, the same groups as those described above in the explanation of "aliphatic cyclic group" can be used.

Further, as the acetal-type, acid dissociable, dissolution inhibiting group, groups represented by general formula (p2) shown below can also be used.

[Chemical Formula 15]

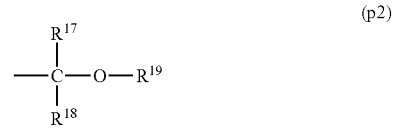

(p2)

(In the above formula, $R^{17}$ and $R^{18}$ each independently represents a linear or branched alkyl group or a hydrogen atom; and $R^{19}$ represents a linear, branched, or cyclic alkyl group. Alternatively, $R^{17}$ and $R^{19}$ each may independently represent a linear or branched alkylene group, in which the terminal of $R^{17}$ and the terminal of $R^{19}$ are bonded to form a ring.)

The alkyl group for $R^{17}$ and $R^{18}$ preferably has 1 to 15 carbon atoms, and may be either linear or branched. Of these, as the alkyl group for $R^{17}$ and $R^{18}$, an ethyl group or a methyl group is more preferable, and a methyl group is most preferable.

It is particularly preferable that either one of $R^{17}$ and $R^{18}$ be a hydrogen atom, and the other be a methyl group.

$R^{19}$ represents a linear, branched or cyclic alkyl group. $R^{19}$ preferably has 1 to 15 carbon atoms, and may be any of linear, branched or cyclic.

When $R^{19}$ represents a linear or branched alkyl group, $R^{19}$ is preferably an alkyl group of 1 to 5 carbon atoms, more preferably an ethyl group or a methyl group, and most preferably an ethyl group.

When $R^{19}$ represents a cyclic alkyl group, $R^{19}$ preferably has 4 to 15 carbon atoms, more preferably 4 to 12 carbon atoms, and most preferably 5 to 10 carbon atoms. Specific examples of the cyclic alkyl group include groups in which one or more hydrogen atoms have been removed from a monocycloalkane or a polycycloalkane such as a bicycloalkane, a tricycloalkane or a tetracycloalkane, in which a fluorine atom or a fluorinated alkyl group may or may not be included as a substituent. Specific examples thereof include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane, or tetracyclododecane. Of these, a group in which one or more hydrogen atoms have been removed from adamantane is preferable.

Also, in the general formula (p2), $R^{17}$ and $R^{19}$ each may independently represent a linear or branched alkylene group (and preferably an alkylene group of 1 to 5 carbon atoms), in which the terminal of $R^{19}$ is bonded to the terminal of $R^{17}$.

In this case, a cyclic group is formed by $R^{17}$, $R^{19}$, the oxygen atom to which $R^{19}$ is bonded, and the carbon atom to which the oxygen atom and $R^{17}$ are bonded. Such a cyclic group is preferably a 4 to 7-membered ring, and more preferably a 4 to 6-membered ring. Specific examples of the cyclic group include a tetrahydropyranyl group and a tetrahydrofuranyl group.

Specific examples of the acetal-type acid dissociable, dissolution inhibiting group include groups represented by the formulae (p3-1) to (p3-12) shown below.

[Chemical Formula 16]

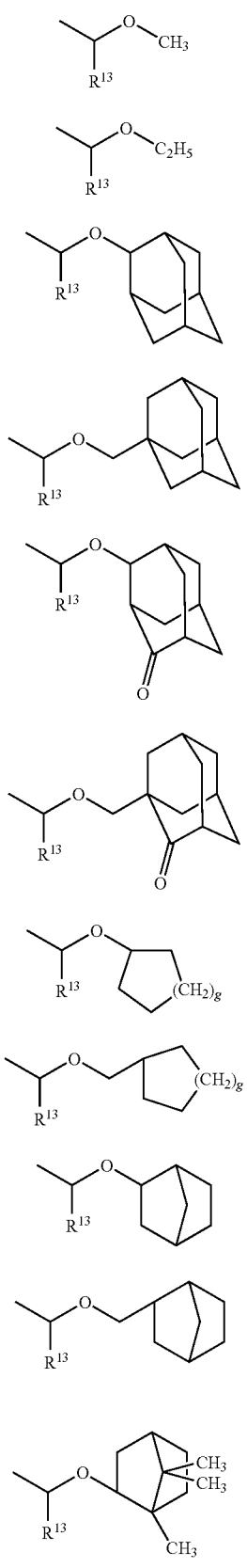

(p3-1)
(p3-2)
(p3-3)
(p3-4)
(p3-5)
(p3-6)
(p3-7)
(p3-8)
(p3-9)
(p3-10)
(p3-11)

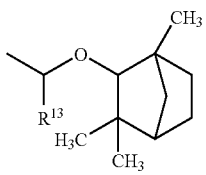

(p3-12)

(In the formula, $R^{13}$ represents a hydrogen atom or a methyl group; and g is as defined above.)

More specific examples of the structural unit (a1) include a structural unit represented by the general formula (a1-0-1) shown below and a structural unit represented by the general formula (a1-0-2) shown below.

[Chemical Formula 17]

(a1-0-1)

(a1-0-2)

(In the formulae, R represents a hydrogen atom, a lower alkyl group or a halogenated lower alkyl group; $X^1$ represents an acid dissociable, dissolution inhibiting group; $Y^2$ represents a bivalent linking group; and $X^2$ represents an acid dissociable, dissolution inhibiting group.)

In the formula (a1-0-1), R is the same as $R^1$ in the above general formula (a0-1).

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups. Of these, tertiary alkyl ester-type acid dissociable, dissolution inhibiting groups are preferable.

In the general formula (a1-0-2), R is as defined above.

$X^2$ is the same as $X^1$ described above in the general formula (a1-0-1).

Examples of the bivalent linking group for $Y^2$ include the same groups as $R^2$ in the above formula (a0-1).

$Y^2$ is preferably an alkylene group, a bivalent aliphatic cyclic group or a bivalent linking group containing a hetero atom described above in the explanation of $R^2$. Of these, $Y^2$ is preferably a bivalent linking group containing a hetero atom, and particularly preferably a linear group containing an oxygen atom as a hetero atom, such as a group containing an ester bond.

Of these, $Y^2$ is preferably a group represented by -A-O—B— or -A-C(=O)—O—B—, and particularly preferably a group represented by —$(CH_2)_x$—C(=O)—O—$(CH_2)_y$—.

x represents an integer of 1 to 5, preferably 1 or 2, and most preferably 1.

y represents an integer of 1 to 5, preferably 1 or 2, and most preferably 1.

Specific examples of the structural unit (a1) include structural units represented by the general formulae (a1-1) to (a1-4) shown below.

[Chemical Formula 18]

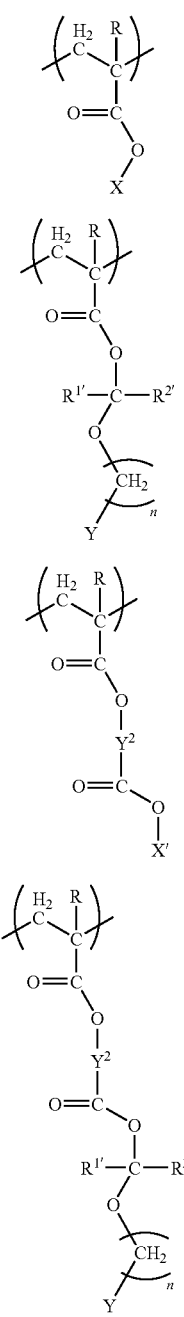

(In the formulae, X' represents a tertiary alkyl ester-type acid dissociable, dissolution inhibiting group; Y represents a lower alkyl group of 1 to 5 carbon atoms, or an aliphatic cyclic group; n represents an integer of 0 to 3; $Y^2$ represents a bivalent linking group; R is as defined above; and $R^{1\prime}$ and $R^{2\prime}$ each independently represents a hydrogen atom or a lower alkyl group of 1 to 5 carbon atoms.)

In the above formulae, as X', the same tertiary alkyl ester-type acid dissociable, dissolution inhibiting groups as those described in $X^1$ can be used.

$R^{1\prime}$, $R^{2\prime}$, n, and Y are respectively the same as $R^{1\prime}$, $R^{2\prime}$, n, and Y in the general formula (p1) described above in the explanation of "acetal-type acid dissociable, dissolution inhibiting group".

$Y^2$ is the same as $Y^2$ in the general formula (a1-0-2).

Specific examples of structural units represented by the general formulae (a1-1) to (a1-4) shown above include the following.

In each of the following formulae, $R^\alpha$ represents a hydrogen atom, a methyl group, or a trifluoromethyl group.

[Chemical Formula 19]

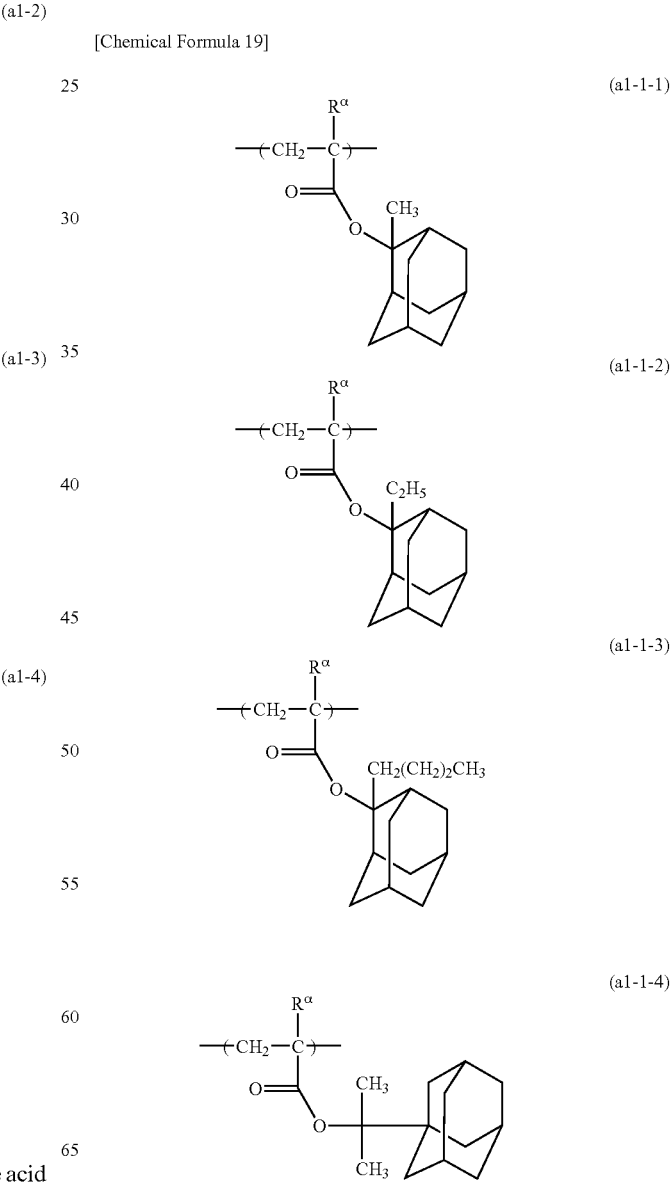

[Chemical Formula 20]

Structures (a-1-5) through (a1-1-16) shown.

(a1-1-17) 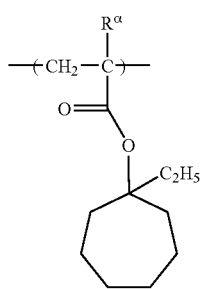
(a1-1-18) 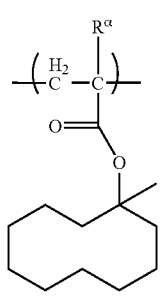
(a1-1-19) 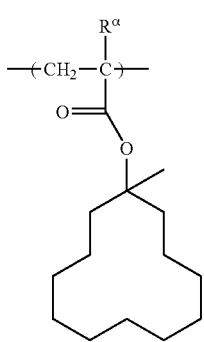
(a1-1-20) 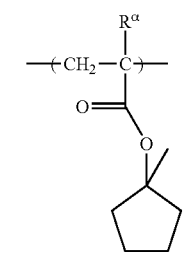
(a1-1-21) 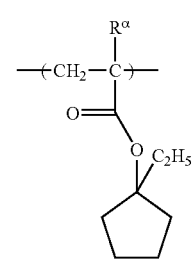
[Chemical Formula 21]
(a1-1-22) 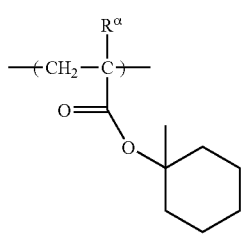
(a1-1-23) 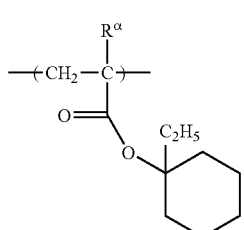
(a1-1-24) 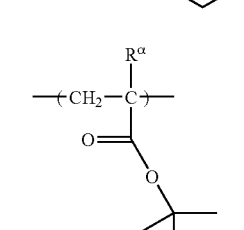
(a1-1-25) 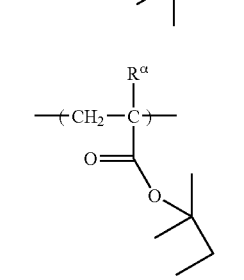
(a1-1-26) 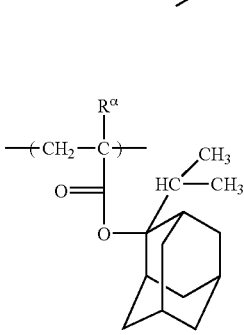
(a1-1-27) 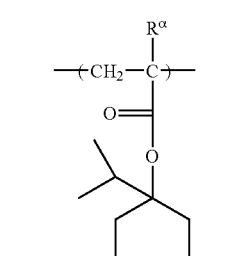

(a1-1-28)
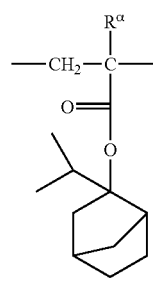
(a1-1-29)
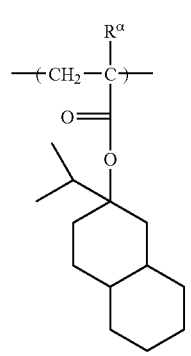
(a1-1-30)
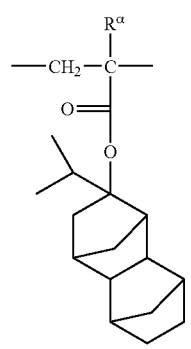
(a1-1-31)
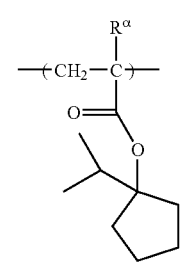
[Chemical Formula 22]
(a1-2-1)
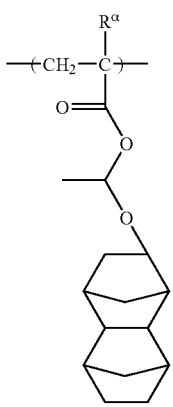
(a1-2-2)
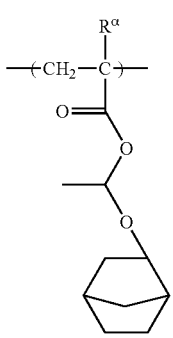
(a1-2-3)
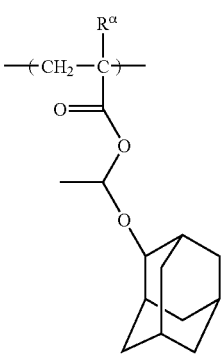
(a1-2-4)
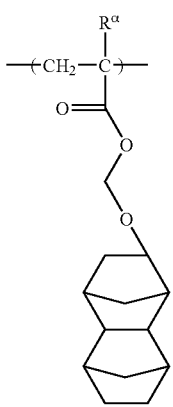

(a1-2-5) 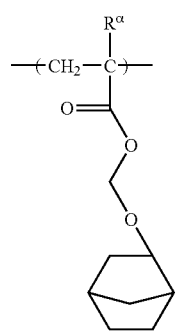
(a1-2-6) 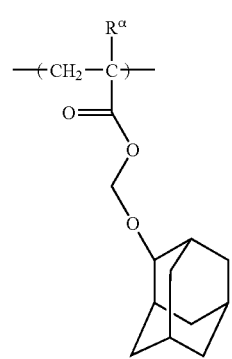
(a1-2-7) 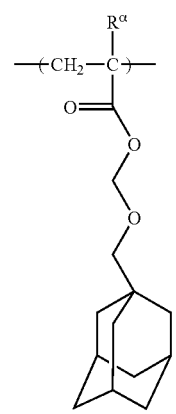
(a1-2-8) 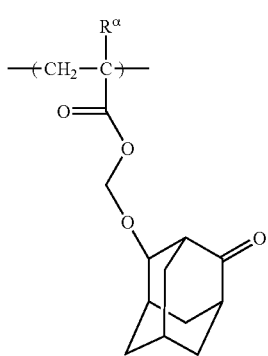
(a1-2-9) 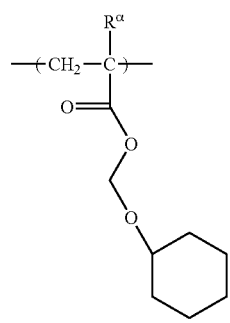
(a1-2-10) 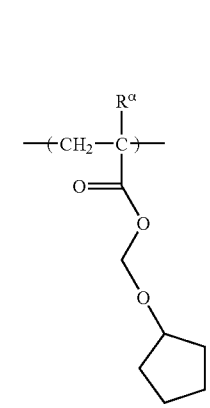
(a1-2-11) 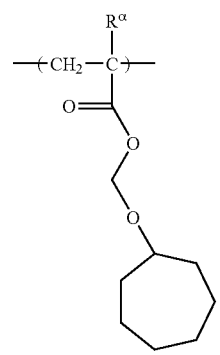
(a1-2-12) 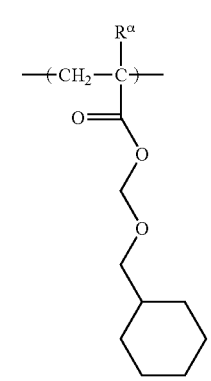

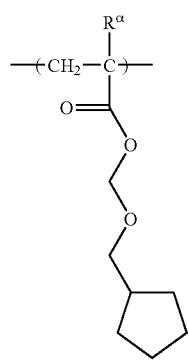 (a1-2-13)
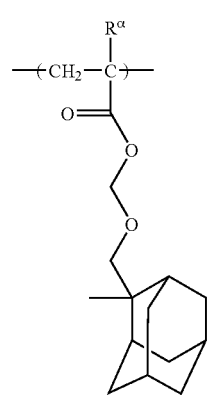 (a1-2-14)
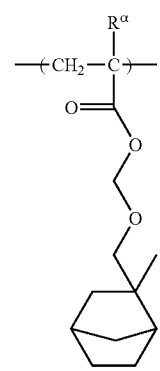 (a1-2-15)
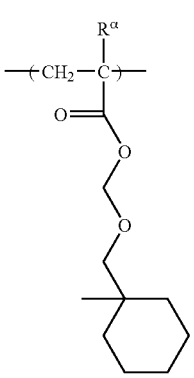 (a1-2-16)
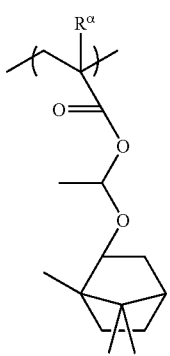 (a1-2-17)
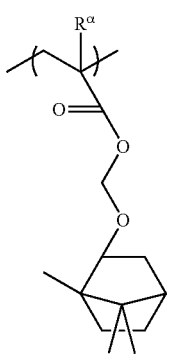 (a1-2-18)
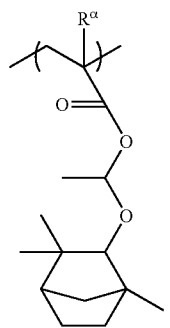 (a1-2-19)
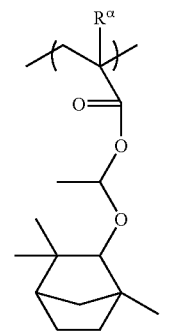 (a1-2-20)
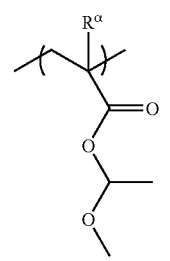 (a1-2-21)

-continued
(a1-2-22)
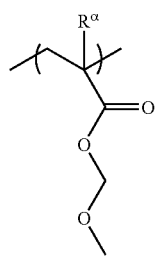
(a1-2-23)
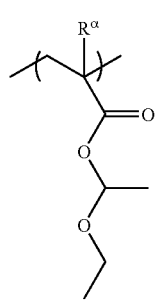
(a1-2-24)
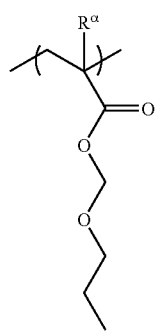
[Chemical Formula 23]
(a1-3-1)
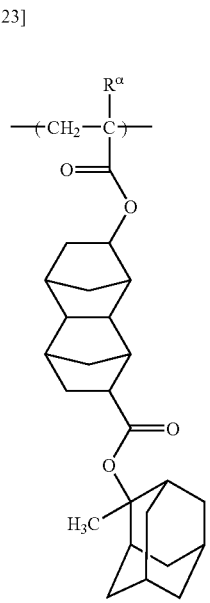
-continued
(a1-3-2)
(a1-3-3)
(a1-3-4)

(a1-3-5)
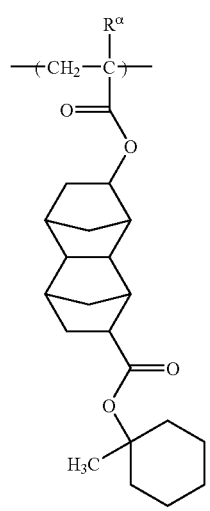
(a1-3-8)
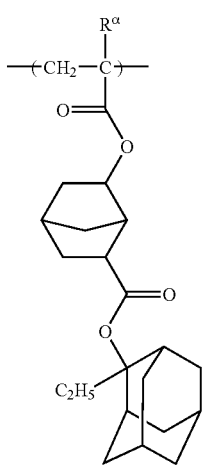
(a1-3-6)
(a1-3-9)
(a1-3-7)
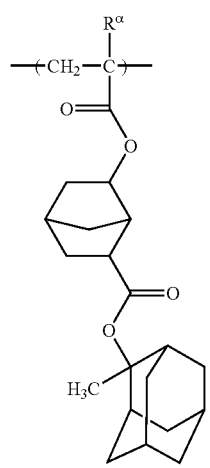
(a1-3-10)
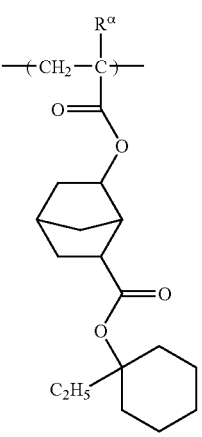

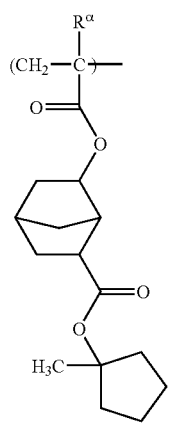 (a1-3-11)
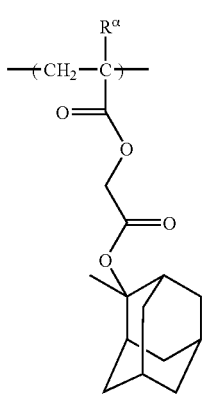 (a1-3-12)
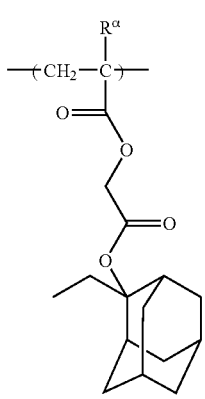 (a1-3-13)
(a1-3-14)
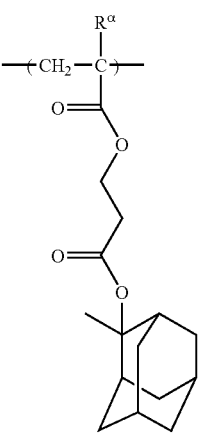 (a1-3-15)
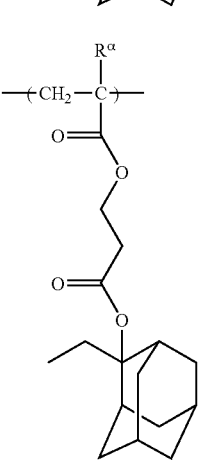 (a1-3-16)
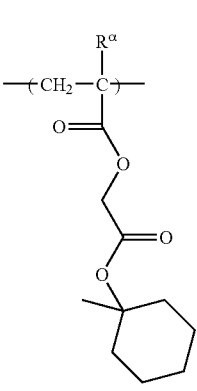 (a1-3-17)
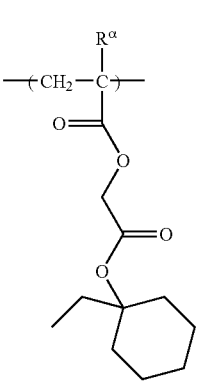 (a1-3-18)

[Chemical Formula 24]
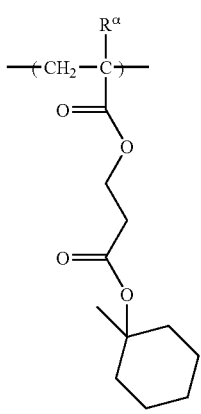
(a1-3-19)
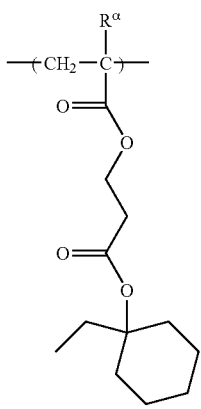
(a1-3-20)
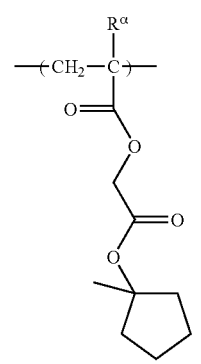
(a1-3-21)
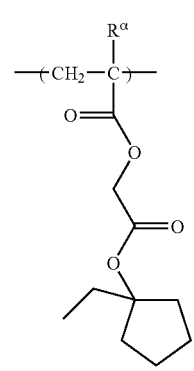
(a1-3-22)
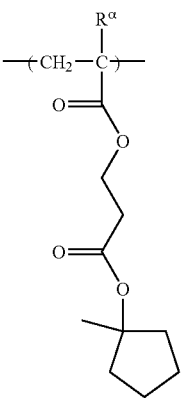
(a1-3-23)
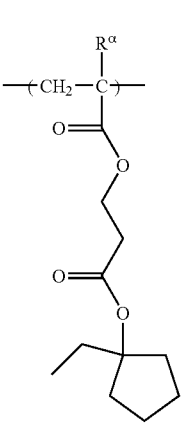
(a1-3-24)
[Chemical Formula 25]
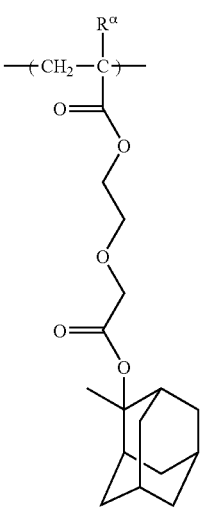
(a1-3-25)

(a1-3-26)
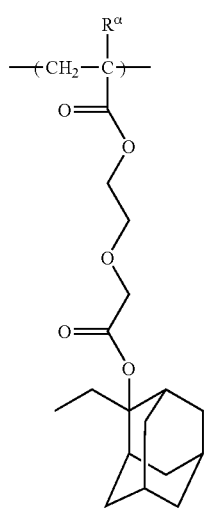
(a1-3-29)
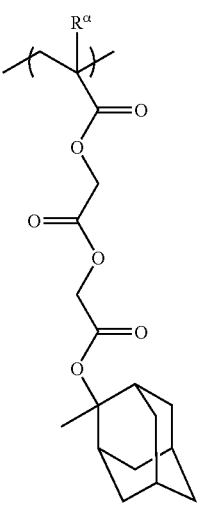
(a1-3-27)
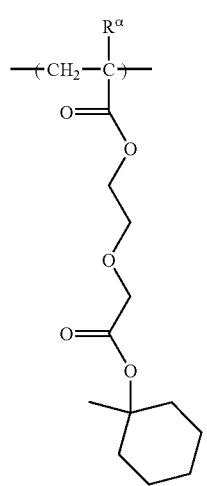
(a1-3-30)
(a1-3-28)
[Chemical Formula 26]
(a1-4-1)
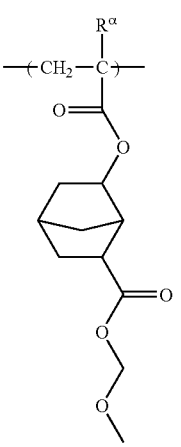

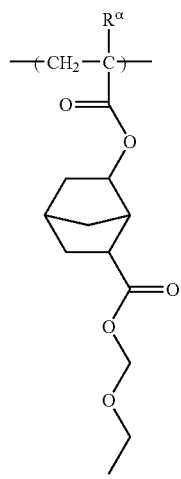
(a1-4-2)
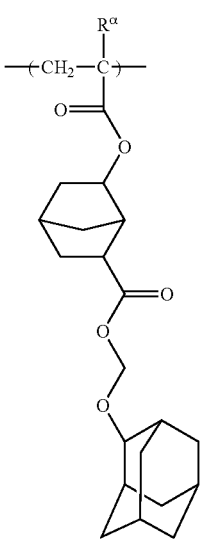
(a1-4-3)
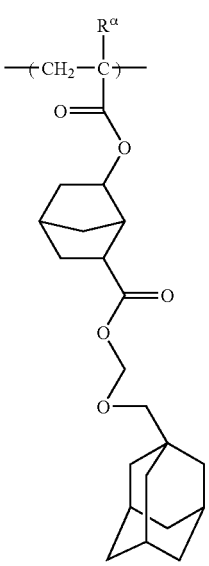
(a1-4-4)
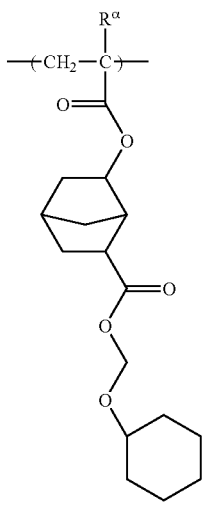
(a1-4-5)
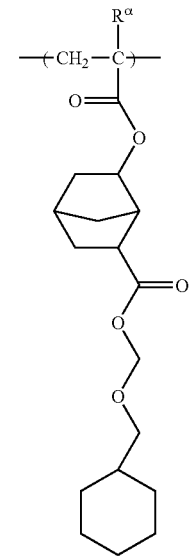
(a1-4-6)
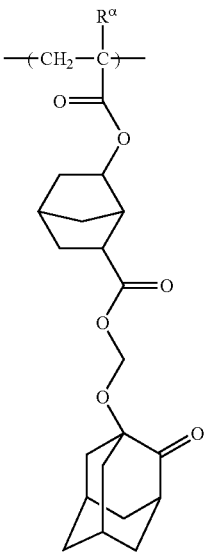
(a1-4-7)

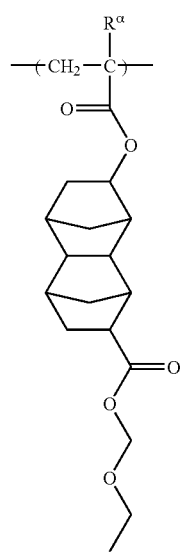
(a1-4-8)
(a1-4-9)
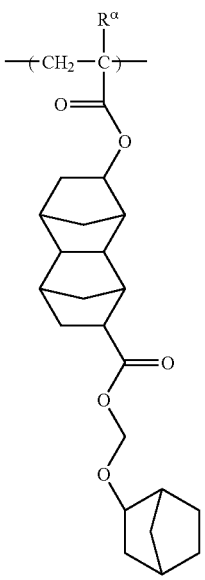
(a1-4-10)
(a1-4-11)

(a1-4-12)

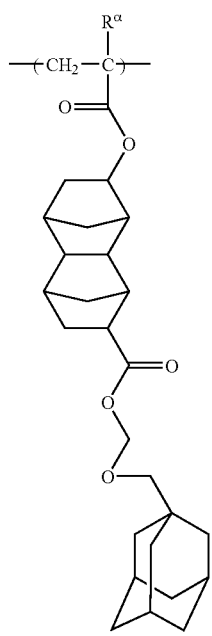

(a1-4-13)

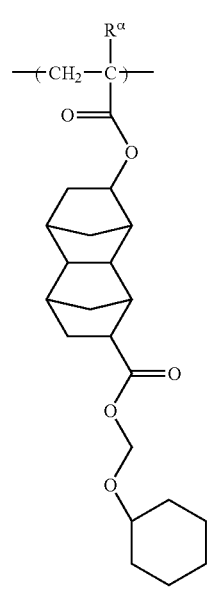

(a1-4-14)

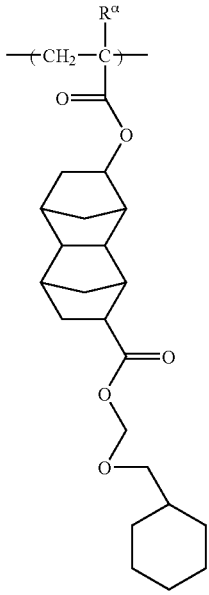

(a1-4-15)

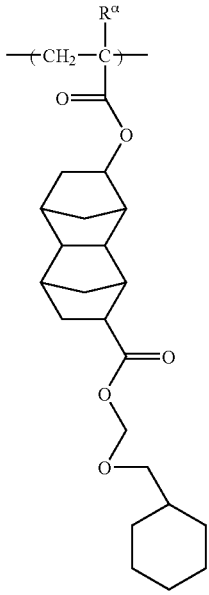

As the structural unit (a1), one kind of structural unit may be used, or two or more kinds may be used in combination.

In the present invention, the polymeric compound (A0) preferably contains, as the structural unit (a1), at least one kind of structural units selected from the group consisting of a structural unit represented by the general formula (a1-0-11) shown below, a structural unit represented by the general formula (a1-0-12) shown below, and a structural unit represented by the general formula (a1-0-2) shown below, because it excels in resolution, resist pattern shape and the like.

[Chemical Formula 27]

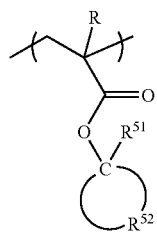
(a1-0-11)

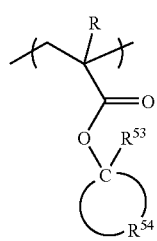
(a1-0-12)

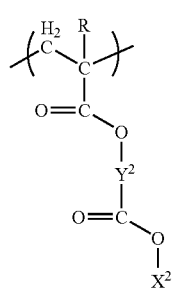
(a1-0-2)

(In the formulae, R represents a hydrogen atom, a lower alkyl group of 1 to 5 carbon atoms, or a halogenated lower alkyl group of 1 to 5 carbon atoms; $R^{51}$ represents an alkyl group; $R^{52}$ represents a group which forms an aliphatic monocyclic group together with the carbon atom to which $R^{52}$ is bonded; $R^{53}$ represents a branched alkyl group; $R^{54}$ represents a group which forms an aliphatic polycyclic group together with the carbon atom to which $R^{54}$ is bonded; $Y^2$ represents a bivalent linking group; and $X^2$ represents an acid dissociable, dissolution inhibiting group.)

In each of the formulae, R, $Y^2$ and $X^2$ are respectively as defined above.

In the formula (a1-0-11), examples of the alkyl group for $R^{51}$ include the same alkyl groups as those for $R^{14}$ in the above formula (1-1) to (1-9), and of these, a methyl group or an ethyl group is preferable, and an ethyl group is most preferable.

Examples of the aliphatic monocyclic group formed by $R^{52}$ and the carbon atom to which $R^{52}$ is bonded include the same aliphatic monocyclic groups as those in the aliphatic cyclic groups described above in the tertiary alkyl ester-type acid dissociable, dissolution inhibiting group. Specific examples thereof include a group in which one or more hydrogen atoms have been removed from a monocycloalkane. The monocycloalkane is preferably a 3 to 11-membered ring, more preferably a 3 to 8-membered ring, still more preferably a 4 to 6-membered ring, and particularly preferably a 5 or 6-membered ring.

In the monocycloalkane, a part of carbon atoms constituting the ring may or may not be substituted with ether oxygen atoms (—O—).

Also, the monocycloalkane may contain a lower alkyl group, a fluorine atom or a fluorinated alkyl group as a substituent.

Examples of $R^{52}$ constituting the aliphatic monocyclic group include a linear alkylene group in which an ether oxygen atom (—O—) may be positioned between carbon atoms.

Specific examples of the structural unit represented by the formula (a1-0-11) include structural units represented by the above formulae (a1-1-16) to (a1-1-23). Of these, a structural unit represented by the formula (a1-1-02) shown below which includes the structural units represented by the formulae (a1-1-16), (a1-1-17), and (a1-1-20) to (a1-1-23) is preferable. A structural unit represented by the formula (a1-1-02') shown below is also preferable.

In each of the formulae below, h is preferably 1 or 2, and most preferably 2.

[Chemical Formula 28]

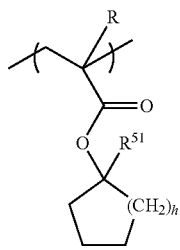
(a1-1-02)

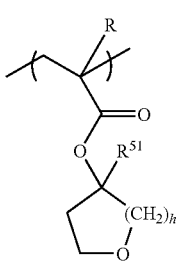
(a1-1-02')

(In the above formulae, R and $R^{51}$ are respectively as defined above; and h represents an integer of 1 to 3.)

In the formula (a1-0-12), examples of the branched alkyl group for $R^{53}$ include the same branched alkyl groups as those described for $R^{14}$ in the above formulae (1-1) to (1-9), and of these, an isopropyl group is most preferable.

Examples of the aliphatic polycyclic group formed by $R^{54}$ and the carbon atom to which $R^{54}$ is bonded include the same aliphatic polycyclic groups as those in the aliphatic cyclic groups described above in the tertiary alkyl ester-type acid dissociable, dissolution inhibiting group.

Specific examples of the structural unit represented by the formula (a1-0-12) include structural units represented by the above formulae (a1-1-26) to (a1-1-31).

As the structural unit represented by the formula (a1-0-2), a structural unit represented by the above formula (a1-3) or (a1-4) can be used, and of these, a structural unit represented by the formula (a1-3) is particularly preferable.

The structural unit represented by the formula (a1-0-2) is particularly preferably a structural unit in which $Y^2$ in the formula is a group represented by -A-O—B— or -A-C(=O)—O—B—.

Preferable examples of such a structural unit include a structural unit represented by the general formula (a1-3-01), a structural unit represented by the general formula (a1-3-02), and a structural unit represented by the general formula (a1-3-03).

[Chemical Formula 29]

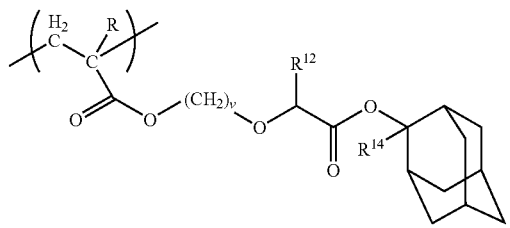

(a1-3-01)

(In the formula, R and $R^{14}$ are respectively as defined above; $R^{12}$ represents a hydrogen atom or a methyl group; and v represents an integer of 1 to 10.)

[Chemical Formula 30]

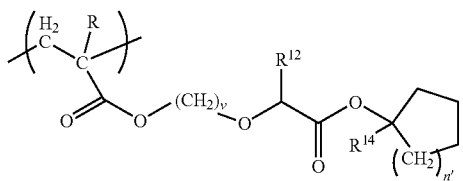

(a1-3-02)

(In the formula, R and $R^{14}$ are respectively as defined above; $R^{12}$ represents a hydrogen atom or a methyl group; v represents an integer of 1 to 10, and n' represents an integer of 0 to 3.)

[Chemical Formula 31]

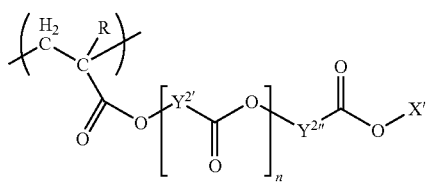

(a1-3-03)

(In the above formula, R is as defined above; $Y^{2'}$ and $Y^{2''}$ each independently represents a bivalent linking group; X' represents an acid dissociable, dissolution inhibiting group, and n represents an integer of 0 to 3.)

In the formulae (a1-3-01) and (a1-3-02), $R^{12}$ is preferably a hydrogen atom.

v is preferably an integer of 1 to 8, more preferably an integer of 1 to 5, and most preferably 1 or 2.

n' is preferably 1 or 2, and most preferably 2.

Specific examples of the structural unit represented by the formula (a1-3-01) include structural units represented by the above formulae (a1-3-25) to (a1-3-26).

Specific examples of the structural unit represented by the formula (a1-3-02) include structural units represented by the above formulae (a1-3-27) to (a1-3-28).

In the formula (a1-3-03), examples of the bivalent linking group for $Y^{2'}$ and $Y^{2''}$ include the same bivalent linking groups as those for $Y^2$ described above in the general formula (a1-3).

$Y^{2'}$ is preferably a bivalent hydrocarbon group which may contain a substituent, more preferably a linear aliphatic hydrocarbon group, and still more preferably a linear alkylene group. Of these, $Y^{2'}$ is particularly preferably a linear alkylene group of 1 to 5 carbon atoms, and most preferably a methylene group or an ethylene group.

$Y^{2''}$ is preferably a bivalent hydrocarbon group which may contain a substituent, more preferably a linear aliphatic hydrocarbon group, and still more preferably a linear alkylene group. Of these, $Y^{2''}$ is particularly preferably a linear alkylene group of 1 to 5 carbon atoms, and most preferably a methylene group or an ethylene group.

The acid dissociable, dissolution inhibiting group for X' is as defined above, and is preferably a tertiary alkyl ester-type acid dissociable, dissolution inhibiting group, and more preferably "(i) a group having a tertiary carbon atom within the ring skeleton of a monovalent aliphatic cyclic group" as described above. Of these, a group represented by the general formula (1-1) is preferable.

n is an integer of 0 to 3, preferably 0 to 2, more preferably 0 or 1, and most preferably 1.

The structural unit represented by the formula (a1-3-03) is preferably a structural unit represented by the general formula (a1-3-03-1) or (a1-3-03-2) shown below. Of these, a structural unit represented by the formula (a1-3-03-1) is preferable, and a structural unit represented by the above formulae (a1-3-29) to (a1-3-30) is particularly preferable.

[Chemical Formula 32]

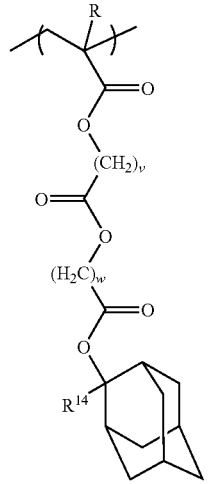

(a1-3-03-1)

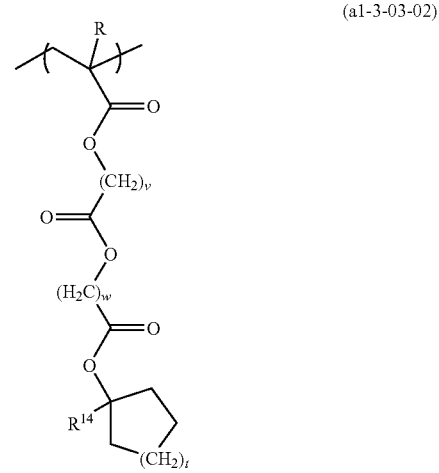

(a1-3-03-2)

(In the formulae, R and $R^{14}$ are respectively as defined above; v represents an integer of 1 to 10; w represents an integer of 1 to 10; and t represents an integer of 0 to 3.)

v is preferably an integer of 1 to 5, and particularly preferably 1 or 2.

w is preferably an integer of 1 to 5, and particularly preferably 1 or 2.

t is preferably an integer of 1 to 3, and particularly preferably 1 or 2.

In the present invention, the polymeric compound (A0) particularly preferably contains at least two kinds of the structural unit (a1).

In this case, at least one kind selected from at least two kinds of the structural unit (a1) is preferably at least one kind selected from the group consisting of structural units represented by the above general formula (a1-0-11), structural units represented by the general formula (a1-0-12), and structural units represented by the general formula (a1-0-2).

In this case, at least two kinds of the structural units (a1) described above may be composed of structural units selected from the group consisting of structural units represented by the above general formula (a1-0-11), structural units represented by the above general formula (a1-0-12), and structural units represented by the above general formula (a1-0-2); or may be constituted by at least one kind selected from these structural units and a structural unit (a1) which does not correspond with these structural units.

As the above structural unit (a1) which do not correspond with structural units represented by the general formulae (a1-0-11), (a1-0-12) and (a1-0-2), and which can be used in combination with at least one kind selected from structural units represented by the general formulae (a1-0-11), (a1-0-12) and (a1-0-2), structural units represented by the general formula (a1-1-01) shown below which includes the formulae (a1-1-1) to (a1-1-2) and (a1-1-7) to (a1-1-15) described above as specific examples of the general formula (a1-1); structural units represented by the above general formula (a1-2); and structural units represented by the above general formula (a1-4) can be used.

The structural unit represented by the general formula (a1-1-01) is particularly preferably a structural unit represented by the general formula (a1-1-101) shown below which includes the formulae (a1-1-1) to (a1-1-2).

[Chemical Formula 33]

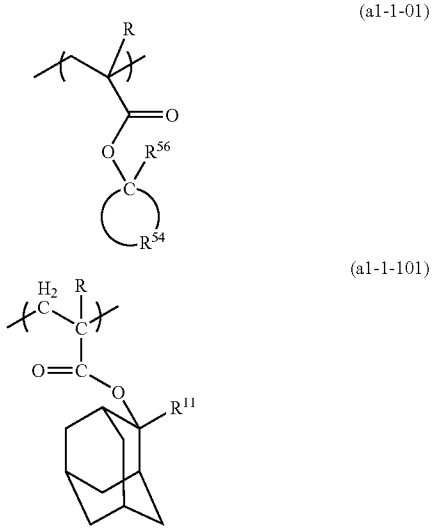

(In the formulae, R is as defined above; $R^{55}$ and $R^{11}$ each independently represents a linear alkyl group of 1 to 5 carbon atoms; and $R^{54}$ is as defined above.)

The proportion of the structural unit (a1) in the polymeric compound (A0) is preferably 10 to 80 mol %, more preferably 20 to 70 mol %, and still more preferably from 25 to 60 mol %, based on the combined total of all the structural units that constitute the polymeric compound (A0). When this proportion is not less than the lower limit in the above range, then a pattern can be easily formed using a resist composition which includes the structural unit (a1), whereas when the proportion is not more than the upper limit in the above range, a good quantitative balance with the other structural units can be attained.

Structural Unit (a3)

The structural unit (a3) is a structural unit derived from an acrylate ester which has a polar group-containing aliphatic hydrocarbon group.

When the component (A0) includes the structural unit (a3), the hydrophilicity of the component (A1) is improved, and hence, the compatibility of the component (A1) with the developing solution is improved. As a result, the solubility of the exposed portions in an alkali developing solution improves, which contributes to favorable improvements in the resolution.

Examples of the polar group include a hydroxyl group, a cyano group, a carboxyl group, and a hydroxyalkyl group in which a part of the hydrogen atoms in an alkyl group is substituted with fluorine atoms. Of these, a hydroxyl group is particularly preferable.

Examples of the aliphatic hydrocarbon group include a linear or branched hydrocarbon group of 1 to 10 carbon atoms (preferably an alkylene group), and a polycyclic aliphatic hydrocarbon group (polycyclic group). The polycyclic group can be appropriately selected from the multitude of structural units proposed as resins in resist compositions for ArF excimer lasers and the like. The polycyclic group preferably has 7 to 30 carbon atoms.

Of these, a structural unit derived from an acrylate ester having a polycyclic aliphatic group which contains a hydroxyl group, a cyano group, a carboxyl group, or a hydroxyalkyl group in which a part of the hydrogen atoms within an alkyl group has been substituted with fluorine atoms is more preferable. Examples of the polycyclic group include groups in which two or more hydrogen atoms have been removed from a bicycloalkane, a tricycloalkane, a tetracycloalkane, or the like. Specific examples include a group in which two or more hydrogen atoms have been removed from a polycycloalkane such as adamantane, norbornane, isobornane, tricyclodecane, or tetracyclododecane. Of these polycyclic groups, a group in which two or more hydrogen atoms have been removed from adamantane, norbornane, or tetracyclododecane is industrially preferable.

As the structural unit (a3), for example, a structural unit derived from a hydroxyethyl ester of acrylic acid is preferable, when the hydrocarbon group within the polar group-containing aliphatic hydrocarbon group is a linear or branched hydrocarbon group of 1 to 10 carbon atoms. On the other hand, a structural unit represented by the general formula (a3-1), (a3-2), or (a3-3) shown below is preferable, when the hydrocarbon group is a polycyclic group.

[Chemical Formula 34]

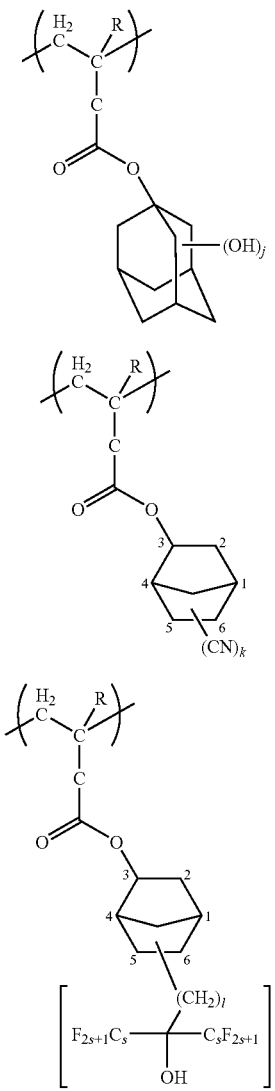

(wherein, R is as defined above; j represents an integer of 1 to 3; k represents an integer of 1 to 3; t' represents an integer of 1 to 3; l represents an integer of 1 to 5; and s represents an integer of 1 to 3.)

In the general formula (a3-1), j is preferably 1 or 2, and more preferably 1. In the case that j be 2, a structural unit in which the hydroxyl groups are bonded to the 3-position and 5-position of the adamantyl group is preferable. In the case that j be 1, a structural unit in which the hydroxyl group is bonded to the 3-position of the adamantyl group is preferable. Of these, j is preferably 1, and a structural unit in which the hydroxyl group is bonded to the 3-position of adamantyl group is particularly preferable.

In the general formula (a3-2), k is preferably 1. In the general formula (a3-2), a cyano group is preferably bonded to the 5-position or 6-position of the norbornyl group.

In the general formula (a3-3), t' is preferably 1. l is preferably 1. s is preferably 1. It is preferable that a 2-norbornyl group or a 3-norbornyl group be bonded to the terminal of the carboxyl group in the acrylic acid. It is preferable that the fluorinated alkyl alcohol in the formula (a3-3) be bonded to the 5-position or 6-position of the norbornyl group.

As the structural unit (a3), one type of structural unit may be used, or two or more types may be used in combination.

The proportion of the structural unit (a3) in the polymeric compound (A0) is preferably from 5 to 50 mol %, more preferably from 5 to 40 mol %, and still more preferably from 5 to 25 mol %, based on the combined total of all the structural units that constitute the polymeric compound (A0). When this proportion is not less than the lower limit in the above range, then the effect made by containing the structural unit (a3) can be sufficiently obtained. When the proportion is not more than the upper limit in the above range, a good quantitative balance with the other structural units can be attained.

Other Structural Units

The polymer compound (A0) may also include a structural unit other than the structural units (a0), (a1) and (a3) within the range that the effect of the present invention is not impaired.

There are no particular restrictions on such a structural unit as long as it is a structural unit which cannot be classified as one of the above structural units (a0), (a1) and (a3), and any of the multitude of conventional structural units used within resist resins for ArF excimer lasers or KrF excimer lasers (and particularly for ArF excimer lasers) can be used.

Suitable examples of the structural unit include a structural unit (a2) derived from an acrylate ester which has a lactone-containing cyclic group. Also, examples of the structural unit include a structural unit (a4) derived from an acrylate ester which has non-acid dissociable aliphatic polycyclic group, and a structural unit (a5) which is a structural unit represented by the above general formula (a0-1) in which $R^2$ is a bivalent hydrocarbon group which may contain a substituent.

Structural Unit (a2)

Structural unit (a2) is a structural unit derived from an acrylate ester which has a lactone-containing cyclic group.

In the present invention, it is preferable that the polymeric compound (A0) further include the structural unit (a2) derived from an acrylate ester which has a lactone-containing cyclic group, in addition to the structural units (a0) and (a1) or the structural units (a0), (a1) and (a3).

Here, the term "lactone-containing cyclic group" means a cyclic group containing a single ring (lactone ring) which has a "—O—C(O)—" structure. This lactone ring is counted as the first ring, and groups that contain only the lactone ring are referred to as monocyclic groups, whereas groups that also contain other ring structures are described as polycyclic groups regardless of the structure of the other rings.

In the case of using the component (A0) to form a resist film, the lactone-containing cyclic group of the structural unit (a2) is effective at improving the adhesion between the resist film and a substrate, and improving compatibility with the aqueous developing solution.

The structural unit (a2) can be used arbitrarily without any particular restriction.

Specific examples of the lactone-containing monocyclic group include groups in which one hydrogen atom has been removed from 4 to 6-membered lactone ring. such as a group in which one hydrogen atom has been removed from β-propiolactone, a group in which one hydrogen atom has been removed from γ-butyrolactone, and a group in which one hydrogen atom has been removed from δ-valerolactone. Furthermore, specific examples of the lactone-containing polycyclic group include groups in which one hydrogen atom has been eliminated from a bicycloalkane, a tricycloalkane, or a tetracycloalkane which contains a lactone ring.

Specific examples of the structural unit (a2) include structural units represented by the general formulae (a2-1) to (a2-5) shown below.

[Chemical Formula 35]

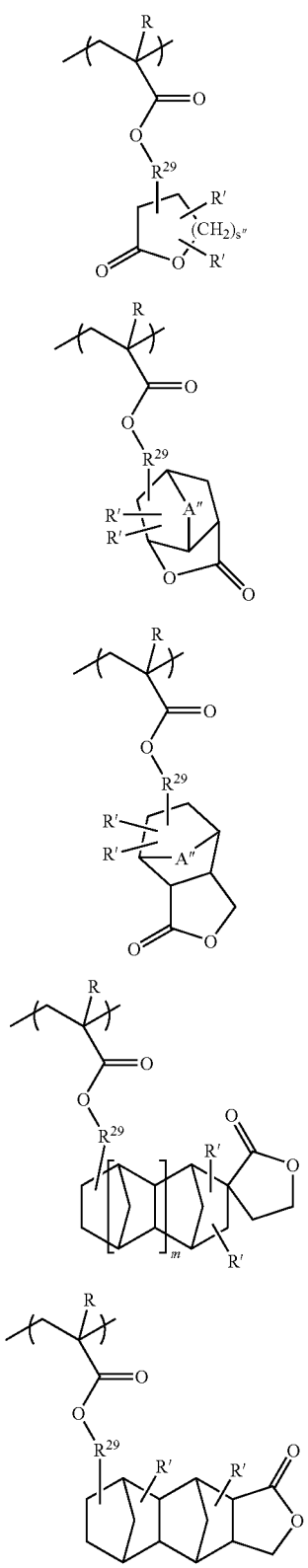

(In the above formulae, R represents a hydrogen atom, a lower alkyl group or a halogenated lower alkyl group; R' each independently represents a hydrogen atom, an alkyl group of 1 to 5 carbon atoms, an alkoxy group of 1 to 5 carbon atoms, or —COOR", wherein R" represents a hydrogen atom or an alkyl group; $R^{29}$ represents a single bond or a bivalent linking group; s" represents an integer of 0 to 2; A" represents an oxygen atom, a sulfur atom, or an alkylene group of 1 to 5 carbon atoms which may contain an oxygen atom or a sulfur atom; and m represents an integer of 0 or 1.)

R in the general formula (a2-1) to (a2-5) is the same as R described above in the structural unit (a1).

Examples of the alkyl group of 1 to 5 carbon atoms, the alkoxy group of 1 to 5 carbon atoms, and —COOR" for R' include the same groups as the alkyl group, the alkoxy group, and —COOR", respectively, for $R^6$ above in the general formula (3-1). In the general formulae (a2-1) to (a2-5), R' is preferably a hydrogen atom in terms of industrial availability.

Examples of A" include the same as A' described above in the general formula (3-1).

$R^{29}$ represents a single bond or a bivalent linking group. As the bivalent linking group, the same bivalent linking groups as those described in $R^2$ in the above general formula (a0-1) can be used, and of these, an alkylene group, an ester group (—C(=O)—O—), or a combination thereof is preferably used. The alkylene group as the bivalent linking group for $R^{29}$ is more preferably a linear or branched alkylene group. Specific examples thereof include the same linear alkylene groups and branched alkylene groups as those described above in $R^2$.

s" is preferably an integer of 1 or 2.

Specific examples of structural units represented by the above general formulae (a2-1) and (a2-5) include the following. In each of the following formulae, represents a hydrogen atom, a methyl group, or a trifluoromethyl group.

[Chemical Formula 36]

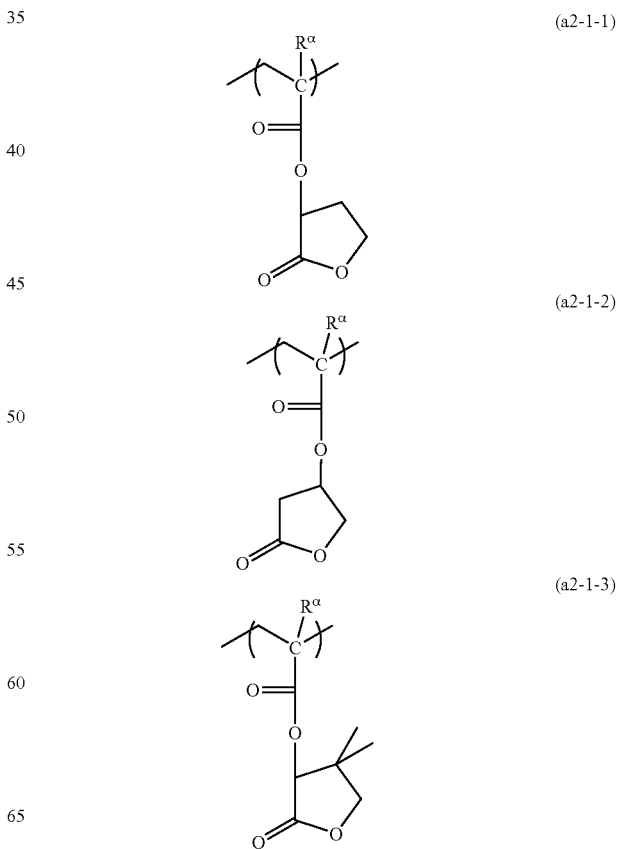

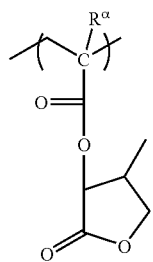 (a2-1-4)
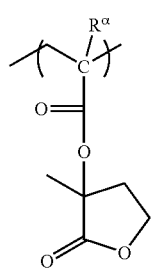 (a2-1-5)
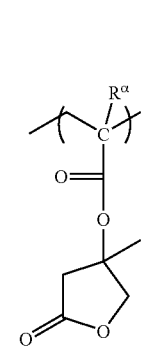 (a2-1-6)
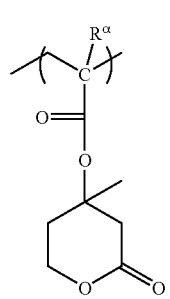 (a2-1-7)
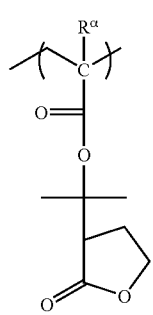 (a2-1-8)
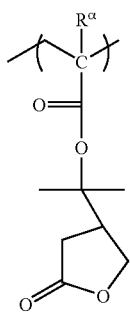 (a2-1-9)
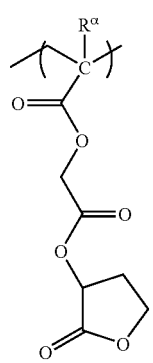 (a2-1-10)
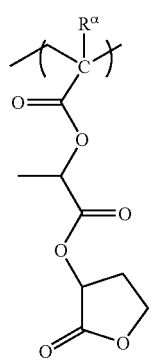 (a2-1-11)
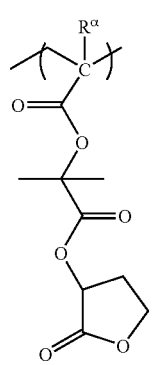 (a2-1-12)

(a2-1-13)
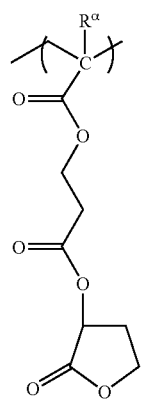
[Chemical Formula 37]
(a2-2-1)
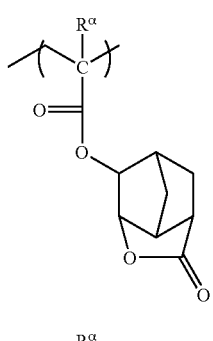
(a2-2-2)
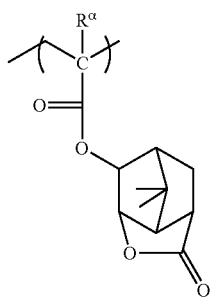
(a2-2-3)
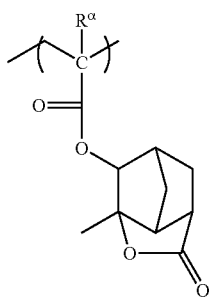
(a2-2-4)
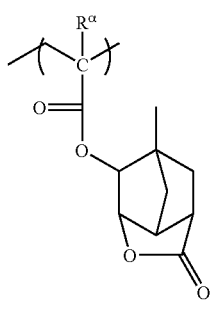
(a2-2-5)
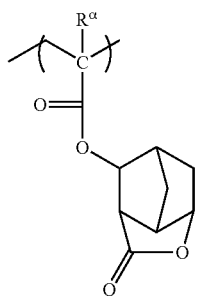
(a2-2-6)
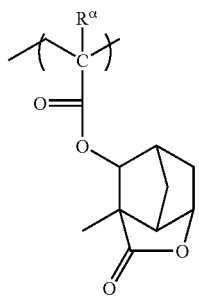
(a2-2-7)
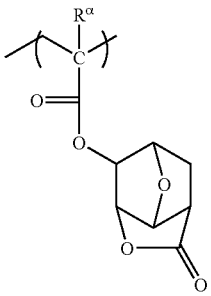
(a2-2-8)
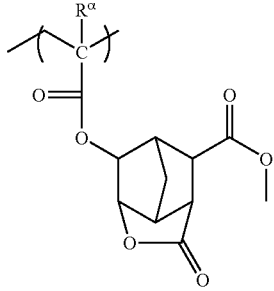
(a2-2-9)
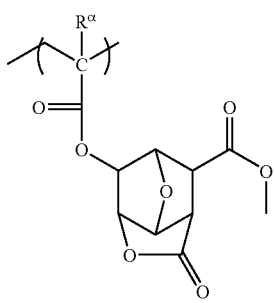

(a2-2-10)
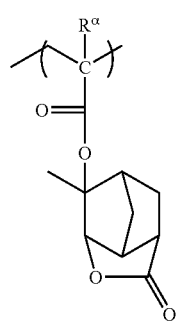
(a2-2-11)
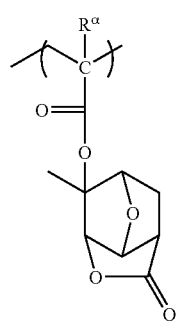
(a2-2-12)
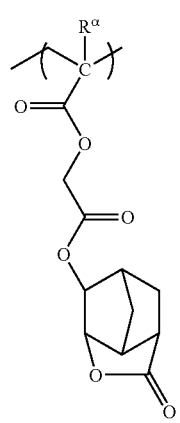
(a2-2-13)
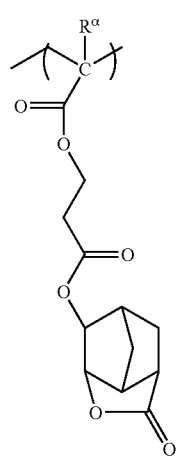
(a2-2-14)
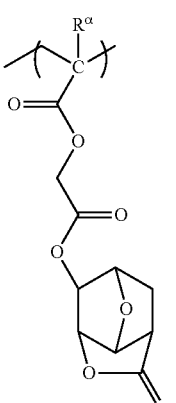
(a2-2-15)
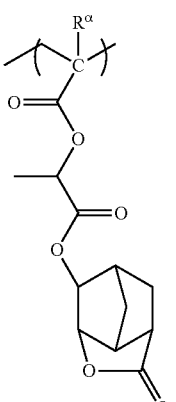
(a2-2-16)
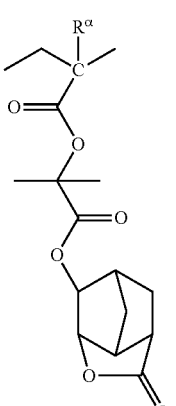
(a2-2-17)
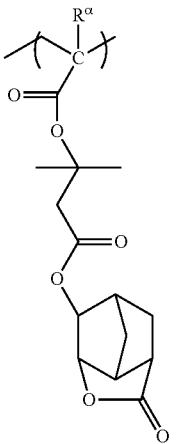

[Chemical Formula 38]
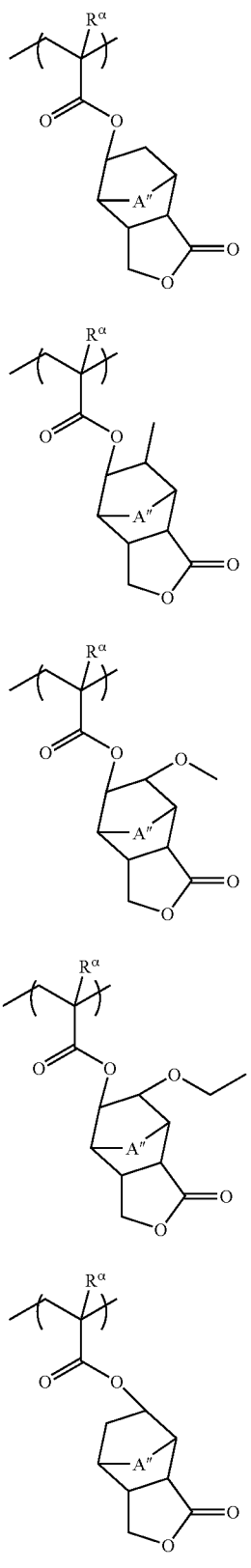
(a2-3-1)
(a2-3-2)
(a2-3-3)
(a2-3-4)
(a2-3-5)
[Chemical Formula 39]
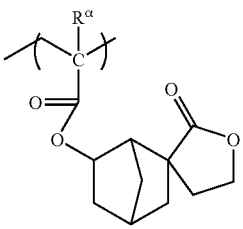
(a2-4-1)
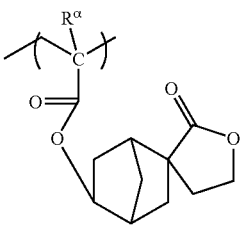
(a2-4-2)
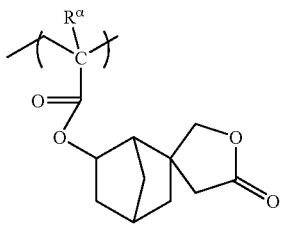
(a2-4-3)
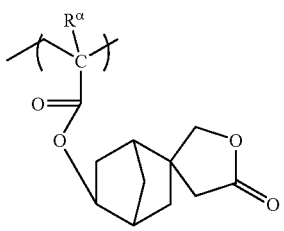
(a2-4-4)
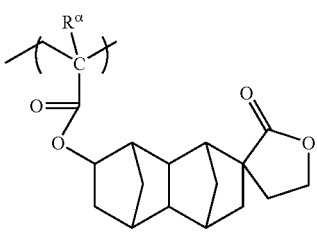
(a2-4-5)
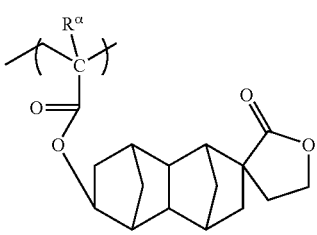
(a2-4-6)

(a2-4-7)
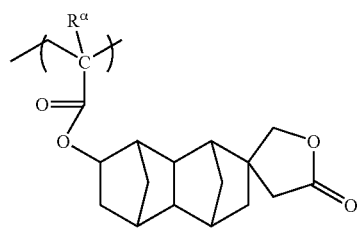
(a2-4-8)
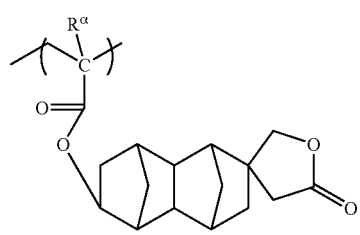
(a2-4-9)
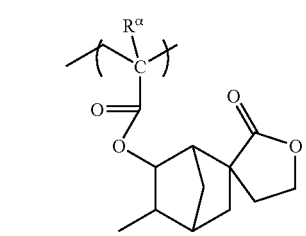
(a2-4-10)
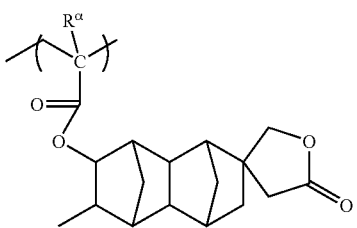
(a2-4-11)
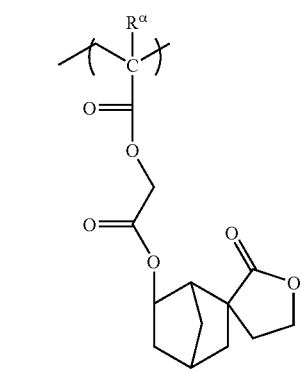
(a2-4-12)
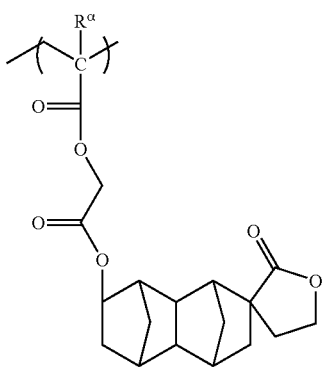
[Chemical Formula 40]
(a2-5-1)
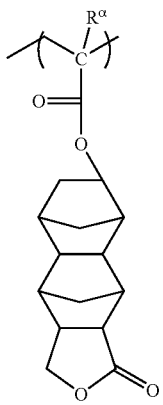
(a2-5-2)
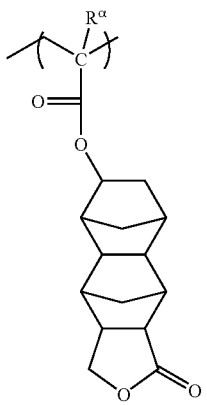
(a2-5-3)
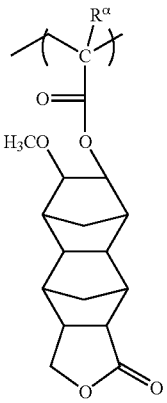

(a2-5-4)

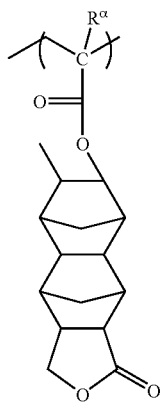

(a2-5-5)

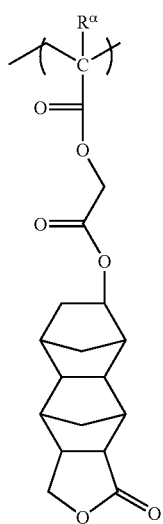

(a2-5-6)

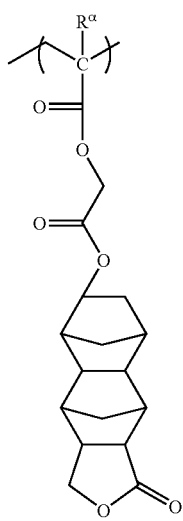

Also, when s" is 1, specific examples of the structural units represented by the above general formulae (a2-1) to (a2-5) when s" is 1 include groups in which —$CH_2$—C(=O)—O— is present between the oxygen atom (—O—) of the carbonyloxy group bonded to the carbon atom at the α-position and the lactone-containing cyclic group bonded to the oxygen atom in each of the formulae shown above.

As the structural unit (a2) in the polymeric compound (A0), one type of structural unit may be used, or two or more types may be used in combination.

In the present invention, the polymeric compound (A0) particularly preferably includes, as the structural unit (a2), at least one kind selected from the group consisting of structural units represented by the above general formula (a2-1) and structural units represented by the above general formula (a2-2).

The proportion of the structural unit (a2) in the polymeric compound (A0) is preferably 1 to 50 mol %, more preferably 5 to 50 mol %, and still more preferably 10 to 45 mol %, based on the combined total of all the structural units that constitute the polymeric compound (A0), because it excels in adhesion of the resist film formed by using the resist composition containing the polymeric compound (A0) with a substrate, and also excels in compatibility with a developing solution. Furthermore, when the proportion of the structural unit (a2) is not less than the lower limit in the above range, then the effect made by containing the structural unit (a2) can be sufficiently obtained. When the proportion is not more than the upper limit in the above range, a good quantitative balance with the other structural units can be attained.

Also, in the polymeric compound (A0), the total proportion of the structural units (a0) and (a2) is preferably 5 to 70 mol %, more preferably 10 to 70 mol %, still more preferably 15 to 70 mol %, and most preferably 20 to 70 mol %, based on the combined total of all the structural units that constitute the polymeric compound (A0), because it excels in various lithography properties. When the proportion is within the above range, mask error factor (MEF), critical dimension uniformity (CDU), and the resist pattern shape can be more excellent.

If the polymeric compound (A0) includes both of the structural unit (a0) and the structural unit (a2), the each proportion of the structural units (a0) and (a2) in the polymeric compound (A0) is the following. The proportion of the structural unit (a0) is preferably 1 to 40 mol %, more preferably 10 to 35 mol %, and most preferably 15 to 30 mol %. The proportion of the structural unit (a2) is preferably 1 to 45 mol %, more preferably 10 to 45 mol %, and most preferably 20 to 45 mol %.

Structural Unit (a4)

The structural unit (a4) is a structural unit derived from an acrylate ester which has a non-acid dissociable aliphatic polycyclic group. The expression "non-acid dissociable" means that a group does not dissociate under action of an acid.

Examples of the polycyclic group include the same groups as those described above in the structural unit (a1), and any of the multitude of conventional polycyclic groups used within the resin component of resist compositions for ArF excimer lasers, KrF excimer lasers or the like (and preferably for ArF excimer lasers) can be used.

In particular, at least one group selected from amongst a tricyclodecanyl group, an adamantyl group, a tetracyclododecanyl group, an isobornyl group, and a norbornyl group are preferable in terms of industrial availability and the like. These polycyclic groups may contain a linear or branched alkyl group of 1 to 5 carbon atoms as a substituent.

Specific examples of the structural unit (a4) include a structural unit represented by the general formulae (a4-1) to (a4-5) shown below.

[Chemical Formula 41]

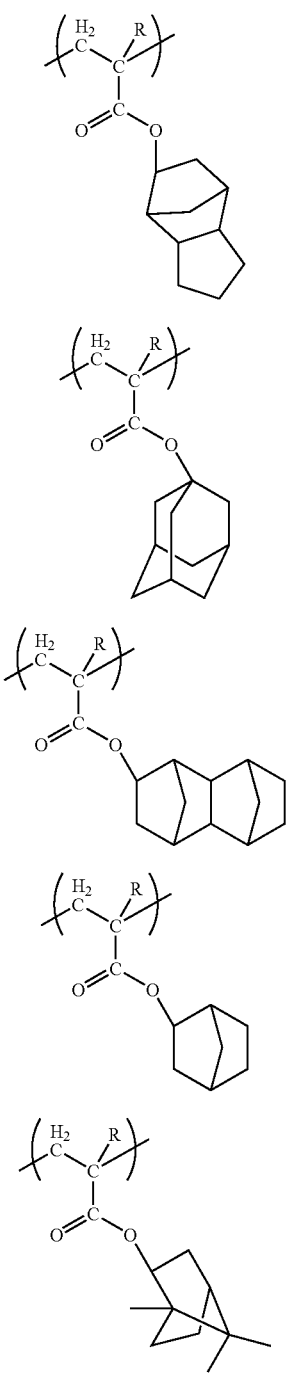

(In the formula, R is as defined above.)

If the structural unit (a4) is included in the polymeric compound (A0), the proportion of the structural unit (a4) is preferably 1 to 30 mol %, and more preferably 10 to 20 mol %, based on the combined total of all the structural units that constitute the polymer compound (A0).

Structural Unit (a5)

The structural unit (a5) is a structural unit represented by the above general formula (a0-1) in which $R^2$ is a bivalent hydrocarbon group which may contain a substituent.

The bivalent hydrocarbon group which may contain a substituent is the same as "(hydrocarbon group which may contain a substituent)" described above in the explanation of $R^2$.

The bivalent hydrocarbon group which may contain a substituent is preferably a linear or branched aliphatic hydrocarbon group or a cyclic aliphatic hydrocarbon group (bivalent aliphatic cyclic group). Of these, a linear or branched aliphatic hydrocarbon group is particularly preferable.

The linear or branched aliphatic hydrocarbon group preferably has 1 to 10 carbon atoms, more preferably 1 to 6 carbon atoms, still more preferably 1 to 4 carbon atoms, and most preferably 1 to 3 carbon atoms.

As the cyclic aliphatic hydrocarbon group (bivalent aliphatic cyclic group), groups in which two or more hydrogen atoms have been removed from cyclopentane, cyclohexane, norbornane, isobornane, adamantane, tricyclodecane or tetracyclododecane are particularly preferable.

The proportion of the structural unit (a5) in the polymeric compound (A0) is preferably from 1 to 30 mol %, more preferably from 5 to 25 mol %, and still more preferably from 5 to 15 mol %, based on the combined total of all the structural units that constitute the polymeric compound (A0). When this proportion is not less than the lower limit in the above range, then lithography properties such as resolution and pattern shape can be improved. When the proportion is not more than the upper limit in the above range, a good quantitative balance with the other structural units can be attained.

In the present invention, the component (A) includes the polymeric compound (A0) containing the structural unit (a0).

The component (A1) preferably includes a polymeric compound containing the structural unit (a0) and the structural unit (a1).

Examples of the polymeric compound containing the structural units (a0) and (a1) include a copolymer consisting of the structural units (a0) and (a1); a copolymer consisting of the structural units (a0), (a1) and (a3); a copolymer consisting of the structural units (a0), (a1) and (a2); a copolymer consisting of the structural units (a0), (a1), (a2) and (a3); and a copolymer consisting of the structural units (a0), (a1), (a2), (a3) and (a5).

There are no particular restrictions on the weight average molecular weight (Mw) (the polystyrene equivalent value determined by gel permeation chromatography (GPC), hereinafter defined as the same) of the polymeric compound (A0), although the weight average molecular weight of the polymeric compound (A0) is preferably 2,000 to 50,000, more preferably 3,000 to 30,000, and most preferably 4,000 to 20,000. Ensuring that the weight average molecular weight of the polymeric compound (A0) is not more than the upper limit, solubility sufficient for a resist relative to a resist solvent can be obtained. Ensuring that the weight average molecular weight of the polymeric compound (A0) is not less than the lower limit, excellent dry-etching resistance and excellent cross-sectional shape of the resist pattern can be obtained.

Further, the dispersity (Mw/Mn) is preferably within a range from 1.0 to 5.0, more preferably from 1.0 to 3.0, and most preferably from 1.2 to 2.5. Herein, Mn means the number average molecular weight.

As the polymeric compound (A0) in the component (A1), one kind may be used alone, or two or more kinds may be used in combination.

The proportion of the polymeric compound (A0) in the component (A1) is preferably at least 25% by weight, more preferably at least 50% by weight, still more preferably at least 75% by weight, and may be 100% by weight. When the proportion of the polymeric compound (A0) is at least 25% by weight, the resolution can be further improved. Also, lithography properties and the like can be further improved.

The polymeric compound (A0) can be obtained, for example, by a conventional radical polymerization or the like of the monomers corresponding with each of the structural units, using a radical polymerization initiator such as azobisisobutyronitrile (AIBN).

Also, in the polymeric compound (A0), by using a chain transfer agent such as HS—$CH_2$—$CH_2$—$CH_2$—$C(CF_3)_2$—OH during the above polymerization, a —$C(CF_3)_2$—OH group may be introduced at the terminals of the polymeric compound (A0). When a hydroxyalkyl group in which a part of the hydrogen atoms of the alkyl group has been substituted with fluorine atoms is introduced into a copolymer in this manner, the copolymer thus obtained can have advantageous effects of reducing the levels of developing defects and LER (line edge roughness: unevenness of the line side walls of a line pattern).

The monomer which corresponds with each of the structural units may be a commercially available compound, or may be synthesized by using a conventional method.

As the component (A1), the polymeric compound (A0) and a resin component other than the polymeric compound (A0) may be used together.

There are no particular restrictions on the resin component other than the polymeric compound (A0), and any of the multitude of conventional resin components used for chemically-amplified positive resist composition (for example, base resins for ArF excimer lasers or KrF excimer lasers (and preferably for ArF excimer lasers)), arbitrarily selected, can be used. Examples of the base resin for ArF excimer lasers include those which contain the aforementioned structural unit (a1) as an indispensable structural unit, and arbitrarily further contains the aforementioned structural units (a2) to (a4).

[Component (A2)]

In the resist composition of the present invention, it is preferable that the component (A2) be a low molecular weight compound which has a molecular weight within the range of 500 to less than 2,000, and contains an acid dissociable, dissolution inhibiting group described above in the explanation of the structural unit (a1) and a hydrophilic group. Specific examples thereof include compounds in which a part of the hydrogen atoms of the hydroxyl groups within a compound containing a plurality of phenol skeletons have been substituted with an aforementioned acid dissociable, dissolution inhibiting group.

The component (A2) is preferably low molecular weight phenol compounds known as sensitizers or heat resistance improvement agents for non-chemically amplified g-line or i-line resists in which a part of the hydrogen atoms of the hydroxyl groups are substituted with the above acid dissociable, dissolution inhibiting group. The component (A2) can be used arbitrarily selected from those.

Examples of these low molecular weight phenol compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3', 4'-trihydroxyphenyl)propane, tris(4-hydroxyphenyl) methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, and 1-[1-(4-hydroxyphenyl)isopropyl]-4-[1,1-bis (4-hydroxyphenyl)ethyl]benzene; and dimers, trimers and tetramers of formalin condensation products of phenols such as phenol, m-cresol, p-cresol and xylenol. Of course, the low molecular weight phenol compounds are not restricted to these examples.

There is no particular restriction on the acid dissociable, dissolution inhibiting group, and examples thereof include those described above.

As the component (A2), one type may be used alone, or two or more types may be used in combination.

In the resist composition of the present invention, as the component (A), one kind can be used alone, or two or more kinds can be used in combination.

Of these, the component (A) preferably includes the component (A1).

In the resist composition of the present invention, the content of the component (A) may be adjusted according to the thickness of the resist film to be formed.

<Component (B)>

In the present invention, there are no particular restrictions on the component (B), and those which have been proposed as acid generators for conventional chemically-amplified resists can be used.

Examples of these acid generators are numerous, and include onium salt-based acid generators such as iodonium salts and sulfonium salts; oxime sulfonate-based acid generators; diazomethane-based acid generators such as bisalkyl or bisaryl sulfonyl diazomethanes and poly(bis-sulfonyl)diazomethanes; nitrobenzyl sulfonate-based acid generators; iminosulfonate-based acid generators; and disulfone-based acid generators.

As an onium salt-based acid generator, for example, an acid generator represented by the general formula (b-1) or (b-2) shown below can be used.

[Chemical Formula 42]

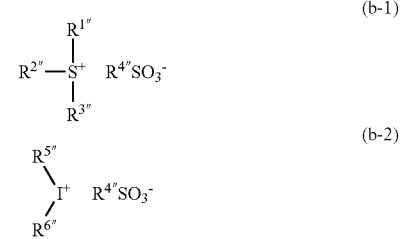

(In the formulae, $R^{1''}$ to $R^{3''}$, $R^{5''}$ and $R^{6''}$ each independently represents an aryl group or an alkyl group; two of $R^{1''}$ to $R^{3''}$ in the formula (b-1) may mutually be bonded to form a ring together with the sulfur atom in the formula; $R^{4''}$ represents an alkyl group which may contain a substituent, a halogenated alkyl group which may contain a substituent, an aryl group which may contain a substituent, or an alkenyl group which may contain a substituent; at least one of $R^{1''}$ to $R^{3''}$ represents an aryl group; and at least one of $R^{5''}$ and $R^{6''}$ represents an aryl group.)

In the general formula (b-1), $R^{1''}$ to $R^{3''}$ each independently represents an aryl group or an alkyl group. Here, two of $R^{1''}$ to $R^{3''}$ in the formula (b-1) may mutually be bonded to form a ring together with the sulfur atom in the formula.

Also, at least one of $R^{1\prime\prime\prime}$ to $R^{3\prime\prime\prime}$ represents an aryl group. Two or more of $R^{1\prime\prime\prime}$ to $R^{3\prime\prime\prime}$ are preferably aryl groups, and all of $R^{1\prime\prime\prime}$ to $R^{3\prime\prime\prime}$ are most preferably aryl groups.

There are no particular restrictions on the aryl group for $R^{1\prime\prime\prime}$ to $R^{3\prime\prime\prime}$. For example, the aryl group may be an aryl group of 6 to 20 carbon atoms, and a part of or all of the hydrogen atoms in the aryl group may or may not be substituted with alkyl groups, alkoxy groups, halogen atoms, hydroxyl groups or the like.

The aryl group is preferably an aryl group of 6 to 10 carbon atoms because it can be synthesized inexpensively. Specific examples thereof include a phenyl group and a naphthyl group.

In the aryl group, the alkyl group with which hydrogen atoms may be substituted is preferably an alkyl group of 1 to 5 carbon atoms, and most preferably a methyl group, an ethyl group, a propyl group, an n-butyl group, or a tert-butyl group.

In the aryl group, the alkoxy group with which hydrogen atoms may be substituted is preferably an alkoxy group of 1 to 5 carbon atoms, and more preferably a methoxy group, an ethoxy group, an n-propoxy group, an iso-propoxy group, an n-butoxy group, or a tert-butoxy group, and most preferably a methoxy group or an ethoxy group.

In the aryl group, the halogen atom with which hydrogen atoms may be substituted is preferably a fluorine atom.

There are no particular restrictions on the alkyl groups for $R^{1\prime\prime\prime}$ to $R^{3\prime\prime\prime}$. Examples thereof include a linear, branched, or cyclic alkyl group of 1 to 10 carbon atoms. The alkyl group preferably has 1 to 5 carbon atoms, in terms of excellent resolution. Specific examples include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group. Of these, a methyl group is preferable, because it excels in resolution, and can be synthesized inexpensively.

If two of $R^{1\prime\prime\prime}$ to $R^{3\prime\prime\prime}$ in the general formula (b-1) are mutually bonded to form a ring together with the sulfur atom in the formula, the ring including the sulfur atom preferably forms a 3 to 10-membered ring, and more preferably forms a 5 to 7-membered ring.

Also, if two of R'' to $R^{3\prime\prime\prime}$ in the general formula (b-1) are mutually bonded to form a ring together with the sulfur atom in the formula, the other of R'' to $R^{3\prime\prime\prime}$ is preferably an aryl group. As the aryl group, the same aryl groups as those for $R^{1\prime\prime\prime}$ to $R^{3\prime\prime\prime}$ can be used.

As the cation moiety of compounds represented by the formula (b-1), a cation moiety represented by the formulae (I-1-1) to (I-1-10) shown below can preferably be used. Of these, a cation moiety which contains a triphenylmethane skeleton, such as cation moieties represented by the formulae (I-1-1) to (I-1-8), is particularly preferable.

In the formulae (I-1-9) and (I-1-10), $R^9$ and $R^{10}$ each independently represents a phenyl group which may contain a substituent, a naphthyl group which may contain a substituent, an alkyl group of 1 to 5 carbon atoms, an alkoxy group of 1 to 5 carbon atoms, or a hydroxyl group.

u represents an integer of 1 to 3, and is most preferably 1 or 2.

[Chemical Formula 43]

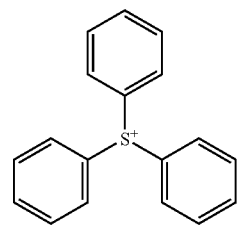

(I-1-1)

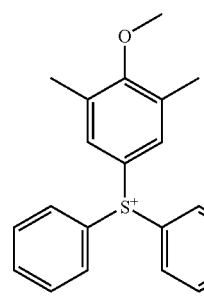

(I-1-2)

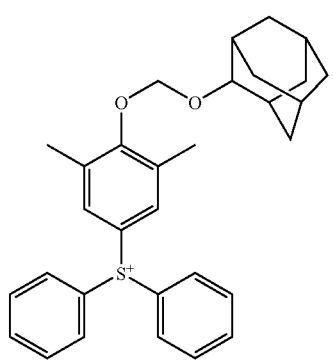

(I-1-3)

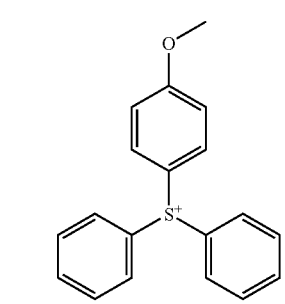

(I-1-4)

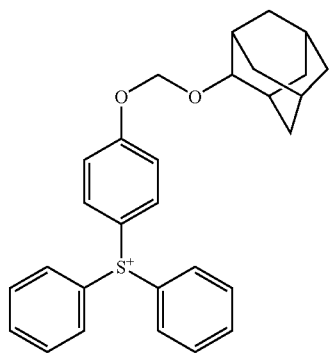

(I-1-5)

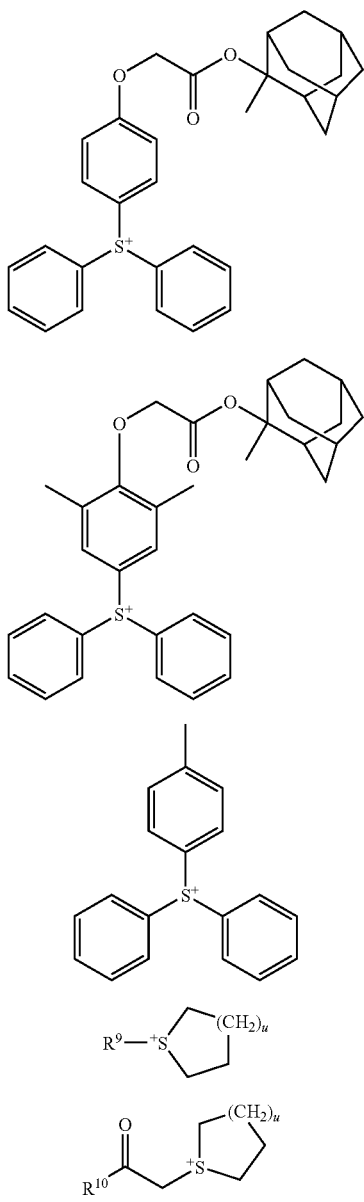

(I-1-6)
(I-1-7)
(I-1-8)
(I-1-9)
(I-1-10)

$R^{4\prime\prime}$ represents an alkyl group which may contain a substituent, a halogenated alkyl group which may contain a substituent, an aryl group which may contain a substituent, or an alkenyl group which may contain a substituent.

The alkyl group for $R^{4\prime\prime}$ may be linear, branched or cyclic.

The linear or branched alkyl group for $R^{4\prime\prime}$ preferably has 1 to 10 carbon atoms, more preferably 1 to 8 carbon atoms, and most preferably 1 to 4 carbon atoms.

The cyclic alkyl group for $R^{4\prime\prime}$ preferably has 4 to 15 carbon atoms, more preferably 4 to 10 carbon atoms, and most preferably 6 to 10 carbon atoms.

As the halogenated alkyl group for $R^{4\prime\prime}$, groups in which a part or all of the hydrogen atoms in the above linear, branched or cyclic alkyl group are substituted with halogen atoms can be used. Examples of the halogen atom include a fluorine atom, a chlorine atom, a bromine atom and iodine atom. Of these, a fluorine atom is preferable.

In the halogenated alkyl group, the proportion (halogenated ratio (%)) of the number of halogen atoms relative to the total number of halogen atoms and hydrogen atoms included in the halogenated alkyl group is preferably 10 to 100%, more preferably 50 to 100%, and most preferably 100%. Higher halogenated ratio is preferable because the strength of the acid increases.

The aryl group for $R^{4\prime\prime}$ is preferably an aryl group of 6 to 20 carbon atoms.

The alkenyl group for $R^{4\prime\prime}$ is preferably an alkenyl group of 2 to 10 carbon atoms.

In the aforementioned $R^{4\prime\prime}$, the expression "may contain a substituent" means that a part or all of the hydrogen atoms in the above linear, branched, or cyclic alkyl group, the halogenated alkyl group, the aryl group, or the alkenyl group may be substituted with substituents (atoms or groups other than hydrogen atoms).

The number of substituents in $R^{4\prime\prime}$ may be one, or may be two or more.

Examples of the substituent include a halogen atom, a hetero atom, an alkyl group, a group represented by the formula: $X-Q^1-$ (wherein, $Q^1$ represents a bivalent linking group containing an oxygen atom, and X represents a hydrocarbon group of 3 to 30 carbon atoms which may contain a substituent).

Examples of the halogen atom and alkyl group above include the same as those described above as halogen atoms in the halogenated alkyl group for $R^{4\prime\prime}$ and alkyl groups for $R^{4\prime\prime}$, respectively.

Examples of the hetero atom include an oxygen atom, a nitrogen atom, and a sulfur atom.

In the group represented by the formula: $X-Q^1-$, $Q^1$ represents a bivalent linking group containing an oxygen atom.

$Q^1$ may contain an atom other than an oxygen atom. Examples of the atom other than an oxygen atom include a carbon atom, a hydrogen atom, a sulfur atom, and a nitrogen atom.

Examples of the bivalent linking group containing an oxygen atom include: non-hydrocarbon-based oxygen atom-containing linking groups such as an oxygen atom (ether linkage; —O—), an ester linkage (—C(=O)—O—), an amide linkage (—C(=O)—NH—), a carbonyl group (—C(=O)—), and a carbonate linkage (—O—C(=O)—O—); and combined groups of the non-hydrocarbon-based oxygen-containing linking group with an alkylene group.

Examples of the above combined groups include —$R^{91}$—O—, —$R^{92}$—O—C(=O)—, and —C(=O)—O—$R^{93}$—O—C(=O)— (wherein, $R^{91}$ to $R^{93}$ each independently represents an alkylene group).

The alkylene group for $R^{91}$ to $R^{93}$ is preferably a linear or branched alkylene group, and preferably has 1 to 12 carbon atoms, more preferably 1 to 5 carbon atoms, and still more preferably 1 to 3 carbon atoms.

Specific examples of the alkylene group include a methylene group [—CH$_2$—]; an alkylmethylene group such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, or —C(CH$_2$CH$_3$)$_2$—; an ethylene group [—CH$_2$CH$_2$—]; an alkylethylene group such as —CH(CH$_3$)CH$_2$—, —CH(CH$_3$)CH(CH$_3$)—, —C(CH$_3$)$_2$CH$_2$—, or —CH(CH$_2$CH$_3$)CH$_2$—; a trimethylene group (n-propylene group) [—CH$_2$CH$_2$CH$_2$—]; an alkyltrimethylene group such as —CH(CH$_3$)CH$_2$CH$_2$— or —CH$_2$CH(CH$_3$)CH$_2$—; a tetramethylene group [—CH$_2$CH$_2$CH$_2$CH$_2$—]; an alkyltetramethylene group such as —CH(CH$_3$)CH$_2$CH$_2$CH$_2$— or —CH$_2$CH(CH$_3$)CH$_2$CH$_2$—; and a pentamethylene group [—CH$_2$CH$_2$CH$_2$CH$_2$CH$_2$—].

$Q^1$ is preferably a bivalent linking group containing an ester linkage or ether linkage, and more preferably —$R^{91}$—O—, —$R^{92}$—O—C(=O)—, or —C(=O)—O—$R^{93}$—O—C(=O)—.

In the group represented by the formula: "X-$Q^1$-", the hydrocarbon group for X may be an aromatic hydrocarbon group or an aliphatic hydrocarbon group.

The aromatic hydrocarbon group is a hydrocarbon group containing an aromatic ring. The aromatic hydrocarbon group preferably has 3 to 30 carbon atoms, more preferably 5 to 30 carbon atoms, still more preferably 5 to 20 carbon atoms, still more preferably 6 to 15 carbon atoms, and most preferably 6 to 12 carbon atoms. Here, the number of the carbon atoms described above does not include the number of carbon atoms within a substituent.

Specific examples of the aromatic hydrocarbon group include aryl groups in which one hydrogen atom has been removed from an aromatic hydrocarbon ring such as a phenyl group, a biphenyl group, a fluorenyl group, a naphthyl group, an anthryl group, and a phenanthryl group; and arylalkyl groups such as a benzyl group, a phenethyl group, a 1-naphthylmethyl group, a 2-naphthylmethyl group, a 1-naphthylethyl group, and a 2-naphthylethyl group. The number of carbon atoms of the alkyl chain in the arylalkyl group is preferably 1 to 4, more preferably 1 or 2, and still more preferably 1.

The aromatic hydrocarbon group may contain a substituent. For example, a part of carbon atoms which constitutes an aromatic ring included in the aromatic hydrocarbon group may be substituted with a hetero atom, or a part of hydrogen atoms bonded to an aromatic ring included in the aromatic hydrocarbon group may be substituted with a substituent.

Examples of the former case include a heteroaryl group in which a part of carbon atoms which constitutes the ring of the aryl group described above is substituted with a hetero atom such as an oxygen atom, a sulfur atom, or a nitrogen atom; and a heteroarylalkyl group in which a part of carbon atoms which constitutes the aromatic hydrocarbon ring of the arylalkyl group described above is substituted with the hetero atom.

On the other hand, examples of the substituents in the aromatic hydrocarbon group in the latter case include an alkyl group, an alkoxy group, a halogen atom, a halogenated alkyl group, a hydroxyl group, and an oxygen atom (=O).

The alkyl group for the substituent in the aromatic hydrocarbon group is preferably an alkyl group of 1 to 5 carbon atoms, and most preferably a methyl group, an ethyl group, a propyl group, an n-butyl group, or a tert-butyl group.

The alkoxy group for the substituent in the aromatic hydrocarbon group is preferably an alkoxy group of 1 to 5 carbon atoms, and more preferably a methoxy group, an ethoxy group, an n-propoxy group, an iso-propoxy group, an n-butoxy group, or a tert-butoxy group, and most preferably a methoxy group or an ethoxy group.

Examples of the halogen atom for the substituent in the aromatic hydrocarbon group include a fluorine atom, a chlorine atom, a bromine atom, and an iodine atom. Of these, a fluorine atom is preferable.

Examples of the halogenated alkyl group for the substituent in the aromatic hydrocarbon group include groups in which a part of or all of the hydrogen atoms of the above alkyl group are substituted with the halogen atoms.

The aliphatic hydrocarbon group for X may be a saturated aliphatic hydrocarbon group, or an unsaturated aliphatic hydrocarbon group. Also, the aliphatic hydrocarbon group may be linear, branched, or cyclic.

In the aliphatic hydrocarbon group for X, a part of carbon atoms which constitute the aliphatic hydrocarbon group may be substituted with a substituent containing a hetero atom, or a part or all of hydrogen atoms which constitute the aliphatic hydrocarbon group may be substituted with a substituent containing a hetero atom.

There are no particular restrictions on the "hetero atom" in X, as long as it is an atom other than a carbon atom and a hydrogen atom. Examples thereof include a halogen atom, an oxygen atom, a sulfur atom, and a nitrogen atom. Examples of the halogen atom include a fluorine atom, a chlorine atom, an iodine atom, and a bromine atom.

The substituent containing a hetero atom may be an atom consisting of the hetero atom, or a group containing a group or an atom other than the hetero atom.

As the substituents which are substituted for a part of carbon atoms which constitute the above aliphatic hydrocarbon group, for example, —O—, —(=O)—O—, —C(=O)—, —O—C(=O)—O—, —C(=O)—NH—, —NH— (wherein H may be substituted with a substitutent such as an alkyl group or an acyl group), —S—, —S(=O)$_2$—, or —S(=O)$_2$—O— can be used. If the aliphatic hydrocarbon group for X is cyclic, these substituents may be included in the ring structure.

Specific examples of the substituents which are substituted for a part or all of the hydrogen atoms include an alkoxy group, a halogen atom, a halogenated alkyl group, a hydroxyl group, an oxygen atom, and a cyano group.

The alkoxy group for the substituent is preferably an alkoxy group of 1 to 5 carbon atoms, more preferably a methoxy group, an ethoxy group, an n-propoxy group, an iso-propoxy group, an n-butoxy group, or a tert-butoxy group, and most preferably a methoxy group or an ethoxy group.

Examples of the halogen atom for the substituent include a fluorine atom, a chlorine atom, a bromine atom, and an iodine atom. Of these, a fluorine atom is preferable.

Examples of the halogenated alkyl group for the substituent include a group in which a part or all of the hydrogen atom in an alkyl group of 1 to 5 carbon atoms, such as a methyl group, an ethyl group, a propyl group, an n-propyl group, an n-butyl group, or a tert-butyl group, are substituted with the halogen atoms.

The aliphatic hydrocarbon group is preferably a linear or branched saturated hydrocarbon group, a linear or branched monovalent unsaturated hydrocarbon group, or a cyclic aliphatic hydrocarbon group (aliphatic cyclic group).

The linear saturated hydrocarbon group (alkyl group) preferably has 1 to 20 carbon atoms, more preferably 1 to 15 carbon atoms, and most preferably 1 to 10 carbon atoms. Specific examples thereof include a methyl group, an ethyl group, a propyl group, a butyl group, a pentyl group, a hexyl group, a heptyl group, an octyl group, a nonyl group, a decanyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group, and a docosyl group.

The branched saturated hydrocarbon group (alkyl group) has preferably 3 to 20 carbon atoms, more preferably 3 to 15 carbon atoms, and most preferably 3 to 10 carbon atoms. Specific examples thereof include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a 4-methylpentyl group.

The unsaturated hydrocarbon group has preferably 2 to 10 carbon atoms, more preferably 2 to 5 carbon atoms, still more preferably 2 to 4 carbon atoms, and most preferably 3 carbon atoms. Examples of the linear monovalent unsaturated hydrocarbon group include a vinyl group, a propenyl group (allyl group) and a butynyl group. Examples of the branched monovalent unsaturated hydrocarbon group include a 1-methylpropenyl group and a 2-methylpropenyl group.

Of these, the unsaturated hydrocarbon group is particularly preferably a propenyl group.

The aliphatic cyclic group may be a monocycle group or a polycyclic group. The aliphatic cyclic group preferably has 3 to 30 carbon atoms, more preferably 5 to 30 carbon atoms, still more preferably 5 to 20 carbon atoms, still more preferably 6 to 15 carbon atoms, and most preferably 6 to 12 carbon atoms.

Examples thereof include groups in which one or more of hydrogen atoms have been removed from a monocycloalkane; and groups in which one or more of hydrogen atoms have been removed from a polycycloalkane such as a bicycloalkane, a tricycloalkane, or a tetracycloalkane. Specific examples include groups in which at least one hydrogen atom has been removed from a monocycloalkane such as cyclopentane or cyclohexane; and groups in which at least one hydrogen atom has been removed from a polycycloalkane such as adamantane, norbornane, isobornane, tricyclodecane or tetracyclododecane.

If the aliphatic cyclic group does not contain a substituent containing a hetero atom in the ring structure, the aliphatic cyclic group is preferably a polycyclic group, more preferably groups in which one or more hydrogen atoms have been removed from a polycycloalkane, and most preferably groups in which one or more hydrogen atoms have been removed from an adamantane.

If the aliphatic cyclic group contains a substituent containing a hetero atom within the ring structure, the substituent containing a hetero atom is preferably —O—, —C(=O)—O—, —S—, —S(=O)$_2$—, or —S(=O)$_2$—O—. Specific examples of the aliphatic cyclic group include groups represented by the formula (L1) to (L5), and (S1) to (S4) shown below.

[Chemical Formula 44]

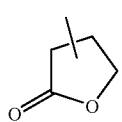

(L1)

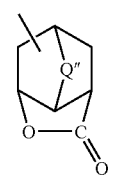

(L2)

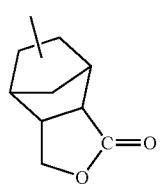

(L3)

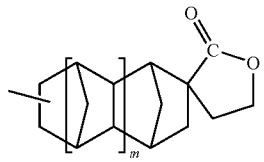

(L4)

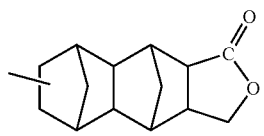

(L5)

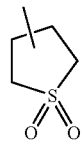

(S1)

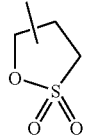

(S2)

(S3)

(S4)

(In the above formulae, Q″ represents an alkylene group of 1 to 5 carbon atoms, —O—, —S—, —O—R$^{94}$—, or —S—R$^{95}$—, wherein R$^{94}$ and R$^{95}$ each independently represents an alkylene group of 1 to 5 carbon atoms; and m represents an integer of 0 or 1.)

In the formulae, as each alkylene group for Q″, R$^{94}$, and R$^{95}$, the same alkylene groups as those for R$^{91}$ to R$^{93}$ above can be used.

These aliphatic cyclic group may be a group in which a part of hydrogen atoms bonded to the carbon atoms constituting the ring structure are substituted with substitutents. Examples of the substituent include an alkyl group, an alkoxy group, a halogen atom, a halogenated alkyl group, a hydroxyl group, and an oxygen atom (=O).

The alkyl group for the substituent is preferably an alkyl group of 1 to 5 carbon atoms, and particularly preferably a methyl group, an ethyl group, a propyl group, an n-butyl group, or a tert-butyl group.

Examples of the alkoxy group and halogen atoms for the substituent, respectively, include the same as those described above as the substitutents which are substituted for a part or all of hydrogen atoms.

Of these, X is preferably a cyclic group which may contain a substituent. The cyclic group may be an aromatic hydrocarbon group which may contain a substituent or an aliphatic cyclic group which may contain a substituent, and is preferably an aliphatic cyclic group which may contain a substituent.

The aforementioned aromatic hydrocarbon group is preferably a naphthyl group which may contain a substituent or a phenyl group which may contain a substituent.

The aliphatic cyclic group which may contain a substituent is preferably a polycyclic aliphatic cyclic group which may contain a substituent. The polycyclic aliphatic cyclic group is preferably a group in which one or more hydrogen atoms have been removed from a polycycloalkane, or a group represented by the above formulae (L2) to (L5), and (S3) to (S4).

Also, in the present invention, X is preferably a group containing a skeleton similar to $R^3$ in the structural unit (a0) of the component (A1), because lithography properties and the resist pattern shape can further be improved. Of these, a group containing a polar portion is particularly preferable.

Examples of the group containing a polar portion include groups in which a part of the carbon atoms constituting the aliphatic cyclic group for X are substituted with substituents containing a hetero atom, that is, —O—, —C(=O)—O—, —O—C(=O)—O—, —C(=O)—NH—, —NH— (wherein, H may be substituted with a substituent such as an alkyl group or an acyl group), —S—, —S(=O)$_2$—, —S(=O)$_2$—O—, or the like.

In the present invention, $R^{4''}$ preferably contains X-$Q^1$- as a substituent. In this case, $R^{4''}$ is preferably a group represented by the formula X-$Q^1$-$Y^3$— (wherein $Q^1$ and X are as defined above; and $Y^3$ represents an alkylene group of 1 to 4 carbon atoms which may contain a substituent, or a fluorinated alkylene group of 1 to 4 carbon atoms which may contain a substituent).

In the group represented by the formula X-$Q^1$-$Y^3$, examples of the alkylene group for $Y^3$ include the same alkylene groups as those described above for $Q^1$ in which the number of carbon atoms is 1 to 4.

As the fluorinated alkylene group for $Y^3$, groups in which a part or all of the hydrogen atoms in the above alkylene group are substituted with fluorine atoms can be used.

Specific examples of $Y^3$ include —CF$_2$—, —CF$_2$CF$_2$—, —CF$_2$CF$_2$CF$_2$—, —CF(CF$_3$)CF$_2$—, —CF(CF$_2$CF$_3$)—, —C(CF$_3$)$_2$—, —CF$_2$CF$_2$CF$_2$CF$_2$—, —CF(CF$_3$)CF$_2$CF$_2$—, —CF$_2$CF(CF$_3$)CF$_2$—, —CF(CF$_3$)CF(CF$_3$)—, —C(CF$_3$)$_2$CF$_2$—, —CF(CF$_2$CF$_3$)CF$_2$—, —CF(CF$_2$CF$_3$)—, and —C(CF$_3$)(CF$_2$CF$_3$)—; —CHF—, —CH$_2$CF$_2$—, —CH$_2$CH$_2$CF$_2$—, —CH$_2$CF$_2$CF$_2$—, —CH(CF$_3$)CH$_2$—, —CH(CF$_2$CF$_3$)—, —C(CH$_3$)(CF$_3$)—, —CH$_2$CH$_2$CH$_2$CF$_2$—, —CH$_2$CH$_2$CF$_2$CF$_2$—, —CH(CF$_3$)CH$_2$CH$_2$—, —CH$_2$CH(CF$_3$)CH$_2$—, —CH(CF$_3$)CH(CF$_3$)—, and —C(CF$_3$)$_2$CH$_2$—; and —CH$_2$—, —CH$_2$CH$_2$—, —CH$_2$CH$_2$CH$_2$—, —CH(CH$_3$)CH$_2$—, —CH(CH$_2$CH$_3$)—, —C(CH$_3$)$_2$—, —CH$_2$CH$_2$CH$_2$CH$_2$—, —CH(CH$_3$)CH$_2$CH$_2$—, —CH$_2$CH(CH$_3$)CH$_2$—, —CH(CH$_3$)CH(CH$_3$)—, —C(CH$_3$)$_2$CH$_2$—, —CH(CH$_2$CH$_3$)CH$_2$—, —CH(CH$_2$CH$_2$CH$_3$)—, and —C(CH$_3$)(CH$_2$CH$_3$)—.

$Y^3$ is preferably a fluorinated alkylene group, and particularly preferably a fluorinated alkylene group in which the carbon atom bonded to the adjacent sulfur atom is fluorinated. Examples of such fluorinated alkylene groups include —CF$_2$—, —CF$_2$CF$_2$—, —CF$_2$CF$_2$CF$_2$—, —CF(CF$_3$)CF$_2$—, —CF$_2$CF$_2$CF$_2$CF$_2$—, —CF(CF$_3$)CF$_2$CF$_2$—, —CF$_2$CF(CF$_3$)CF$_2$—, —CF(CF$_3$)CF(CF$_3$)—, —C(CF$_3$)$_2$CF$_2$—, and —CF(CF$_2$CF$_3$)CF$_2$—; —CH$_2$CF$_2$—, —CH$_2$CH$_2$CF$_2$—, and —CH$_2$CF$_2$CF$_2$—, —CH$_2$CH$_2$CH$_2$CF$_2$—, —CH$_2$CH$_2$CF$_2$CF$_2$—, and —CH$_2$CF$_2$CF$_2$CF$_2$—.

Of these, —CF$_2$—, —CF$_2$CF$_2$—, —CF$_2$CF$_2$CF$_2$—, or —CH$_2$CF$_2$CF$_2$— is preferable, —CF$_2$—, —CF$_2$CF$_2$—, or —CF$_2$CF$_2$CF$_2$— is more preferable, and —CF$_2$— is still more preferable.

The alkylene group or fluorinated alkylene group may contain a substituent. The expression that the alkylene group or fluorinated alkylene group "contain a substituent" means that a part or all of the hydrogen atoms or fluorine atoms in the alkylene group or fluorinated alkylene group are substituted with atoms or groups other than hydrogen atoms and fluorine atoms.

Examples of the substituent which may be included in the alkylene group or fluorinated alkylene group include an alkyl group of 1 to 4 carbon atoms, an alkoxy group of 1 to 4 carbon atoms, and hydroxyl group.

In the general formula (b-2), $R^{5''}$ and $R^{6''}$ each independently represents an aryl group or an alkyl group. At least one of $R^{5''}$ and $R^{6''}$ represents an aryl group. Both of $R^{5''}$ and $R^{6''}$ preferably represent aryl groups.

As the aryl groups for $R^{5''}$ and $R^{6''}$, the same aryl groups as those for $R^{1''}$ to $R^{3''}$ above can be used.

As the alkyl groups for $R^{5''}$ and $R^{6''}$, the same alkyl group as those for $R^{1''}$ to $R^{3''}$ can be used.

Of these, it is most preferable that both of $R^{5''}$ and $R^{6''}$ be phenyl groups.

$R^{4''}$ in the general formula (b-2) is the same as $R^{4''}$ in the general formula (b-1) shown above.

Specific examples of onium salt-based acid generators represented by formula (b-1) or (b-2) include diphenyliodonium trifluoromethanesulfonate or nonafluorobutanesulfonate; bis (4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

Also, onium salts in which the anion moiety of the above onium salts is substituted with an alkylsulfonate such as a methansulfonate, an n-propanesulfonate, an n-butanesulfonate, or an n-octanesulfonate can be used.

Also, onium salts in which the anion moiety of the above onium salts is substituted with one of anion moieties represented by formulae (b1) to (b8) shown below can be used.

[Chemical Formula 45]

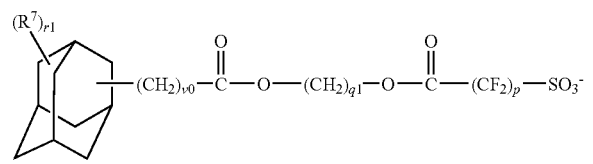

(b1)

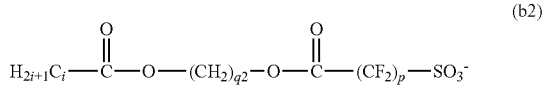

(b2)

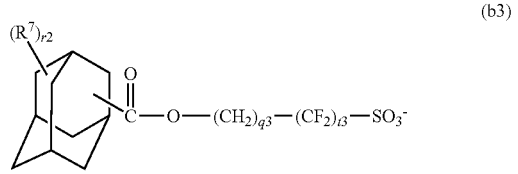

(b3)

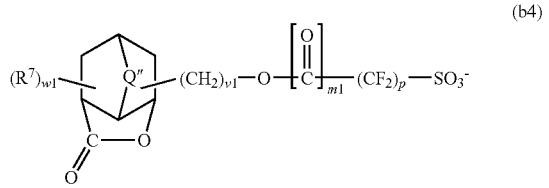

(b4)

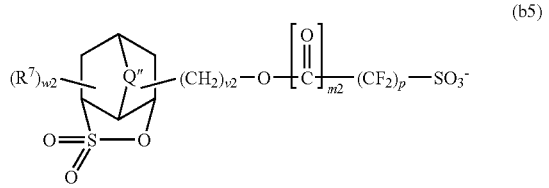

(b5)

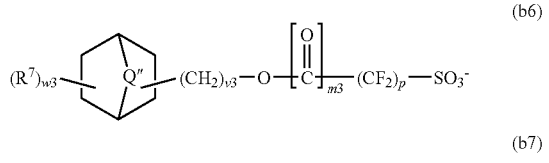

(b6)

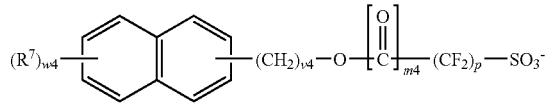

(b7)

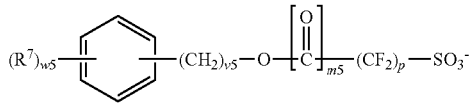

(b8)

(In the formulae, p represents an integer of 1 to 3; q1 to q2 each independently represents an integer of 1 to 5; q3 represents an integer of 1 to 12; t3 represents an integer of 1 to 3; r1 to r2 each independently represents an integer of 0 to 3; i represents an integer of 1 to 20; $R^7$ represents a substituent; m1 to m5 each independently represents an integer of 0 or 1; v0 to v5 each independently represents an integer of 0 to 3; w1 to w5 each independently represents an integer of 0 to 3; and Q" is as defined above.)

Examples of the substituent for $R^7$ include substituents which an aliphatic hydrocarbon group may contain or substituents which an aromatic hydrocarbon group may contain above in the explanation of X.

If each of the symbols (r1 to r2, and w1 to w5) attached at the bottom right of $R^7$ is an integer of 2 or more, then a plurality of $R^7$ in the compound may be the same as, or different from one another.

Further, an onium salt-based acid generator in which the anion moiety in the general formula (b-1) or (b-2) is substituted with an anion moiety represented by the general formula (b-3) or (b-4) shown below can also be used. Here, the cation moiety is the same as those described in the general formula (b-1) or (b-2).

[Chemical Formula 46]

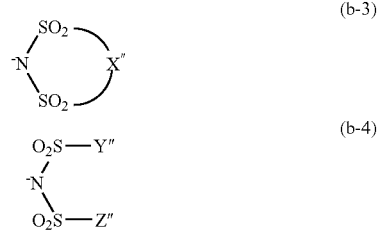

(In the formula, X" represents an alkylene group of 2 to 6 carbon atoms in which at least one hydrogen atom is substituted with a fluorine atom; and Y" and Z" each independently represents an alkyl group of 1 to 10 carbon atoms in which at least one hydrogen atom is substituted with a fluorine atom.)

X" represents a linear or branched alkylene group in which at least one hydrogen atom is substituted with a fluorine atom. The alkylene group for X" has 2 to 6 carbon atoms, preferably 3 to 5 carbon atoms, and most preferably 3 carbon atoms.

Y" and Z" each independently represents a linear or branched alkyl group in which at least one hydrogen atom is substituted with a fluorine atom. The alkyl group for Y" and Z" has 1 to 10 carbon atoms, preferably 1 to 7 carbon atoms, and more preferably 1 to 3 carbon atoms.

The smaller the number of carbon atoms of the alkylene group for X" or those of the alkyl group for Y" and Z" within the above-mentioned range of the number of carbon atoms, the more the solubility in a resist solvent is improved, and thus is consequently preferable.

Further, in the alkylene group for X" or the alkyl group for Y" and Z", it is preferable that the number of hydrogen atoms substituted with fluorine atoms be as large as possible, because the acid strength increases and the transparency to high energy radiation of 200 nm or less or electron beam is improved.

The proportion of fluorine atoms in the alkylene group or alkyl group, that is, the fluorination rate is preferably within the range of 70 to 100%, and more preferably within the range of 90 to 100%. A perfluoroalkylene group or a perfluoroalkyl group wherein all hydrogen atoms are substituted with fluorine atoms is most preferable.

Furthermore, a sulfonium salt that contains a cation moiety represented by the general formula (b-5) or (b-6) shown below can be used as an onium salt-based acid generator.

[Chemical Formula 47]

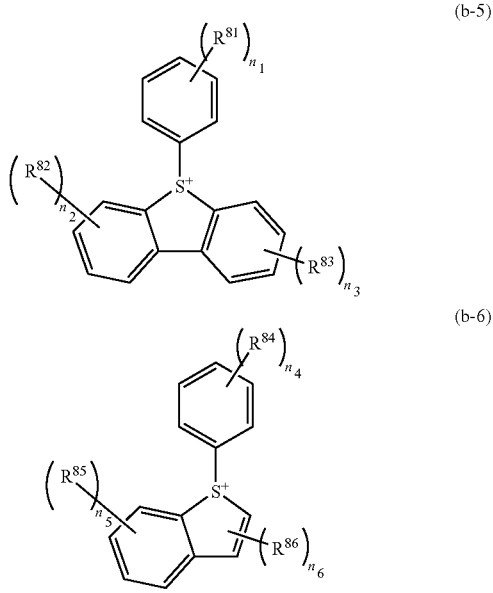

(In the formulae, $R^{81}$ to $R^{86}$ each independently represent an alkyl group, an acetyl group, an alkoxy group, a carboxyl group, a hydroxyl group or a hydroxyalkyl group; $n_1$ to $n_5$ each independently represent an integer of 0 to 3; and $n_6$ represents an integer of 0 to 2.)

The alkyl group for $R^{81}$ to $R^{86}$ is preferably an alkyl group of 1 to 5 carbon atoms, more preferably a linear or branched alkyl group, and particularly preferably a methyl group, an ethyl group, a propyl group, an isopropyl group, an n-butyl group, or a tert-butyl group.

The alkoxy group for $R^{81}$ to $R^{86}$ is preferably an alkoxy group of 1 to 5 carbon atoms, more preferably a linear or branched alkoxy group, and particularly preferably a methoxy group or an ethoxy group.

The hydroxyalkyl group for $R^{81}$ to $R^{86}$ in the formulae (b-5) and (b-6) is preferably a group in which one or more hydrogen atoms of the alkyl group described above are substituted with hydroxyl groups, and examples thereof include a hydroxymethyl group, a hydroxyethyl group, and a hydroxypropyl group.

When the subscripts $n_1$ to $n_6$ attached at the bottom right of $R^{81}$ to $R^{86}$ represent an integer of 2 or more, a plurality of $R^{81}$ to $R^{86}$ may be the same as or different from one another.

$n_1$ is preferably 0 to 2, more preferably 0 or 1, and still more preferably 0.

It is preferable that $n_2$ and $n_3$ each be independently 0 or 1, and it is more preferable that they be 0.

$n_4$ is preferably 0 to 2, and more preferably 0 or 1.
$n_5$ is preferably 0 or 1, and more preferably 0.
$n_6$ is preferably 0 or 1, and more preferably 1.

There are no particular restrictions on an anion moiety of a sulfonium salt that contains the cation moiety represented by the general formula (b-5) or (b-6), and anion moieties for onium salt-based acid generators which have been proposed may be used as the anion moieties. Examples of the anion moieties include a fluorinated alkylsulfonate ion such as the anion moiety ($R^{4"}SO_3^-$) of the onium salt-based acid generator represented by the general formula (b-1) or (b-2); and an anion moiety represented by the above general formula (b-3) or (b-4).

In the present description, the term "oxime sulfonate-based acid generator" means a compound which has at least one of the groups represented by the general formula (B-1) shown below, and has a property that generates an acid upon exposure to radiation. These kinds of oxime sulfonate-based acid generators are widely used for a chemically-amplified resist composition, so any oxime sulfonate-based acid generator, arbitrarily selected from these, can be used.

[Chemical Formula 48]

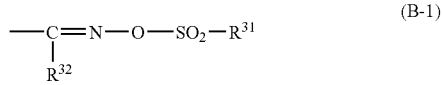

In the general formula (B-1), $R^{31}$ and $R^{32}$ each independently represents an organic group.)

The organic group for $R^{31}$ and $R^{32}$ is a group containing carbon atoms, and may further contain atoms other than carbon atoms (for example, a hydrogen atom, an oxygen atom, a nitrogen atom, a sulfur atom or a halogen atom (a fluorine atom, a chlorine atom or the like)).

The organic group for $R^{31}$ is preferably a linear, branched or cyclic alkyl group or an aryl group. The alkyl group or aryl group may contain a substituent. There are no particular restrictions on the substituent, and examples thereof include a fluorine atom, and a linear, branched or cyclic alkyl group of 1 to 6 carbon atoms. Here, the expression "containing a substituent" means that a part or all of the hydrogen atoms in the alkyl group or aryl group are substituted with substituents.

The alkyl group as the organic group for $R^{31}$ preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. The alkyl group for $R^{31}$ is particularly preferably an alkyl group which is partially or completely halogenated (hereinafter, sometimes referred to as a halogenated alkyl group). Here, a partially halogenated alkyl group means an alkyl group in which a part of the hydrogen atoms are substituted with halogen atoms, and a completely halogenated alkyl group represents an alkyl group in which all of the hydrogen atoms are substituted with halogen atoms. Examples of the halogen atoms include a fluorine atom, a chlorine atom, a bromine atom and an iodine atom. Of these, a fluorine atom is preferable. That is, the halogenated alkyl group is preferably a fluorinated alkyl group.

The aryl group as the organic group for $R^{31}$ preferably has 4 to 20 carbon atoms, more preferably 4 to 10 carbon atoms, and most preferably 6 to 10 carbon atoms. The aryl group as the organic group for $R^{31}$ is particularly preferably an aryl group which is partially or completely halogenated. Here, a partially halogenated aryl group means an aryl group in which a part of the hydrogen atoms are substituted with halogen atoms, and a completely halogenated aryl group means an aryl group in which all of the hydrogen atoms are substituted with halogen atoms.

$R^{31}$ is particularly preferably an alkyl group of 1 to 4 carbon atoms containing no substituent, or a fluorinated alkyl group of 1 to 4 carbon atoms.

The organic group for $R^{32}$ is preferably a linear, branched or cyclic alkyl group, an aryl group, or a cyano group. As the alkyl group or the aryl group for $R^{32}$, the same alkyl groups or aryl groups as those described above for $R^{31}$ can be used.

$R^{32}$ is particularly preferably a cyano group, an alkyl group of 1 to 8 carbon atoms containing no substituent, or a fluorinated alkyl group of 1 to 8 carbon atoms.

Preferred examples of the oxime sulfonate-based acid generator include compounds represented by the general formula (B-2) or (B-3) shown below.

[Chemical Formula 49]

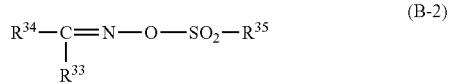

(B-2)

(In the general formula (B-2), $R^{33}$ represents a cyano group, an alkyl group containing no substituent, or a halogenated alkyl group; $R^{34}$ represents an aryl group; and $R^{35}$ represents an alkyl group containing no substituent or a halogenated alkyl group.)

[Chemical Formula 50]

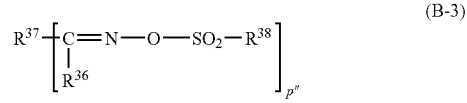

(B-3)

(In the formula (B-3), $R^{36}$ represents a cyano group, an alkyl group containing no substituent, or a halogenated alkyl group; $R^{37}$ represents a bivalent or trivalent aromatic hydrocarbon group; $R^{38}$ represents an alkyl group containing no substituent or a halogenated alkyl group; and p" represents an integer of 2 or 3.)

In the general formula (B-2), the alkyl group containing no substituent or the halogenated alkyl group for $R^{33}$ preferably has 1 to 10 carbon atoms, more preferably 1 to 8 carbon atoms, and most preferably 1 to 6 carbon atoms.

$R^{33}$ is preferably a halogenated alkyl group, and more preferably a fluorinated alkyl group.

The fluorinated alkyl group for $R^{33}$ is preferably a group in which 50% or more of the hydrogen atoms in the alkyl group are fluorinated, more preferably a group in which 70% or more of the hydrogen atoms in the alkyl group are fluorinated, and still more preferably a group in which 90% or more of the hydrogen atoms in the alkyl group are fluorinated.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenanthryl group; and heteroaryl groups in which a part of the carbon atoms which constitute the rings of these groups are substituted with heteroatoms such as an oxygen atom, a sulfur atom, and a nitrogen atom. Of these, a fluorenyl group is preferable.

The aryl group for $R^{34}$ may contain a substituent such as an alkyl group of 1 to 10 carbon atoms, a halogenated alkyl group of 1 to 10 carbon atoms or an alkoxy group of 1 to 10 carbon atoms. The alkyl group or halogenated alkyl group for the aforementioned substituent preferably has 1 to 8 carbon atoms, and more preferably 1 to 4 carbon atoms. Also, the halogenated alkyl group for the substituent is preferably a fluorinated alkyl group.

The alkyl group containing no substituent or the halogenated alkyl group for $R^{35}$ preferably has 1 to 10 carbon atoms, more preferably 1 to 8 carbon atoms, and most preferably 1 to 6 carbon atoms.

$R^{35}$ is preferably a halogenated alkyl group, and more preferably a fluorinated alkyl group.

The fluorinated alkyl group for $R^{35}$ is preferably a group in which 50% or more of the hydrogen atoms in the alkyl group are fluorinated, more preferably a group in which 70% or more of the hydrogen atoms in the alkyl group are fluorinated, and still more preferably a group in which 90% or more of the hydrogen atoms in the alkyl group are fluorinated, because the strength of the generated acid increases. The fluorinated alkyl group for $R^{35}$ is most preferably a completely fluorinated alkyl group in which 100% of the hydrogen atoms are substituted with fluorine atoms.

In the general formula (B-3), as the alkyl group containing no substituent or the halogenated alkyl group for $R^{36}$, the same alkyl groups containing no substituent or halogenated alkyl groups as those described above for $R^{33}$ can be used.

Examples of the bivalent or trivalent aromatic hydrocarbon group for $R^{37}$ include aryl groups for $R^{34}$ in which one or two hydrogen atoms are further removed.

As the alkyl group containing no substituent or the halogenated alkyl group for $R^{38}$, the same alkyl groups containing no substituent or halogenated alkyl groups as those described above in $R^{35}$ can be used.

p" is preferably 2.

Specific examples of the oxime sulfonate-based acid generator include
α-(p-toluenesulfonyloxyimino)-benzylcyanide,
α-(p-chlorobenzenesulfonyloxyimino)-benzylcyanide,
α-(4-nitrobenzenesulfonyloxyimino)-benzylcyanide,
α-(4-nitro-2-trifluoromethylbenzenesulfonyloxyimino)-benzylcyanide,
α-(benzenesulfonyloxyimino)-4-chlorobenzylcyanide,
α-(benzenesulfonyloxyimino)-2,4-dichlorobenzylcyanide,
α-(benzenesulfonyloxyimino)-2,6-dichlorobenzylcyanide,
α-(benzenesulfonyloxyimino)-4-methoxybenzylcyanide,
α-(2-chlorobenzenesulfonyloxyimino)-4-methoxybenzylcyanide,
α-(benzenesulfonyloxyimino)-thien-2-ylacetonitrile,
α-(4-dodecylbenzenesulfonyloxyimino)-benzylcyanide,
α-[(p-toluenesulfonyloxyimino)-4-methoxyphenyl]acetonitrile,
α-[(dodecylbenzenesulfonyloxyimino)-4-methoxyphenyl] acetonitrile,
α-(tosyloxyimino)-4-thienylcyanide,
α-(methylsulfonyloxyimino)-1-cyclopentenylacetonitrile,
α-(methylsulfonyloxyimino)-1-cyclohexenylacetonitrile,
α-(methylsulfonyloxyimino)-1-cycloheptenylacetonitrile,
α-(methylsulfonyloxyimino)-1-cyclooctenylacetonitrile,
α-(trifluoromethylsulfonyloxyimino)-1-cyclopentenylacetonitrile,
α-(trifluoromethylsulfonyloxyimino)-cyclohexylacetonitrile,
α-(ethylsulfonyloxyimino)-ethylacetonitrile,
α-(propylsulfonyloxyimino)-propylacetonitrile,
α-(cyclohexylsulfonyloxyimino)-cyclopentylacetonitrile, α-(cyclohexylsulfonyloxyimino)-cyclohexylacetonitrile,
α-(cyclohexylsulfonyloxyimino)-1-cyclopentenylacetonitrile,
α-(ethylsulfonyloxyimino)-1-cyclopentenylacetonitrile,
α-(isopropylsulfonyloxyimino)-1-cyclopentenylacetonitrile,
α-(n-butylsulfonyloxyimino)-1-cyclopentenylacetonitile,
α-(ethylsulfonyloxyimino)-1-cyclohexenylacetonitrile,
α-(isopropylsulfonyloxyimino)-1-cyclohexenylacetonitrile,
α-(n-butylsulfonyloxyimino)-1-cyclohexenylacetonitrile,
α-(methylsulfonyloxyimino)-phenylacetonitrile,
α-(methylsulfonyloxyimino)-p-methoxyphenylacetonitrile,
α-(trifluoromethylsulfonyloxyimino)-phenylacetonitrile,
α-(trifluoromethylsulfonyloxyimino)-p-methoxyphenylacetonitrile,
α-(ethylsulfonyloxyimino)-p-methoxyphenylacetonitrile,
α-(propylsulfonyloxyimino)-p-methylphenylacetonitrile, and
α-(methylsulfonyloxyimino)-p-bromophenylacetonitrile.

Also, oxime sulfonate-based acid generators disclosed in Japanese Unexamined Patent Application, First Publication No. Hei9-208554 ([Formula 18] and [Formula 19] in paragraphs [0012] to [0014]), and International Publication WO 2004/074242 (Examples 1 to 40 on pages 65 to 85) can be preferably used.

Further, suitable examples thereof include the following.

[Chemical Formula 51]

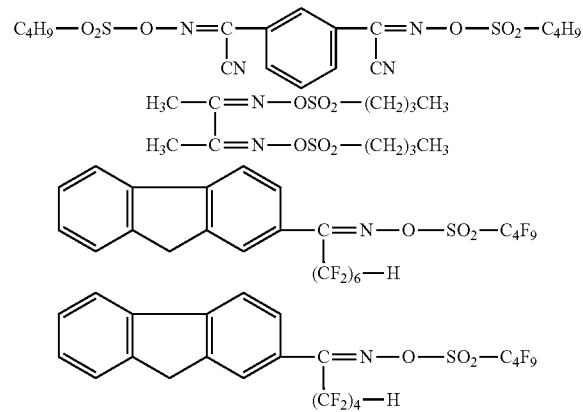

Among the diazomethane-based acid generators, specific examples of bisalkyl- or bisarylsulfonyldiazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Also, diazomethane-based acid generators disclosed in Japanese Unexamined Patent Application, First Publication No. Hei11-035551, Japanese Unexamined Patent Application, First Publication No. Hei11-035552, and Japanese Unexamined Patent Application, First Publication No. Hei11-035573 can be preferably used.

Examples of the poly(bissulfonyl)diazomethanes include 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, which are disclosed in Japanese Unexamined Patent Application, First Publication No. Hei11-322707.

As the component (B), one kind selected from the above acid generators may be used alone, or two or more kinds may be used in combination.

In the present invention, of these, onium salt-based acid generators with a fluorinated alkylsulfonate ion as the anion moiety are preferably used as the component (B).

The amount of the component (B) within the resist composition of the present invention is preferably 0.5 to 50 parts by weight, and more preferably 1 to 40 parts by weight, relative to 100 parts by weight of the component (A). When the amount is within the range, a pattern can be sufficiently formed. Also, a uniform solution and excellent storage stability can be obtained. Therefore, an amount within the above range is preferable.

<Optional Components>
[Component (D)]

The resist composition of the present invention preferably further includes a nitrogen-containing organic compound component (D) (hereinafter, referred to as "component (D)") as an optional component.

As the component (D), there are no particular limitations as long as it functions as an acid diffusion control agent, i.e., a quencher which traps the acid generated from the component (B) upon exposure. Since a multitude of these components (D) have already been proposed, any of these known compounds can be arbitrarily used. Of these, an aliphatic amine, particularly a secondary aliphatic amine or tertiary aliphatic amine is preferred.

Here, the aliphatic amine means an amine containing at least one aliphatic group, and the aliphatic group preferably has 1 to 20 carbon atoms.

Examples of the aliphatic amine include an amine (alkylamine or alkylalcoholamine) wherein at least one of the hydrogen atoms of $NH_3$ is substituted with an alkyl or hydroxyalkyl group having 20 or less carbon atoms; and a cyclic amine.

Specific examples of the alkylamines or alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-pentylamine, tri-n-hexylamine, tri-n-heptylamine, tri-n-octylamine, tri-n-nonylamine, tri-n-decanylamine, and tri-n-dodecylamine; and alkylalcoholamines such as diethanolamine, triethanolamine, diisopropanolamine, triisopropanolamine, di-n-octanolamine, tri-n-octanolamine, stearyl diethanolamine, and lauryl diethanolamine. Of these, a trialkylamine and/or an alkylalcoholamine is/are preferable.

Examples of the cyclic amine include a heterocyclic compound containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amines include piperidine and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetrarmine, and 1,4-diazabicyclo[2.2.2]octane.

Examples of the aromatic amine include aniline, pyridine, 4-dimethylaminopyridine, pyrol, indole, pyrazole, and imidazole, and derivatives thereof; diphenylamine, triphenylamine, and tribenzylamine.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris {2-(1-methoxyethoxy)ethyl}amine, tris{2-(1-ethoxyethoxy)ethyl}amine, tris{2-(1-ethoxypropoxy)ethyl}amine and tris[2-{2-(2-hydroxyethoxy)ethoxy}ethyl] amine.

These may be used either alone, or in combination of two or more different compounds.

In the present invention, of these, it is preferable to use a trialkylamine as the component (D).

The component (D) is typically used in a quantity within the range of 0.01 to 5.0 parts by weight, relative to 100 parts by weight of the component (A). When the quantity is within the above range, the resist pattern shape, the post exposure stability of the latent image formed by the pattern-wise exposure of the resist layer, and the like are improved.

[Component (E)]

In the resist composition of the present invention, in order to prevent any deterioration in sensitivity, and improve the resist pattern shape and the post exposure stability of the latent image formed by the pattern-wise exposure of the resist layer, at least one compound (E) selected from the group consisting of organic carboxylic acids and phosphorus oxo acids or derivatives thereof (hereinafter, referred to as component (E)) can also be added as an optional component.

Suitable examples of organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly preferable.

Examples of phosphorus oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphate esters such as di-n-butyl phosphate and diphenyl phosphate.

Examples of phosphonic acid derivatives include phosphonate esters such as dimethyl phosphonate, di-n-butyl phosphonate, phenylphosphonic acid, diphenyl phosphonate and dibenzyl phosphonate.

Examples of phosphinic acid derivatives include phosphinic esters such as phenylphosphinic acid.

As the component (E), one type may be used alone, or two or more types may be used in combination.

As the component (E), an organic carboxylic acid is preferable, and salicylic acid is particularly preferable.

The component (E) is used in a quantity within the range of 0.01 to 5.0 parts by weight, relative to 100 parts by weight of the component (A).

In the resist composition of the present invention, if desired, additives having miscibility, for example, additive resins for improving performance of a resist film, surfactants for improving coatability, dissolution inhibitors, plasticizers, stabilizers, colorants, antihalation agents, and dyes can be appropriately added.

[Component (S)]

The resist composition of the present invention can be prepared by dissolving materials in an organic solvent (hereinafter, referred to as component (S)).

The component (S) may be an organic solvent which can dissolve the respective components used in the present invention to give a uniform solution, and one or more kinds of organic solvents can be used, appropriately selected from those which have been conventionally known as a solvent for a chemically-amplified resist.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols such as ethylene glycol, diethylene glycol, propylene glycol, dipropylene glycol; derivatives of the polyhydric alcohols, including compounds having ester bonds such as ethylene glycol monoacetate, diethylene glycol monoacetate, propylene glycol monoacetate and dipropylene glycol monoacetate, and compounds having ether bonds such as monoalkyl ethers (for example, monomethyl ether, monoethyl ether, monopropyl ether or monobutyl ether) and monophenyl ether of the above polyhydric alcohols or the above compounds having ester bonds (of these, propylene glycol monomethyl ether acetate (PGMEA) or propylene glycol monomethyl ether (PGME) is preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, ethyl ethoxypropionate; and aromatic organic solvents such as anisole, ethylbenzyl ether, cresylmethyl ether, diphenyl ether, dibenzyl ether, phenetole, butylphenyl ether, ethylbenzene, diethylbenzene, pentylbenzene, isopropylbenzene, toluene, xylene, cymene, and mesitylene.

These organic solvents may be used either alone, or may be used as a mixed solvent of two or more different solvents.

Of these, propylene glycol monomethyl ether acetate (PGMEA), propylene glycol monomethyl ether (PGME), or ethyl lactate (EL) is preferable.

Also, a mixed solvent obtained by mixing PGMEA and a polar solvent is preferable. The mixing ratio (mass ratio) of PGMEA to the polar solvent may be appropriately decided taking account of compatibility, and is preferably adjusted within the range of 1:9 to 9:1, and more preferably 2:8 to 8:2.

More specifically, in the case of using EL as the polar solvent, the mass ratio PGMEA:EL is preferably within the range of 1:9 to 9:1, and more preferably 2:8 to 8:2. Furthermore, in those cases of using PGME as the polar solvent, the mass ratio PGMEA:PGME is preferably within the range of 1:9 to 9:1, more preferably 2:8 to 8:2, and still more preferably 3:7 to 7:3.

Furthermore, as the component (S), mixed solvents of at least one of PGMEA and EL with γ-butyrolactone are also preferred. In such cases, the mass ratio of the former and latter components in the mixed solvents is preferably within a range from 70:30 to 95:5.

There are no particular restrictions on the quantity of the component (S), and the quantity should be set in accordance with the required coating film thickness within a concentration that enables favorable application of the solution to a substrate or the like. Typically, the quantity is set so that the solid fraction concentration within the resist composition falls within the range of 0.5 to 20% by weight, and preferably 1 to 15% by weight.

The resist composition and the polymeric compound (A0) included in the resist composition of the present invention is a novel composition/compound which has not been known conventionally.

According to the resist composition of the present invention, a resist pattern with high resolution can be formed. It is not clear why such effects can be attained, but it can be thought as one of the reasons that, since the structural unit (a0) has a bivalent linking group ($R^2$) containing a specific polar group within the relatively long side chain, and a cyclic group ($R^3$) containing —$SO_2$—, which is a polar group. at the terminal of the side chain, the compatibility of the polymeric compound (A0) and the component (B) is increased, and accordingly the distribution of the component (B) within the resist film becomes more uniform.

Furthermore, according to the resist composition of the present invention, a resist film having excellent adhesion can be formed on a support such as a substrate.

Moreover, according to the resist composition of the present invention, a resist pattern can be formed with favorable sensitivity and excellent mask reproducibility (for example, mask error factor (MEF)), and the shape of the resist pattern thus formed (for example, circularity of the holes of a hole pattern, rectangularity of a line and space pattern), the critical dimension uniformity (CDU), the line width roughness (LWR) and the like are also favorable.

The MEF is a parameter that indicates how faithfully mask patterns of differing sizes can be reproduced using the same exposure dose with fixed pitch and changing the mask size (namely, the mask reproducibility).

The LWR is a phenomenon in which the line width of a line pattern becomes uneven (non-uniform) when a resist pattern is formed using a resist composition, and improvement in the level of LWR becomes an important issue as pattern miniaturization progresses.

<<Method of Forming Resist Pattern >>

The second aspect of the present invention is a method of forming a resist pattern which includes: forming a resist film on a substrate using the resist composition of the first aspect of the present invention; exposing the resist film; and developing the resist film with an alkali to form a resist pattern.

The method of forming a resist pattern of the present invention can be performed, for example, in the following manner.

Firstly, the positive resist composition of the present invention is applied onto a substrate using a spinner or the like, and a prebake (post applied bake (PAB)) is conducted under temperature conditions of 80 to 150° C. for 40 to 120 seconds, preferably 60 to 90 seconds to form a resist film. Following selective exposure of the formed resist film, either by exposure through a mask pattern using an exposure apparatus such as an ArF exposure apparatus, an electron beam lithography apparatus or an EUV exposure apparatus, or by patterning via direct irradiation with an electron beam without using a mask pattern, post exposure baking (PEB) is conducted under temperature conditions of 80 to 150° C. for 40 to 120 seconds, preferably 60 to 90 seconds. Subsequently, a developing treatment is conducted using an alkali developing solution such as a 0.1 to 10% by mass aqueous solution of tetramethylammonium hydroxide (TMAH), preferably followed by rinsing with pure water, and drying. Also, according to circumstances, a bake treatment (post bake) may be conducted after the above developing treatment. In this manner, a resist pattern that is faithful to the mask pattern can be obtained.

The substrate is not specifically limited and a conventionally known substrate can be used. For example, substrates for electronic components, and such substrates having prescribed wiring patterns formed thereon can be used. Specific examples thereof include a silicon wafer; a substrate made of a metal such as copper, chromium, iron or aluminum; and a substrate made of glass. As materials for the wiring pattern, for example, copper, aluminum, nickel or gold can be used.

Further, as the substrate, any one of the above-mentioned substrates provided with an inorganic and/or organic film on the surface thereof may be used. As the inorganic film, an inorganic anti-reflection film (inorganic BARC) can be used. As the organic film, an organic anti-reflection film (organic BARC) can be used.

There are no particular restrictions on the wavelength used for the exposure, and the exposure can be conducted using radiation such as ArF excimer lasers, KrF excimer lasers, $F_2$ excimer lasers, extreme ultraviolet rays (EUV), vacuum ultraviolet rays (VUV), electron beams (EB), X-rays, or soft X-rays. The resist composition is effective for KrF excimer lasers, ArF excimer lasers, EB or EUV, and particularly effective for ArF excimer lasers.

The exposure of the resist film may be a usual exposure (dry exposure) conducted in air or an inactive gas such as nitrogen gas, or may be an immersion exposure (liquid immersion lithography).

Here, the immersion exposure method is a method in which the region between the resist film and the lens at the lowermost point of the exposure apparatus is pre-filled with a solvent (immersion solvent) that has a larger refractive index than the refractive index of air, and then, while maintaining such a condition, the exposure (immersion lithography) is conducted.

The immersion solvent is preferably a solvent that has a refractive index larger than the refractive index of air but smaller than the refractive index of the resist film used in the exposure process. There are no particular restrictions on the refractive index of the immersion solvent, as long as the solvent has a refractive index within the above range.

Examples of the solvent which has a refractive index larger than that of air but smaller than that of the resist film include water, a fluorine-based inactive liquid, a silicon-based solvent, and a hydrocarbon-based solvent.

Specific examples of the fluorine-based inactive liquid include a liquid which has a fluorine-based compound as a main component, such as $C_3HCl_2F_5$, $C_4F_9OCH_3$, $C_4F_9OC_2H_5$, and $C_5H_3F_7$. The fluorine-based inactive liquid preferably has a boiling point within the range of 70 to 180° C., and more preferably 80 to 160° C. If the fluorine-based inactive liquid has a boiling point within the above range, the solvent used for the immersion lithography can be removed by a convenient method after exposure, and is consequently preferable.

The fluorine-based inactive liquid is particularly preferably a perfluoroalkyl compound in which all hydrogen atoms of the alkyl groups are substituted with fluorine atoms. Examples of the perfluoroalkyl compounds include perfluoroalkylether compounds and perfluoroalkylamine compounds.

Specific examples of the perfluoroalkylether compounds include a perfluoro(2-butyl-tetrahydrofuran) (boiling point: 102° C.), and specific examples of the perfluoroalkylamine compounds include a perfluorotributylamine (boiling point: 174° C.).

As the immersion solvent, water is preferably used in terms of cost, safety, environmental friendliness, and versatility.

<<Polymeric Compound>>

The polymeric compound of third aspect of the present invention is a polymeric compound including a structural unit (a0) represented by the general formula (a0-1) shown below.

[Chemical Formula 52]

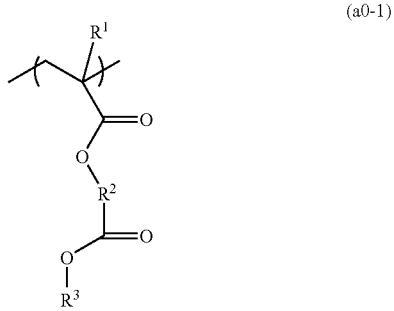

(a0-1)

(In the formula (a0-1), R¹ represents a hydrogen atom, a lower alkyl group of 1 to 5 carbon atoms, or a halogenated lower alkyl group of 1 to 5 carbon atoms; R² represents a bivalent linking group containing at least one kind of polar groups selected from the group consisting of —O—, —C(=O)—, —C(=O)—O—, a carbonate linkage (—O—C(=O)—O—), —S—, —S(=O)₂—, —S(=O)₂—O—, —NH—, —NR⁰⁴— (wherein, R⁰⁴ represents an alkyl group or an acyl group), and —NH—C(=O)—; and R³ represents a cyclic group containing a sulfonyl group within the ring skeleton.)

The explanation of the polymeric compound of the present invention is the same as the explanation of the polymeric compound (A0) in the resist composition of the present invention.

The polymeric compound of the present invention is a novel compound which has not been known.

The above polymeric compound is useful as a resin component for a resist composition, because a resist composition using the polymeric compound excels in resolution particularly in the formation of a fine resist pattern.

<<Compound>>

The compound of fourth aspect of the present invention is a compound represented by the general formula (a0″-1) shown below.

[Chemical Formula 53]

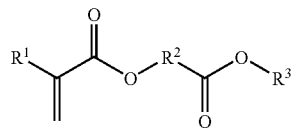

(a0″-1)

(In the formula (a0″-1), R¹ represents a hydrogen atom, a lower alkyl group of 1 to 5 carbon atoms, or a halogenated lower alkyl group of 1 to 5 carbon atoms; R² represents a bivalent linking group containing at least one kind of polar groups selected from the group consisting of —O—, —C(=O)—, —C(=O)—O—, a carbonate linkage (—O—C(=O)—O—), —S—, —S(=O)₂—, —S(=O)₂—O—, —NH—, —NR⁰⁴— (wherein, R⁰⁴ represents an alkyl group or an acyl group), and —NH—C(=O)—; and R³ represents a cyclic group containing a sulfonyl group within the ring skeleton.)

In the above formula (a0″-1), R¹ to R³ are respectively the same as the R¹ to R³ in the above formula (a0-1).

In the compound of the present invention, R³ in the above general formula (a0″-1) is preferably a cyclic group containing —O—SO₂— within the ring skeleton.

Also, R³ is preferably a cyclic group represented by the general formula (3-1) shown below.

[Chemical Formula 54]

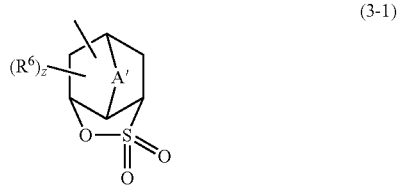

(3-1)

(In the formula (3-1), A' represents an oxygen atom, a sulfur atom, or an alkylene group of 1 to 5 carbon atoms which may contain an oxygen atom or a sulfur atom; z represents an integer of 0 to 2; R⁶ represents an alkyl group, an alkoxy group, a halogenated alkyl group, a hydroxyl group, —COOR″, —OC(=O)R″, a hydroxyalkyl group or a cyano group, wherein R″ represents a hydrogen atom or an alkyl group.)

In the above formula (3-1), A', z, R⁶ and R″ are respectively the same as A', z, R⁶ and R″ in the formula (3-1) above in the explanation of the structural unit (a0).

There are no particular restrictions on the manufacturing method of the compound of the present invention, and it can be manufactured by using a conventional method.

For example, a compound (X-2) represented by the general formula (X-2) shown below is added in the presence of a base to a solution in which a compound (X-1) represented by the general formula (X-1) shown below is dissolved in a reaction solvent, and then reacted, thereby obtaining the compound of the present invention.

Examples of the base include inorganic bases such as sodium hydroxide, K₂CO₃, and Cs₂CO₃; and organic bases such as triethylamine, 4-dimethylaminopyridine (DMAP), and pyridine. Examples of condensing agents include carbodiimide reagents such as ethyldiisopropylaminocarbodiimide (EDCI) hydrochloride, dicyclohexylcarboxylmide (DCC), diisopropylcarbodiimide and carbodiimidazole; tetraethyl pyrophosphate; and benzoniazole-N-hydroxytrisdimethylaminophosphonium hexafluorophosphide (Bop reagent).

Also, an acid may be used if necessary. As the acid, any acid generally used for dehydration/condensation may be used. Specific examples include inorganic acids such as hydrochloric acid, sulfuric acid and phosphoric acid; and organic acids such as methanesulfonic acid, trifluoromethanesulfonic acid, benzenesulfonic acid and p-toluenesulfonic acid. These acids may be used alone, or in a combination of two or more.

[Chemical Formula 55]

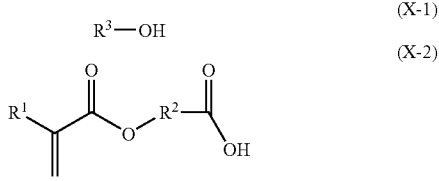

(X-1)
(X-2)

(In the formulae, R¹ to R³ are respectively as defined above.)

The structure of the compound thus obtained can be confirmed by a general organic analysis method such as a ¹H-NMR (nuclear magnetic resonance) spectrum method, a $^{13}$C-NMR spectrum method, a $^{19}$F-NMR spectrum method, an IR (infrared resonance) spectrum method, a MS (mass spectrometry) method, an element analysis, and an X-ray crystallographic analysis.

The compound of the present invention is a novel compound which has not been known.

Also, the compound of the present invention is a monomer which provides the structural unit (a0) constituting the above polymeric compound of the present invention.

EXAMPLES

Next, the present invention will be described in more detail with reference to examples, but the scope of the present invention is not limited to the following examples.

In the present examples, a compound represented by formula (1) is described as "compound (1)", and compounds represented by other formulae are described in the same manner.

<Synthesis of Compound (1)>

The compound (1) was synthesized according to the monomer synthesis example described below.

Example 1

Monomer Synthesis Example 1 Synthesis of Compound (1)

50 g of the precursor (1) shown below and 37.18 g of the alcohol (1) shown below are dissolved in 500 ml of tetrahydrofuran (THF) under a nitrogen atmosphere in a three-neck flask. Subsequently, 56.07 g of ethyldiisopropylaminocarbodiimide hydrochloride (EDCl/HCl) are added thereto. After the solution was cooled at 0° C., dimethylaminopyridine (DMAP) was added thereto, and the solution was reacted for 10 minutes. Thereafter, the solution was reacted for 12 hours at room temperature. After the reaction, 100 ml of water was added thereto, and the solution was concentrated under reduced pressure. Then, the organic phase obtained by extraction with ethyl acetate was washed with water. Subsequently, the organic phase obtained by extraction with ethyl acetate was washed three times with an aqueous solution of sodium hydrogen carbonate. Then, the organic phase obtained by extraction with ethyl acetate was washed with water. Subsequently, the organic phase obtained by extraction with ethyl acetate was washed twice with an aqueous solution of hydrochloric acid. Next, the organic phase obtained by extraction with ethyl acetate was washed three times with water.

Thereafter, the organic phase was concentrated under reduced pressure, washed twice with heptane, and then dried, thereby obtaining 58.10 g of the intended compound (1).

[Chemical Formula 56]

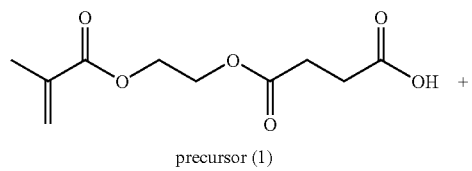

precursor (1)

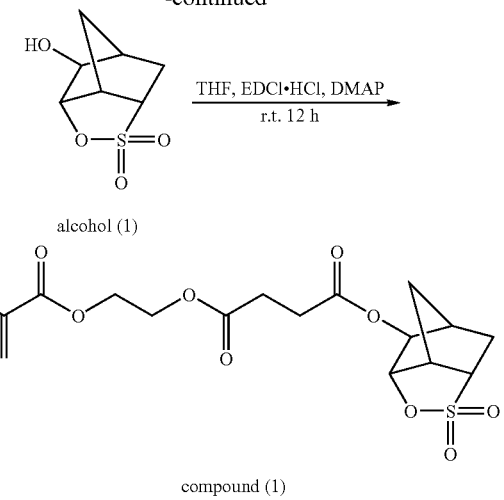

alcohol (1)

compound (1)

The results of instrumental analysis of the compound (1) thus obtained are as described below.

$^1$H-NMR: 6.12 (1H, a, s), 5.60 (1H, b, s), 4.73-4.71 (2H, c, m), 4.34 (4H, d, s), 3.55 (1H, e, m), 3.48 (1H, f, m), 2.68-2.57 (4H, g, m), 2.16-1.76 (5H, h, m), 1.93 (3H, i, s).

From the results described above, it was confirmed that the compound (1) had the structure shown below.

[Chemical Formula 57]

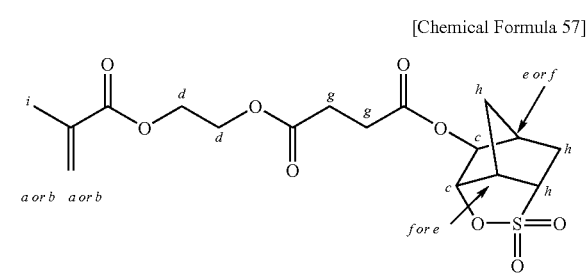

<Synthesis of Polymeric Compound (A0)>

The polymeric compounds 1 to 33 were synthesized according to the polymer synthesis examples described below.

Example 2

Polymer Synthesis Example 1

13.29 g (78.18 mmol) of the compound (2) shown below, 20.00 g (49.75 mmol) of the above compound (1), 19.86 g (75.81 mmol) of the compound (3) shown below, 5.57 g (33.17 mmol) of the compound (4) shown below, and 3.35 g (14.21 mmol) of the compound (5) shown below are dissolved in 91.53 g of methyl ethyl ketone (MEK) in a separable flask equipped with a thermometer, a reflux tube, and a nitrogen inlet tube. Then, 30.1 mmol of dimethyl azobis(isobutyrate) (V-601) as a radical polymerization initiator was added and dissolved in the resultant solution.

The reaction solution was dropwise added to 51.72 g of MEK heated at 80° C. for 3 hours under a nitrogen atmosphere. After the dropwise addition, the reaction solution was stirred whilst heating for 4 hours, and then cooled down at room temperature.

The reaction polymer solution thus obtained was dropwise added to a large amount of a mixed solution of normal-heptane/2-propanol, thereby precipitating a polymer. The precipitated white powder was separated by filtration, washed with a mixed solution of normal-heptane/2-propanol, washed with methanol, and then dried, thereby obtaining 40 g of the intended polymeric compound 1.

With respect to the polymeric compound 1, the weight average molecular weight (Mw) (the polystyrene equivalent value determined by gel permeation chromatography (GPC)) was 4,800, and the dispersity (Mw/Mn) was 1.46. Also, the copolymer composition ratio (proportion (molar ratio) of each structural unit within the constitutional formula) determined by carbon 13 nuclear magnetic resonance spectrum (600 MHz $^{13}$C-NMR) was "a21/a0/a11/a12/a3=39.2/24.3/15.8/14.1/6.6".

Examples 3 to 34

The polymeric compounds 2 to 33 were synthesized in the same manner as described above in [Polymer Synthesis Example 1], except that monomers which correspond with structural units constituting each polymeric compound and/or the proportions (molar ratio) of the monomers were changed.

With respect to each of the polymeric compounds 2 to 33, the reaction formula, the weight average molecular weight (Mw) (the polystyrene equivalent value determined by gel permeation chromatography (GPC)), the dispersity (Mw/Mn), and the copolymer composition ratio (the proportion (molar ratio) of each structural unit within the constitutional formula) determined by carbon 13 nuclear magnetic resonance spectrum (600 MHz $^3$C-NMR) are described below.

[Chemical Formula 58]

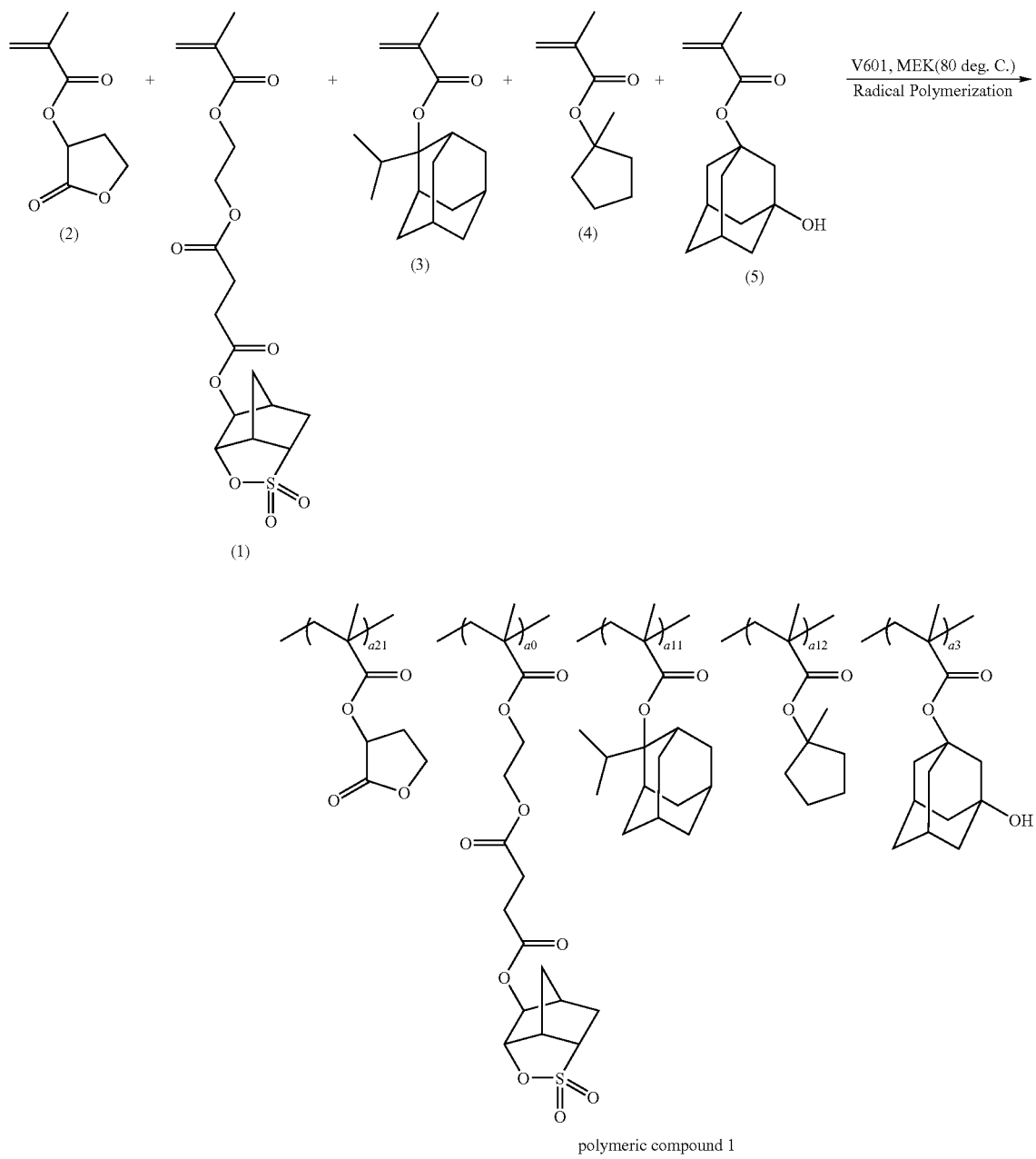

polymeric compound 1

Example 3
Polymer Synthesis Example 2
[Chemical Formula 59]
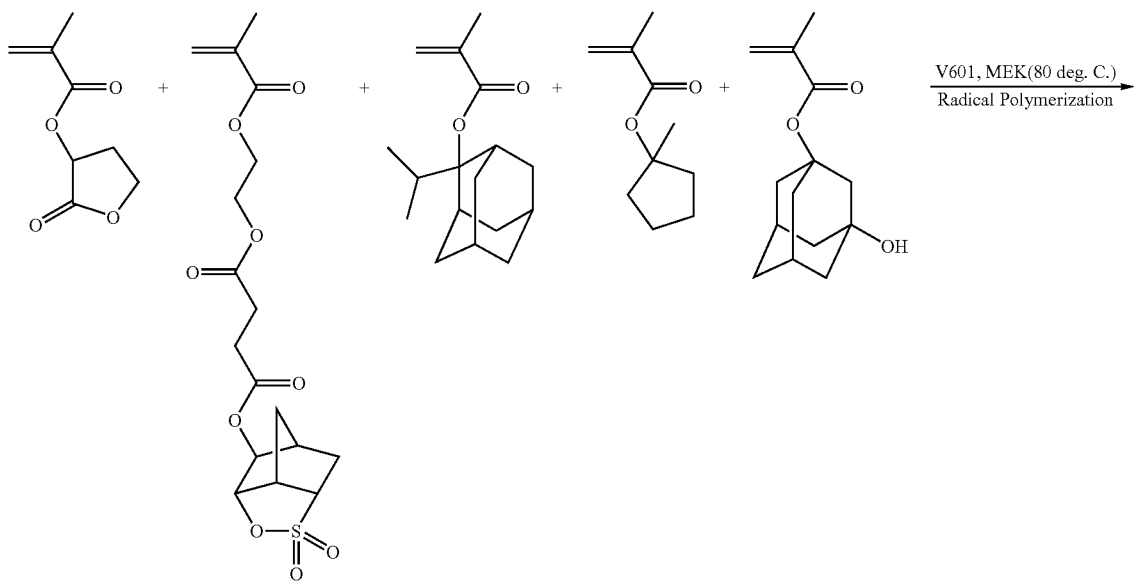
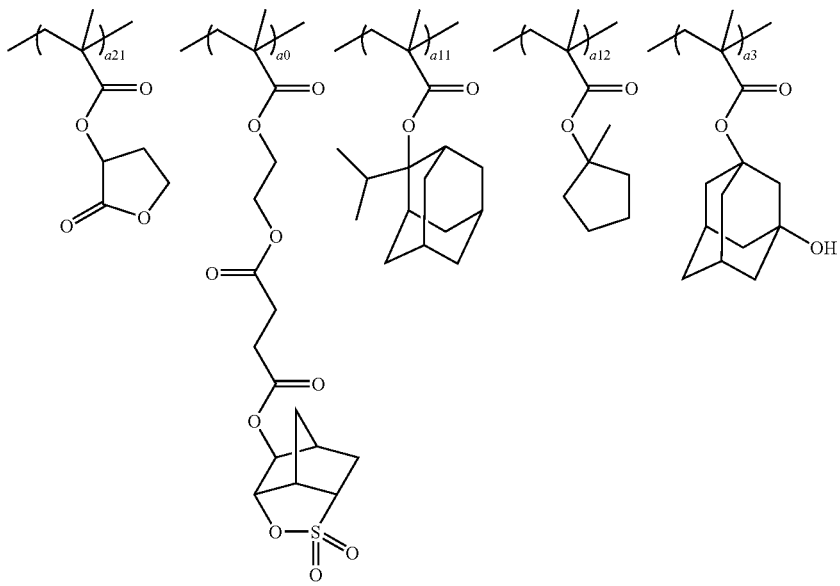
polymeric compound 2
[Mw = 6,000, Mw/Mn = 1.61; a21/a0/a11/a12/a3 = 25.8/20.0/20.1/14.5/19.6]

Example 4
Polymer Synthesis Example 3
[Chemical Formula 60]
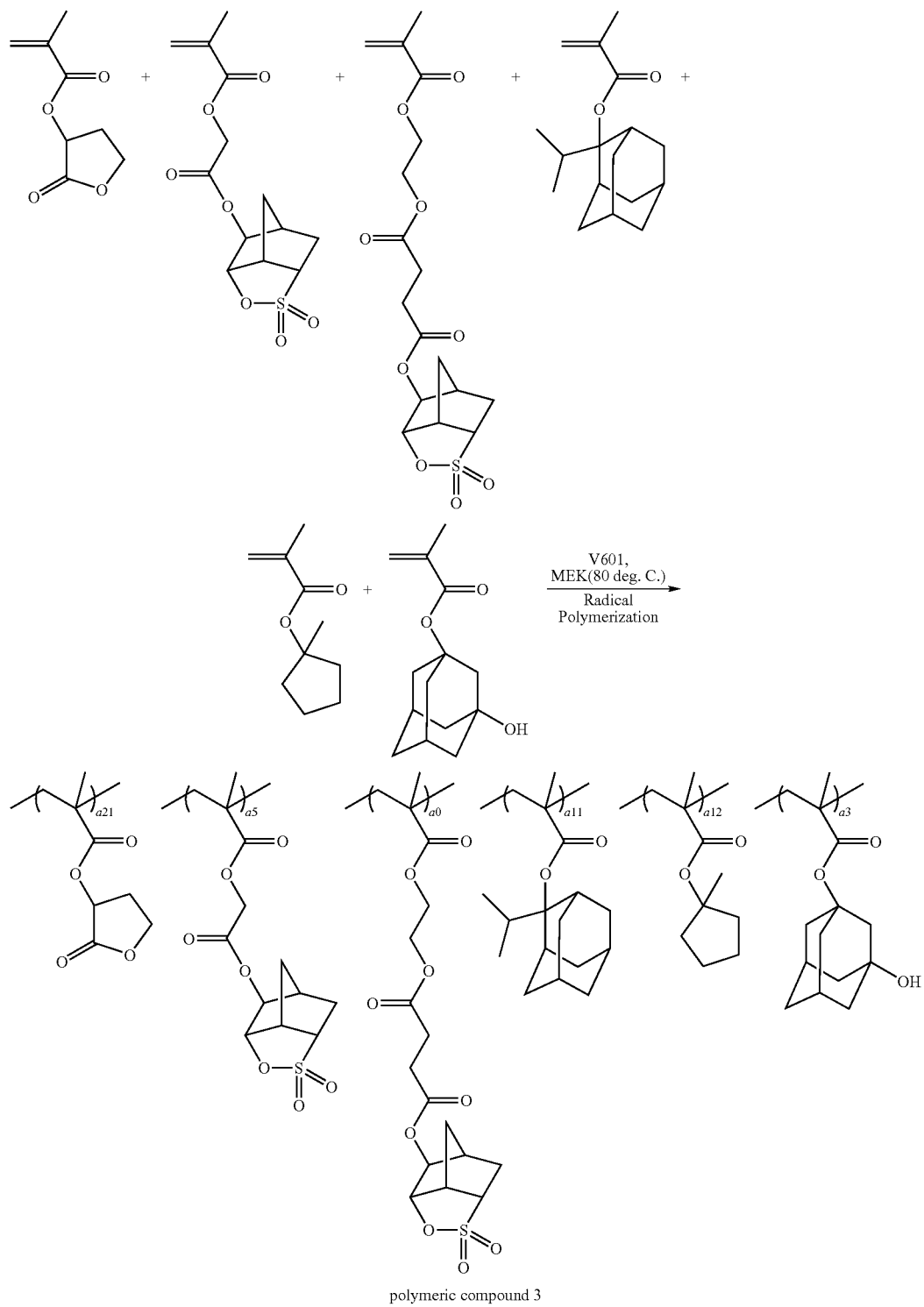
polymeric compound 3
[Mw = 5,800, Mw/Mn = 1.68; a21/a5/a0/a11/a12/a3 = 17.4/12.8/21.5/22.1/15.7/10.5]

Example 5
Polymer Synthesis Example 4
[Chemical Formula 61]
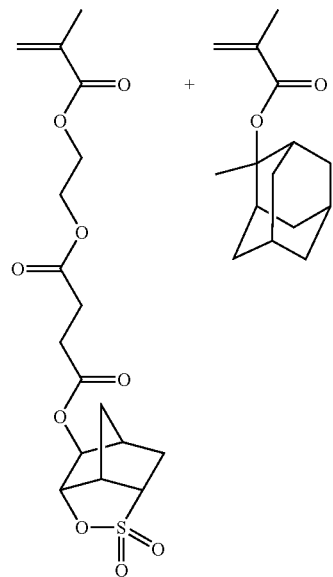
polymeric compound 4
[Mw = 9,000, Mw/Mn = 1.95; a0/a16 = 40.0/60.0]
Example 6
Polymer Synthesis Example 5
[Chemical Formula 62]
polymeric compound 5
[Mw = 7,000, Mw/Mn = 1.96; a0/a16/a3 = 35.5/43.7/20.8]

Example 7
Polymer Synthesis Example 6
[Chemical Formula 63]
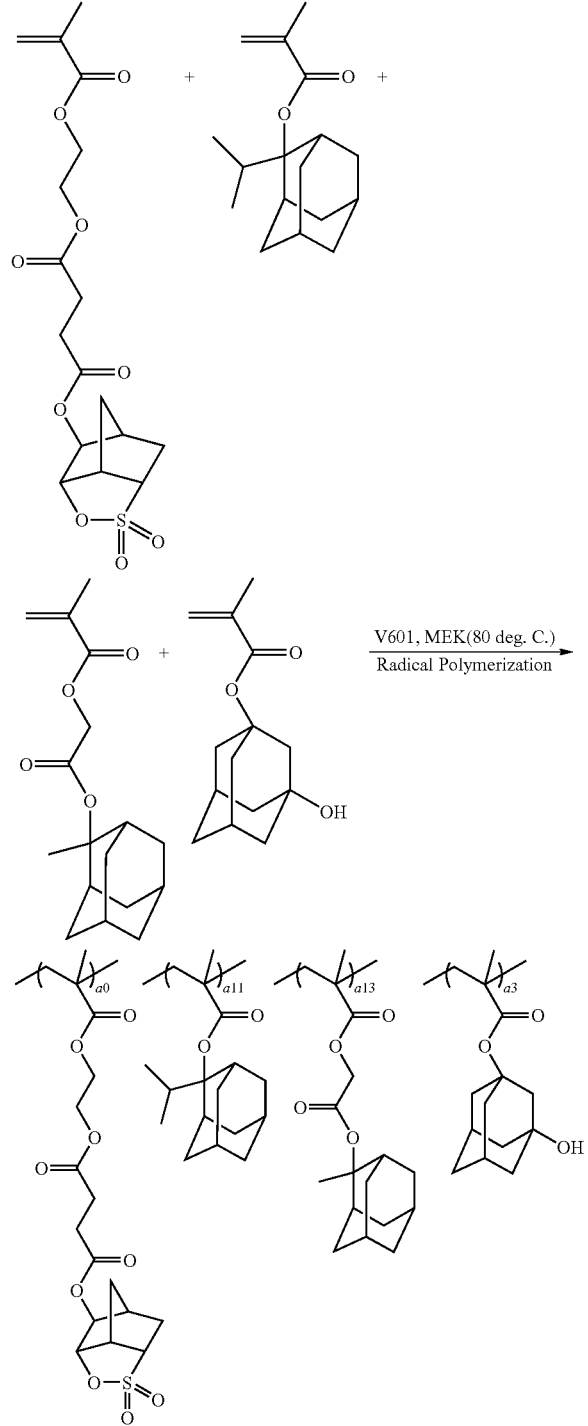
polymeric compound 6
[Mw = 6,700, Mw/Mn = 1.50; a0/a11/a13/a3 = 30.2/43.7/6.3/19.8]
Example 8
Polymer Synthesis Example 7
[Chemical Formula 64]
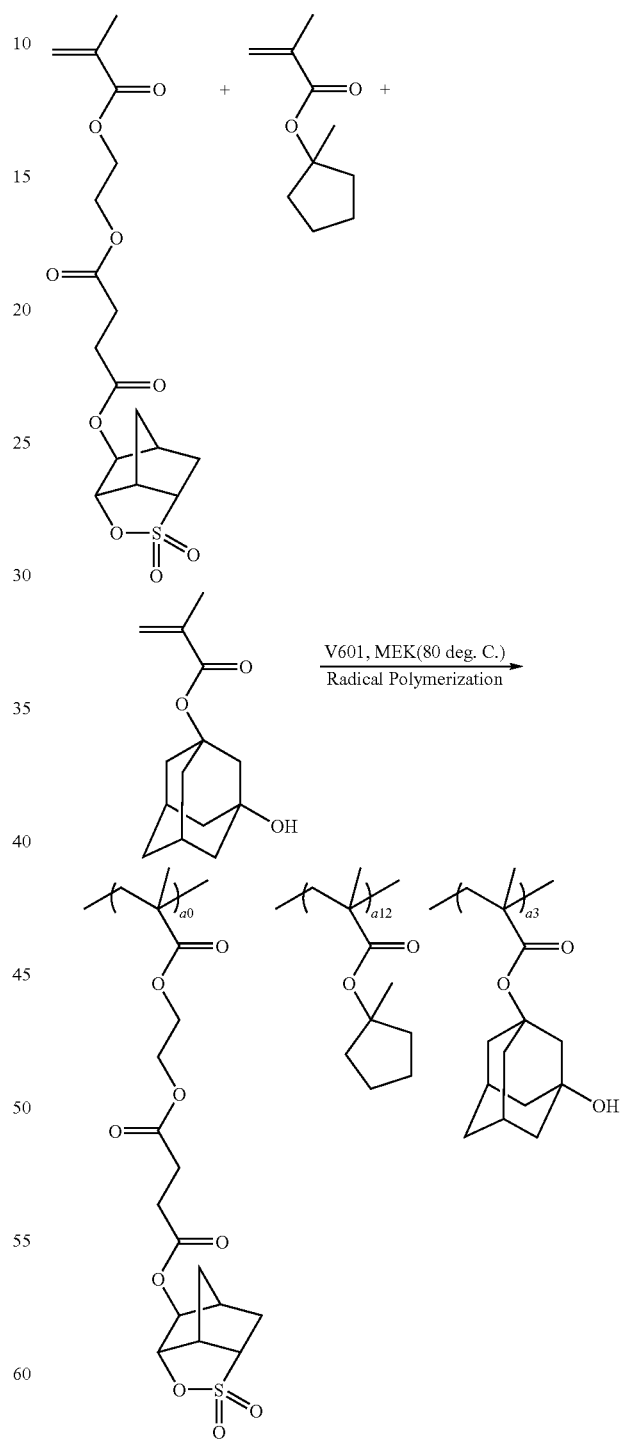
polymeric compound 7
[Mw = 9,200, Mw/Mn = 1.72; a0/a12/a3 = 39.3/41.1/19.6]

Example 9
Polymer Synthesis Example 8
[Chemical Formula 65]
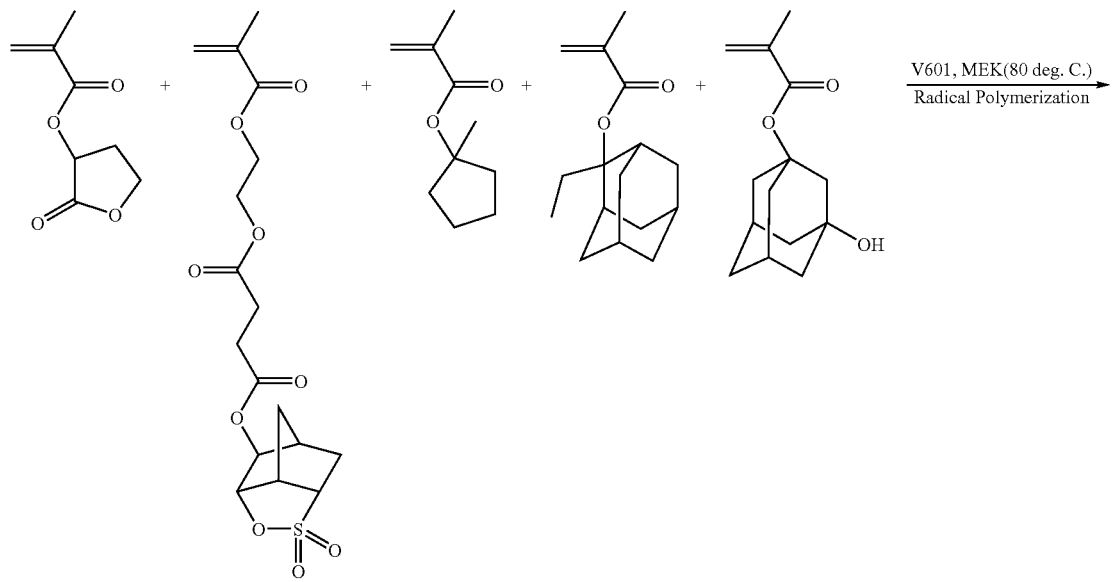
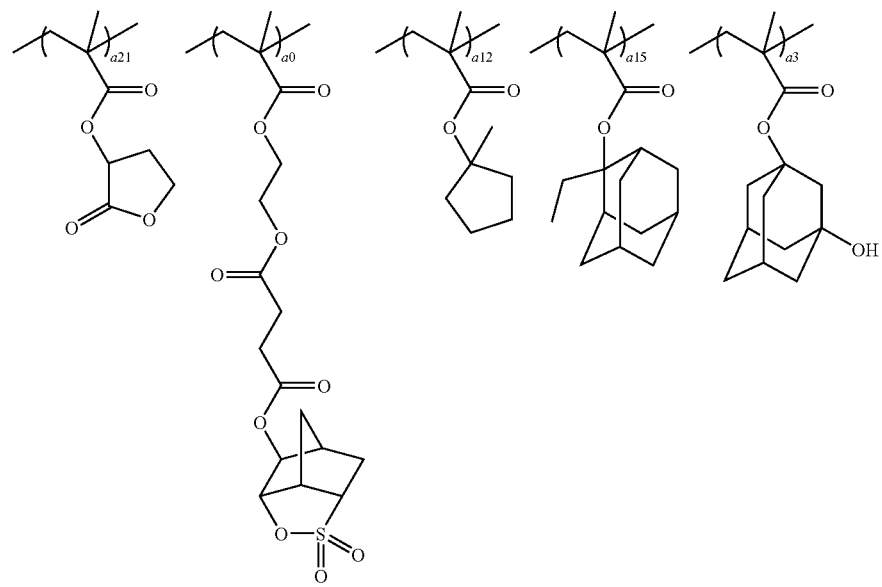
polymeric compound 8
[Mw = 7,700, Mw/Mn = 1.69; a21/a0/a12/a15/a3 = 34.9/26.0/12.6/19.0/7.5]

Example 10
Polymer Synthesis Example 9
[Chemical Formula 66]
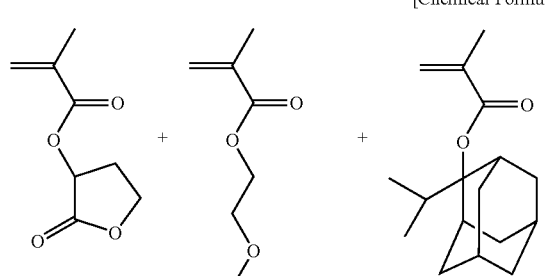
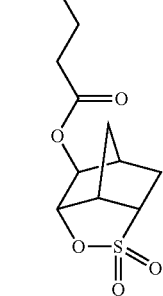
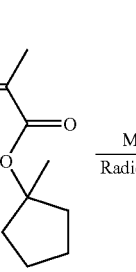
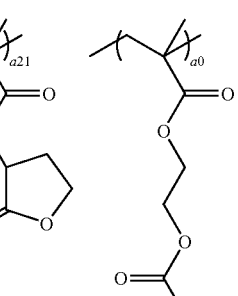
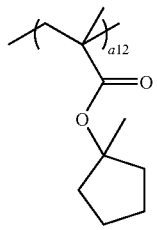
polymeric compound 9
[Mw = 6,900,
Mw/Mn = 1.66;
a21/a0/a11/a12 = 38.0/28.1/12/1/12.8]
Example 11
Polymer Synthesis Example 10
[Chemical Formula 67]
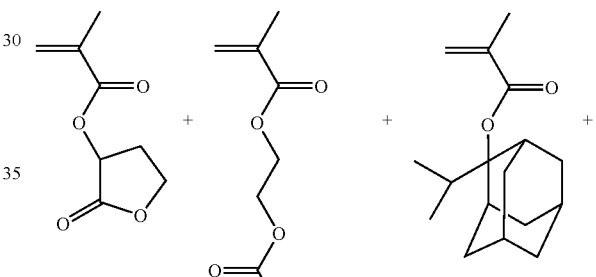
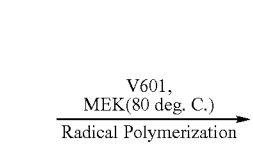

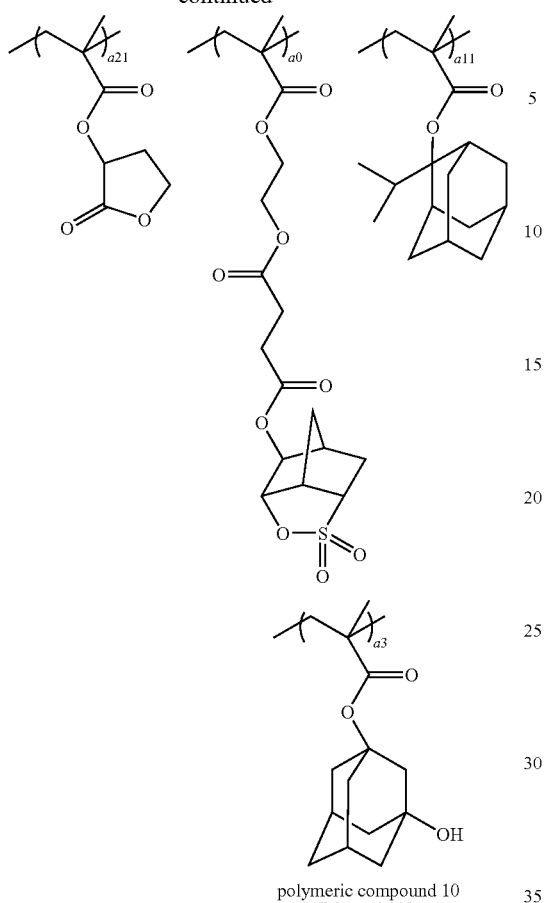
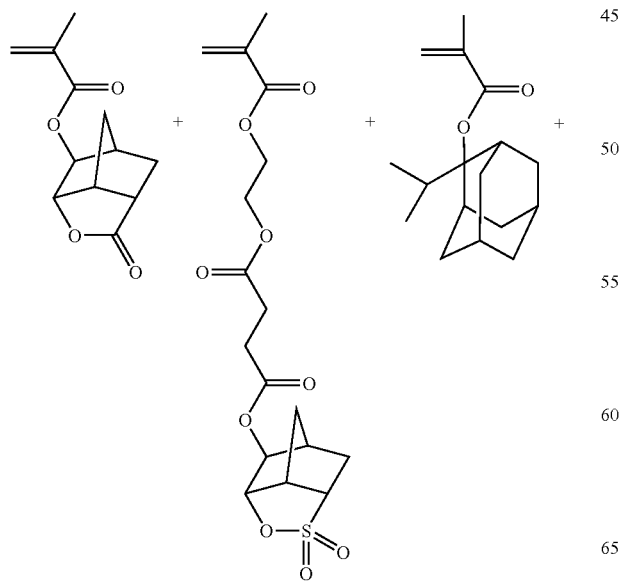
Example 12
Polymer Synthesis Example 11
[Chemical Formula 68]
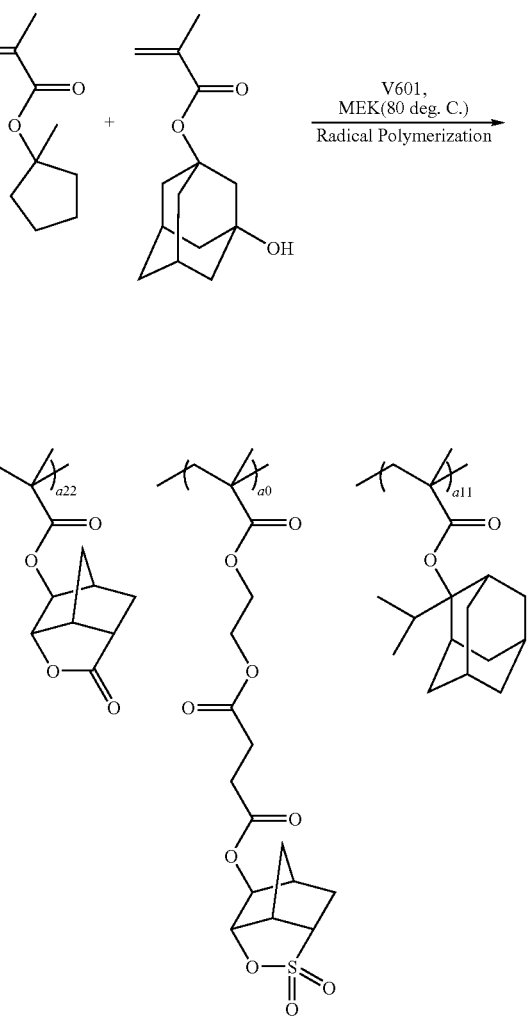

Example 13
Polymer Synthesis Example 12
[Chemical Formula 69]
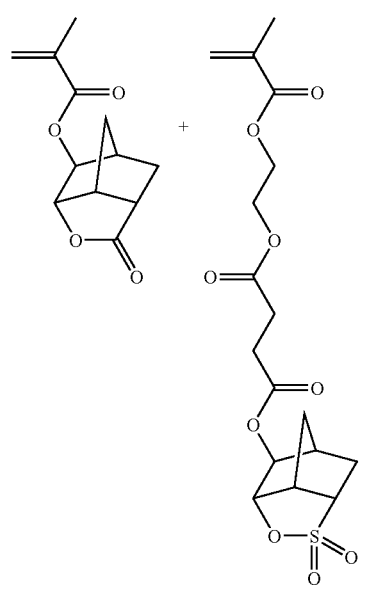
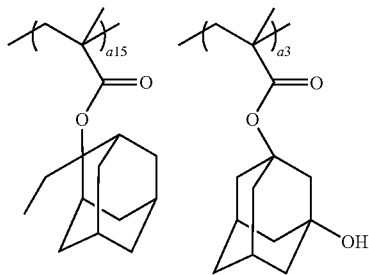
polymeric compound 12
[Mw = 7,200, Mw/Mn = 1.58;
a22/a0/a12/a15/a3 = 35.0/25.9/12.5/19.2/7.4]
Example 14
Polymer Synthesis Example 13
[Chemical Formula 70]
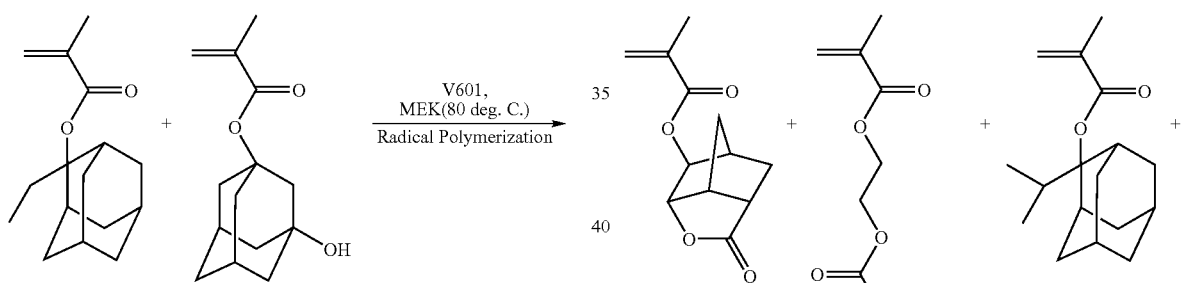
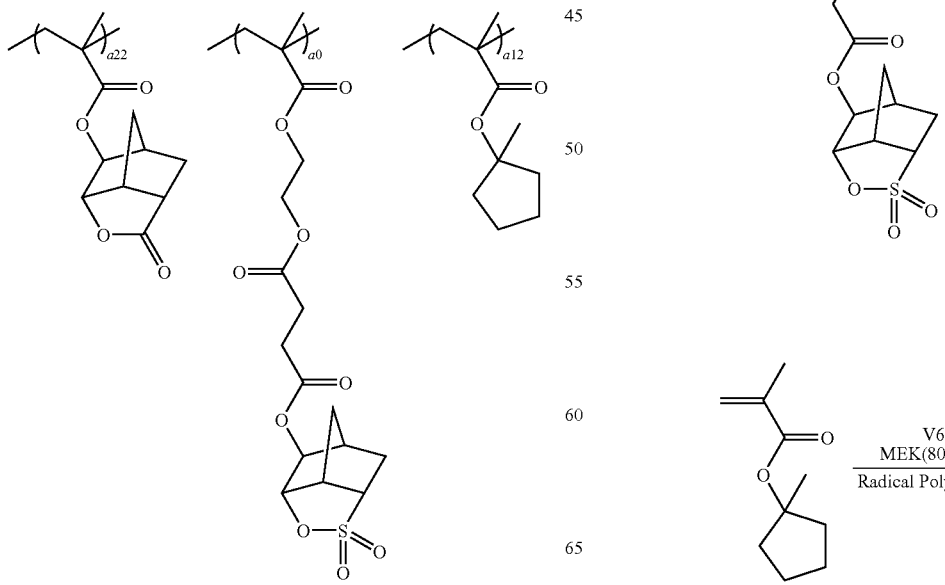
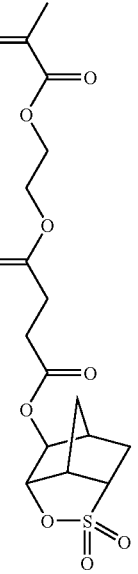

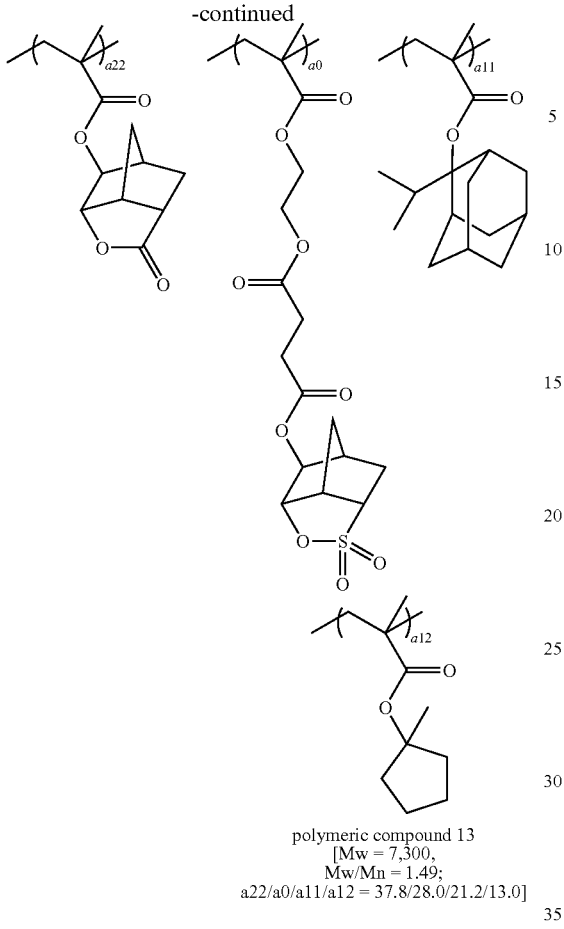
polymeric compound 13
[Mw = 7,300,
Mw/Mn = 1.49;
a22/a0/a11/a12 = 37.8/28.0/21.2/13.0]
Example 15
Polymer Synthesis Example 14
[Chemical Formula 71]
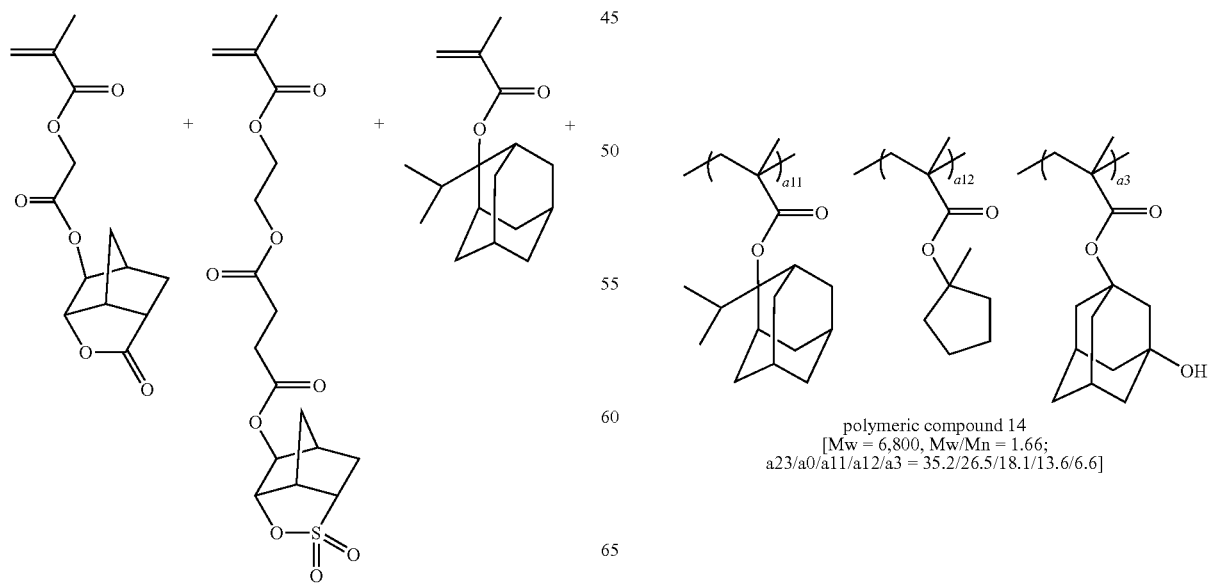
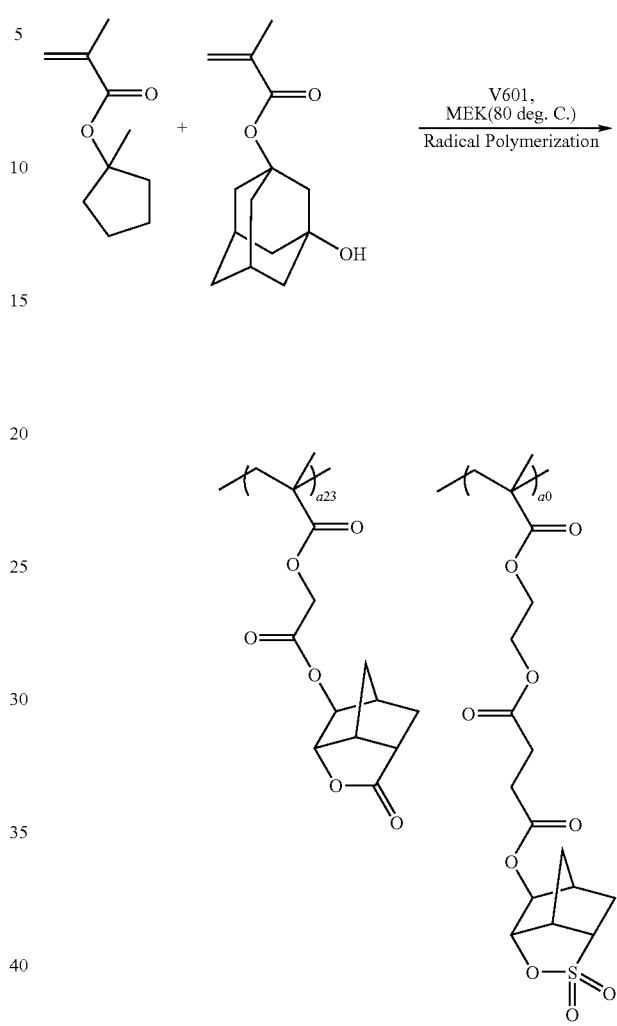
polymeric compound 14
[Mw = 6,800, Mw/Mn = 1.66;
a23/a0/a11/a12/a3 = 35.2/26.5/18.1/13.6/6.6]

Example 16
Polymer Synthesis Example 15
[Chemical Formula 72]
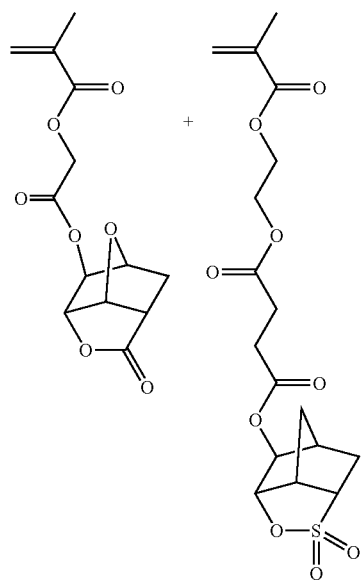
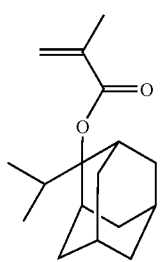
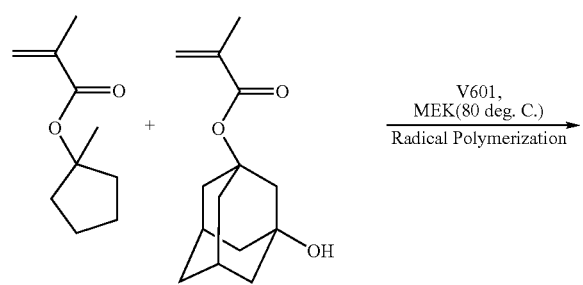
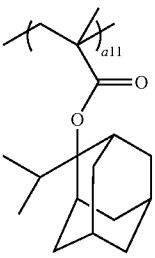
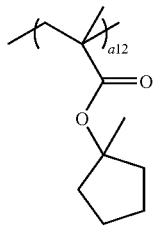
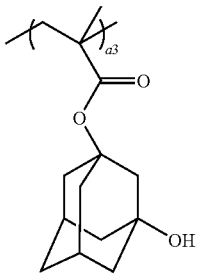
polymeric compound 15
[Mw = 6,200, Mw/Mn = 1.61;
a25/a0/a11/a12/a3 = 35.5/26.4/18.0/13.7/6.4]
Example 17
Polymer Synthesis Example 16
[Chemical Formula 73]
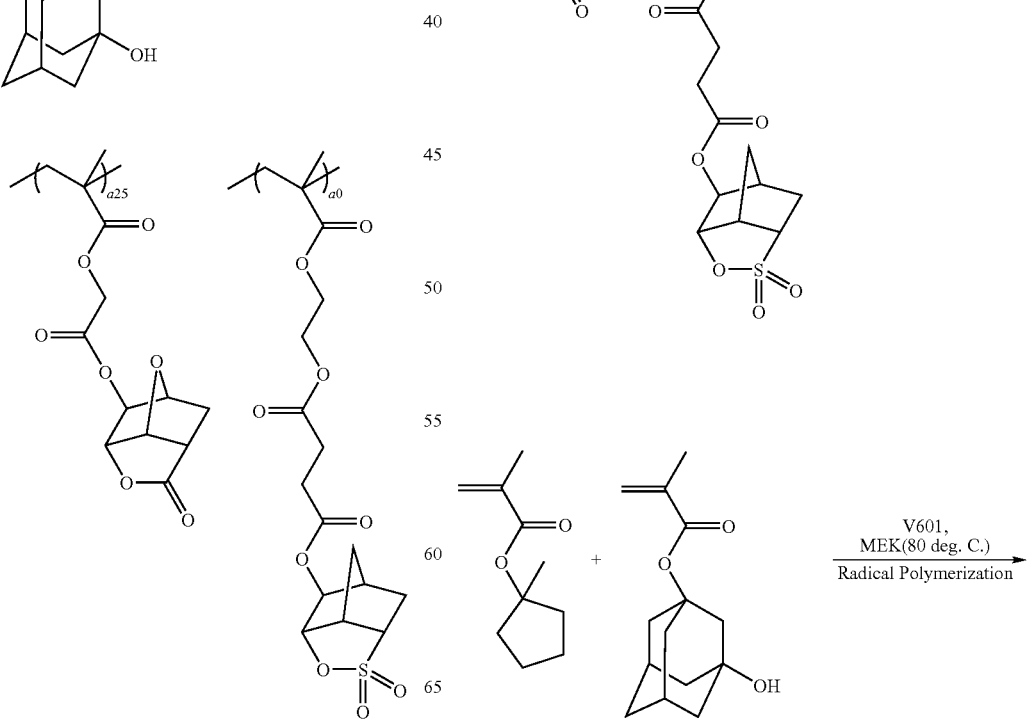

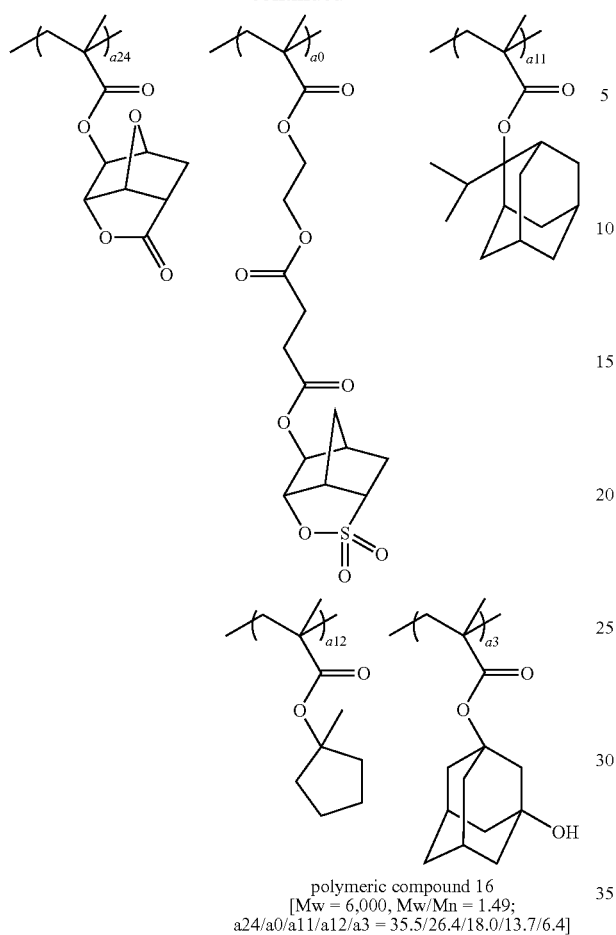
polymeric compound 16
[Mw = 6,000, Mw/Mn = 1.49;
a24/a0/a11/a12/a3 = 35.5/26.4/18.0/13.7/6.4]
Example 18
Polymer Synthesis Example 17
[Chemical Formula 74]
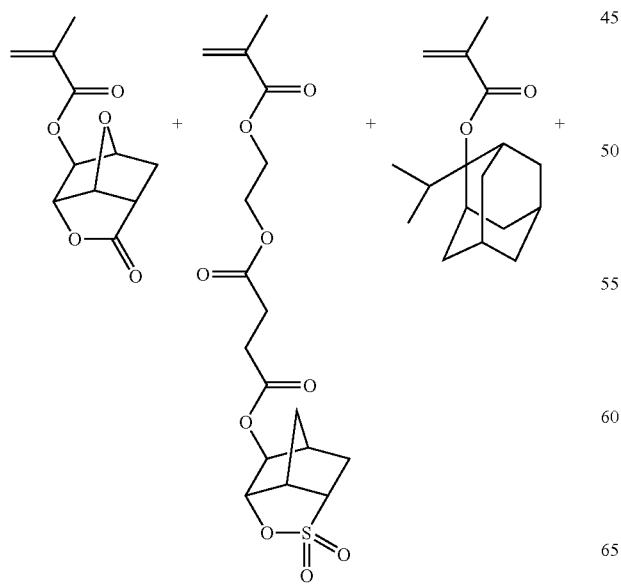
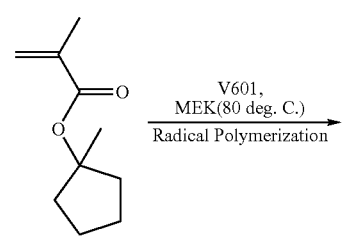
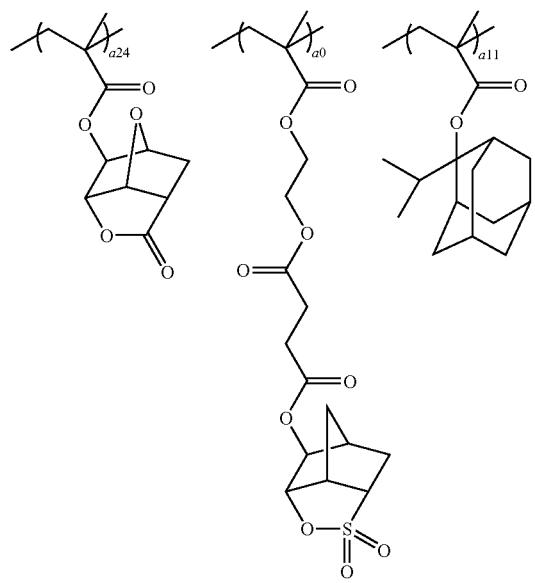
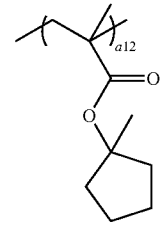
polymeric compound 17
[Mw = 6,900,
Mw/Mn = 1.58;
a24/a0/a11/a12 = 35.9/28.3/21.0/14.8]

Example 19
Polymer Synthesis Example 18
[Chemical Formula 75]
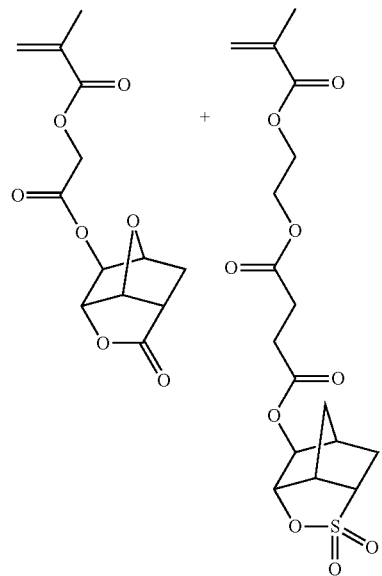
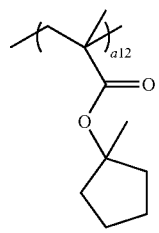
polymeric compound 18
[Mw = 6,000,
Mw/Mn = 1.66;
a25/a0/a11/a12 = 36.1/27.9/20.9/15.1]
Example 20
Polymer Synthesis Example 19
[Chemical Formula 76]
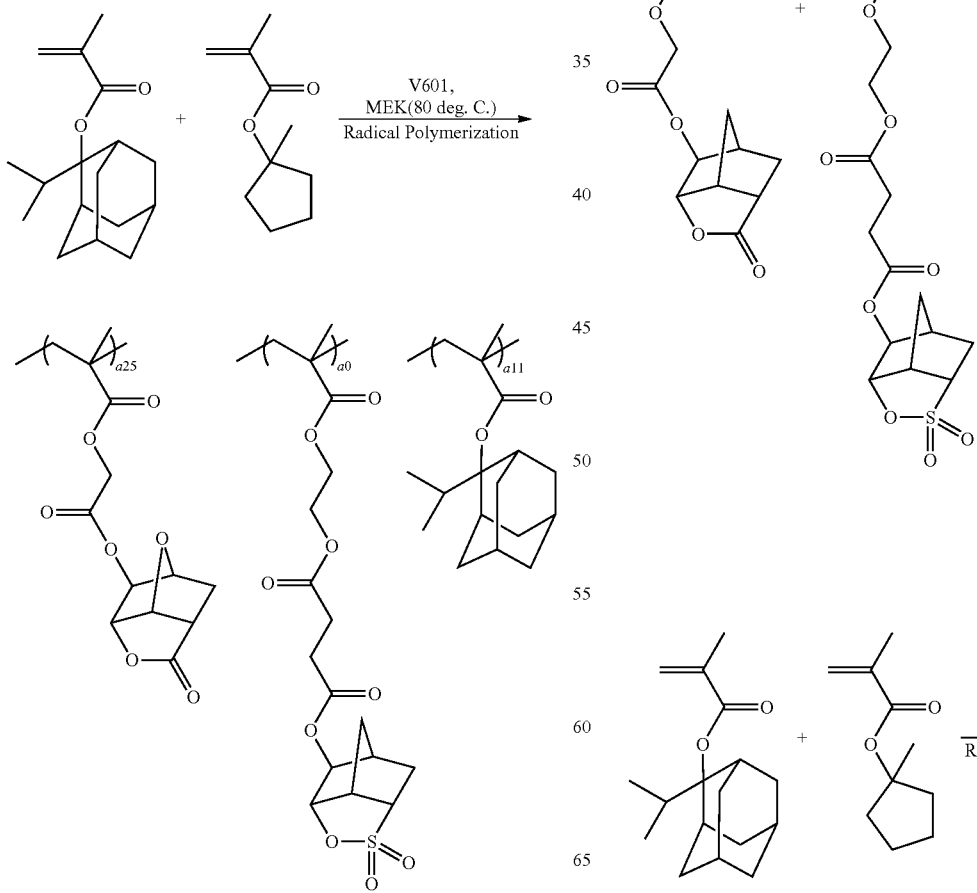

-continued
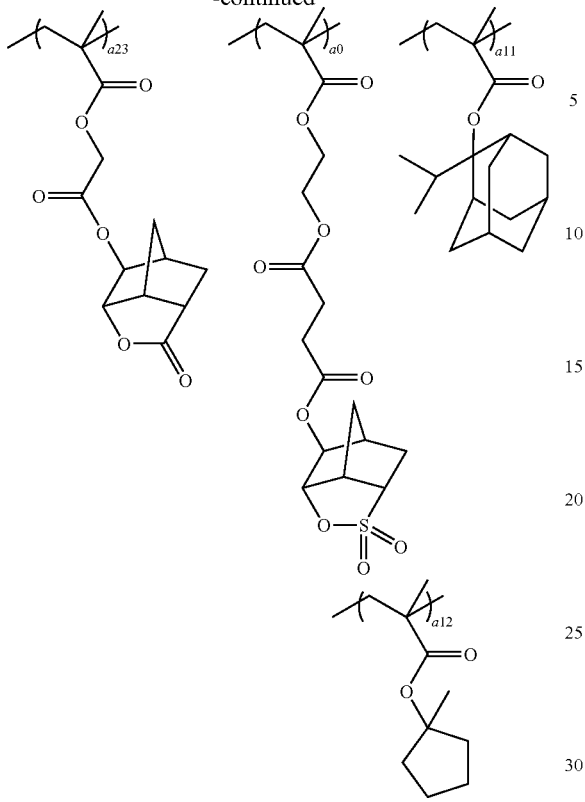
polymeric compound 19
[Mw = 6,400,
Mw/Mn = 1.63;
a23/a0/a11/a12 = 35.0/25.0/22.3/17.7]
Example 21
Polymer Synthesis Example 20
[Chemical Formula 77]
-continued
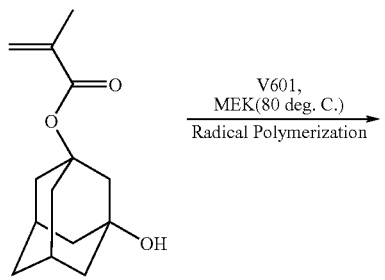
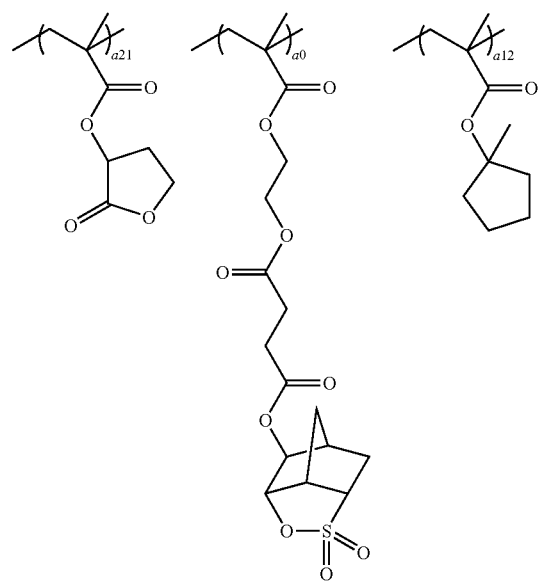
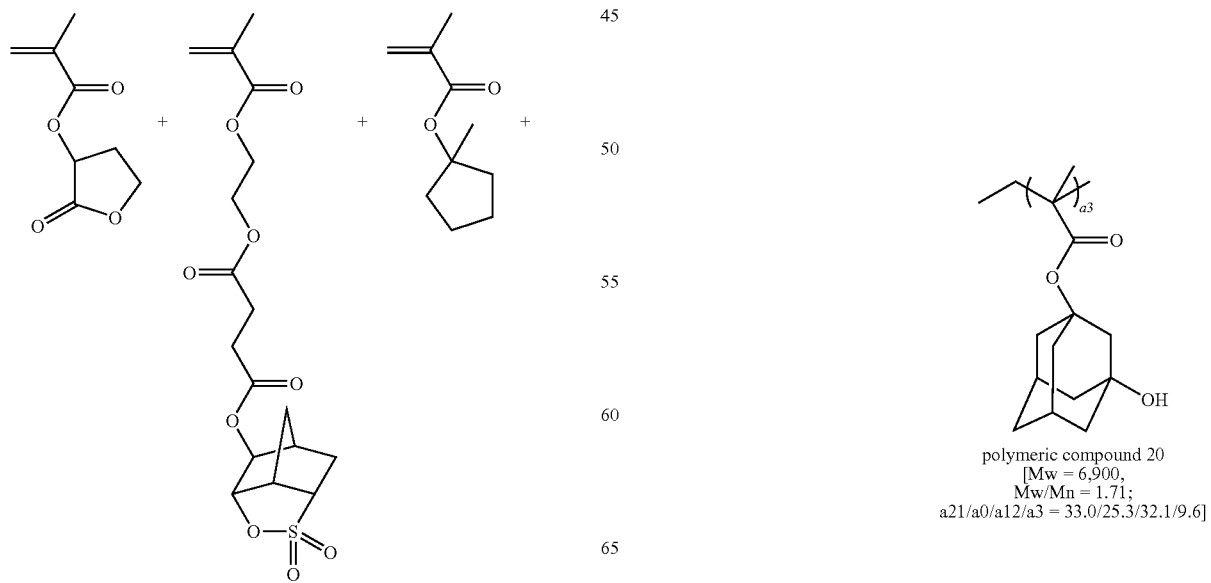
polymeric compound 20
[Mw = 6,900,
Mw/Mn = 1.71;
a21/a0/a12/a3 = 33.0/25.3/32.1/9.6]

Example 22
Polymer Synthesis Example 21
[Chemical Formula 78]
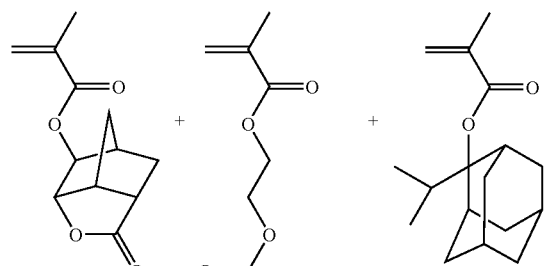
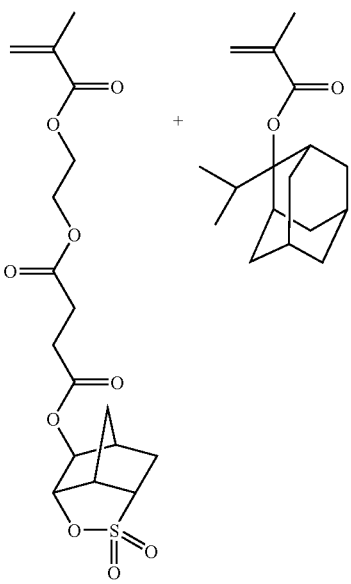
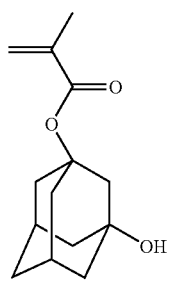
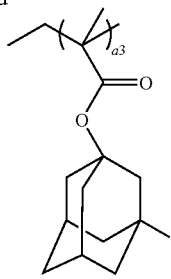
polymeric compound 21
[Mw = 6,800,
Mw/Mn = 1.66;
a22/a0/a11/a3 = 33.0/25.2/31.7/10.1]
Example 23
Polymer Synthesis Example 22
[Chemical Formula 79]
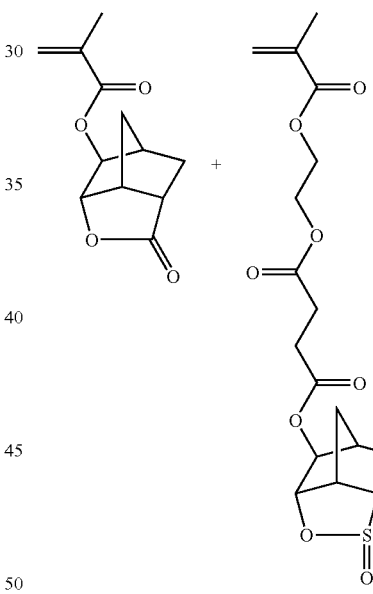
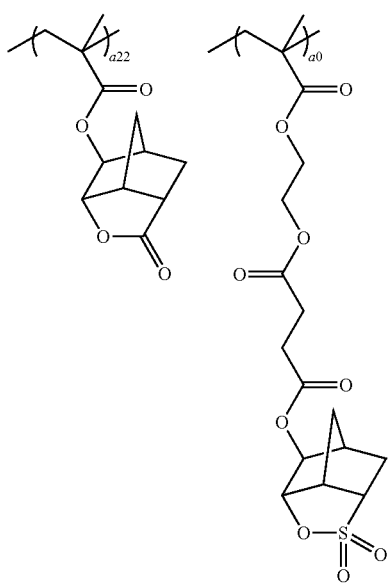
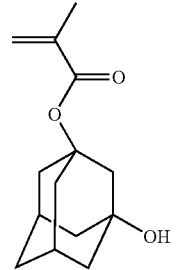

-continued
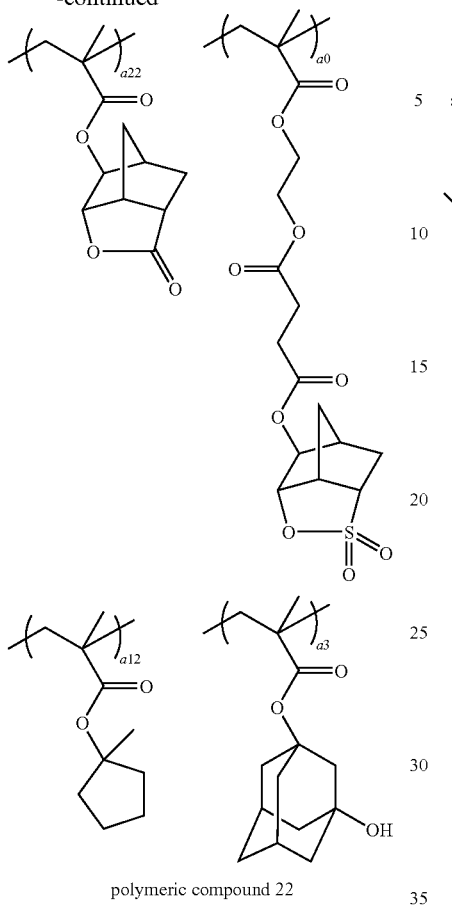
polymeric compound 22
[Mw = 6,100, Mw/Mn = 1.58;
a22/a0/a12/a3 = 33.3/25.0/32.3/9.4]
Example 24
Polymer Synthesis Example 23
[Chemical Formula 80]
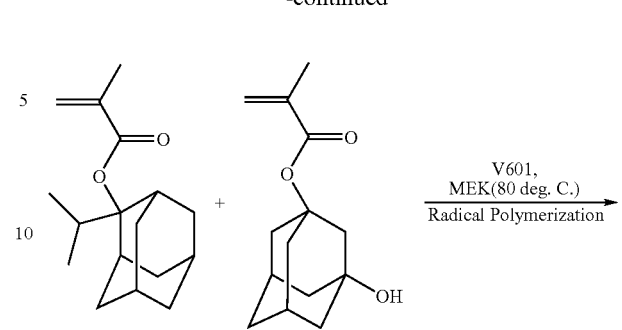
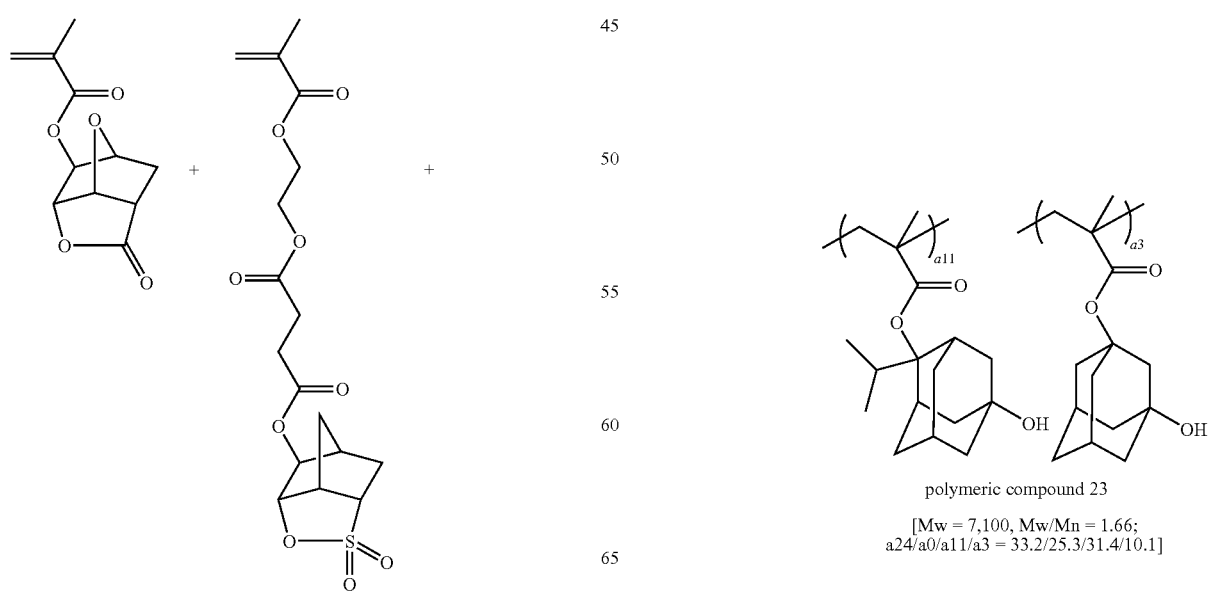
polymeric compound 23
[Mw = 7,100, Mw/Mn = 1.66;
a24/a0/a11/a3 = 33.2/25.3/31.4/10.1]

Example 25
Polymer Synthesis Example 24
[Chemical Formula 81]
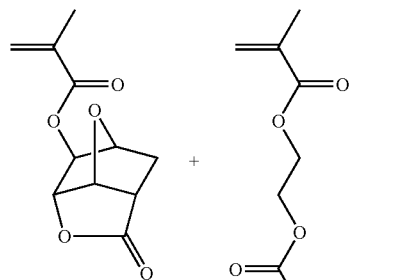
+
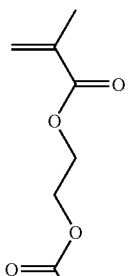
+
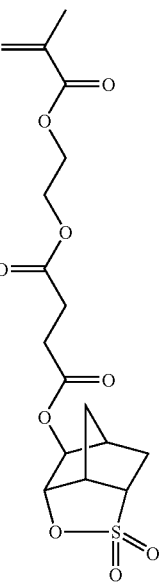
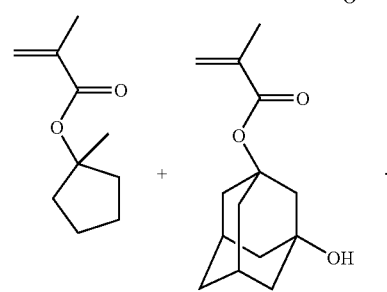
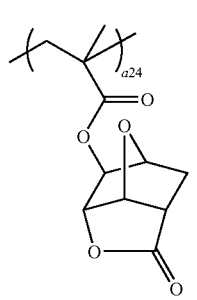
polymeric compound 24
[Mw = 7,200, Mw/Mn = 1.58;
a24/a0/a12/a3 = 33.2/24.9/32.5/9.4]
Example 26
Polymer Synthesis Example 25
[Chemical Formula 82]
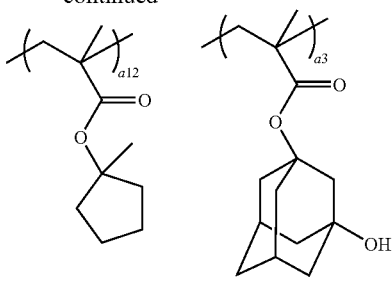
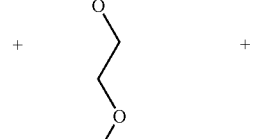
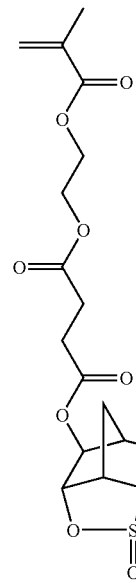
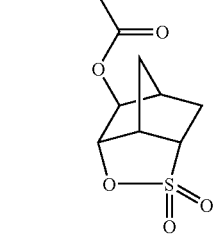

-continued
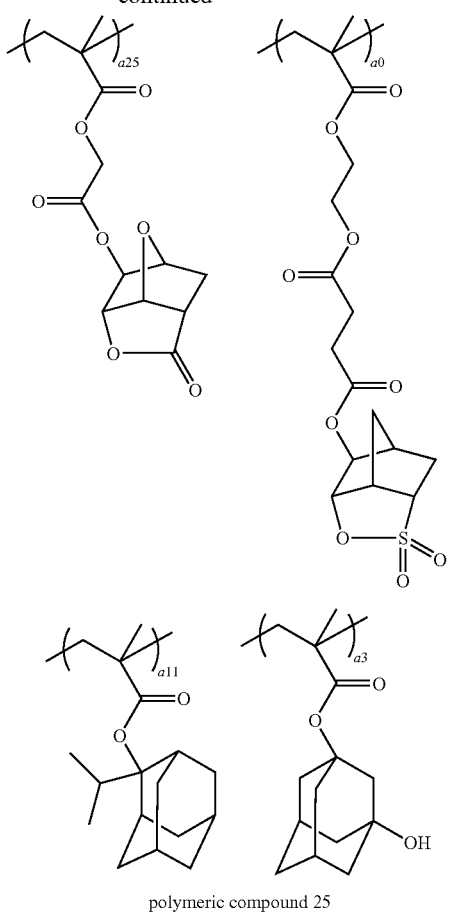
polymeric compound 25
[Mw = 7,000, Mw/Mn = 1.69; a25/a0/a11/a3 = 33.4/25.2/31.1/10.3]
Example 27
Polymer Synthesis Example 26
[Chemical Formula 83]
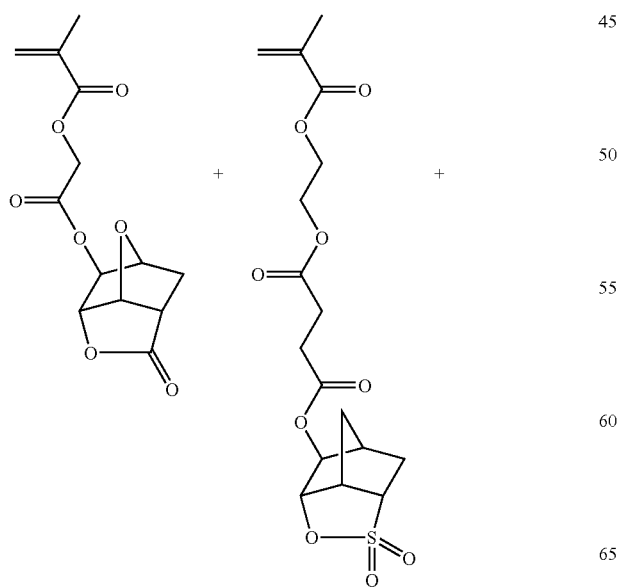
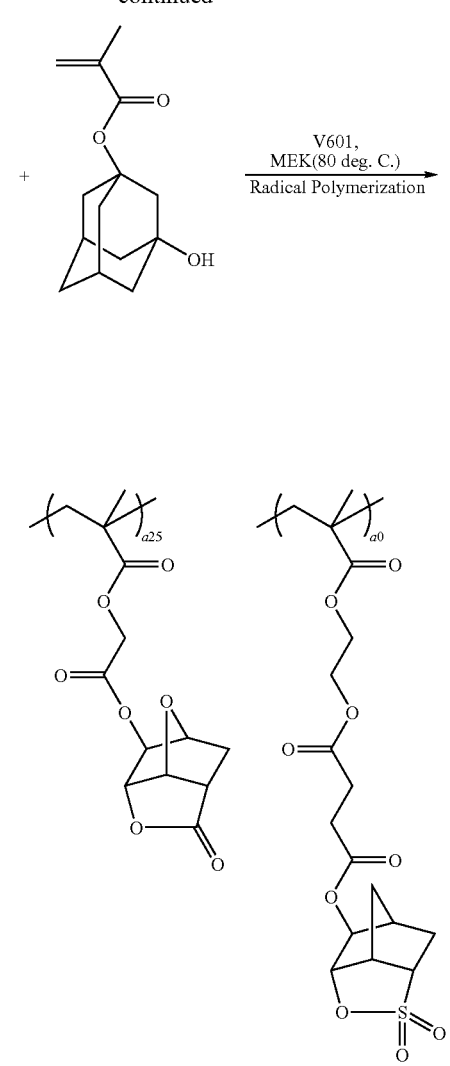
polymeric compound 26
[Mw = 6,600, Mw/Mn = 1.49; a25/a0/a12/a3 = 33.4/24.8/33.0/8.8]

Example 28
Polymer Synthesis Example 27
[Chemical Formula 84]
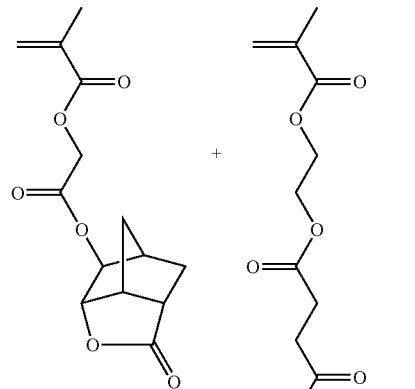
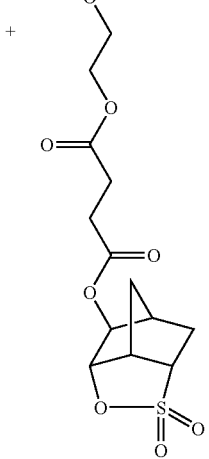
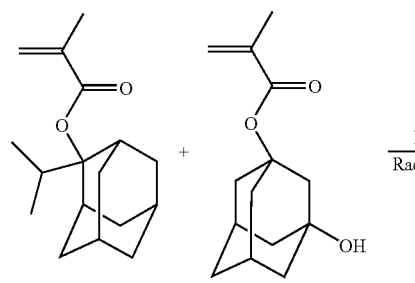
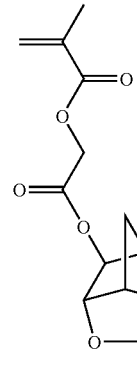
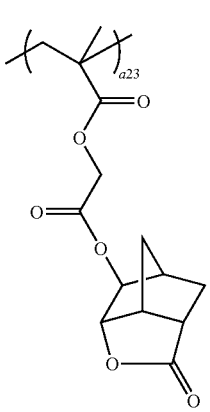
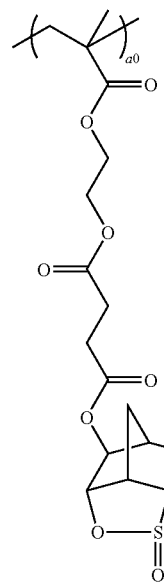
polymeric compound 27
[Mw = 6,900, Mw/Mn = 1.55; a23/a0/a11/a3 = 33.4/25.2/31.1/10.3]
Example 29
Polymer Synthesis Example 28
[Chemical Formula 85]
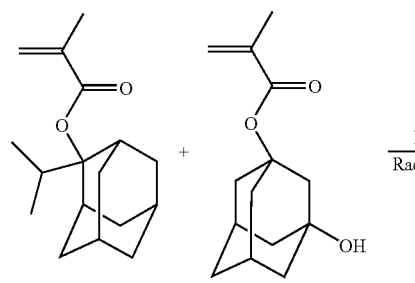
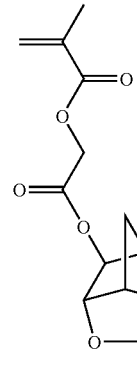
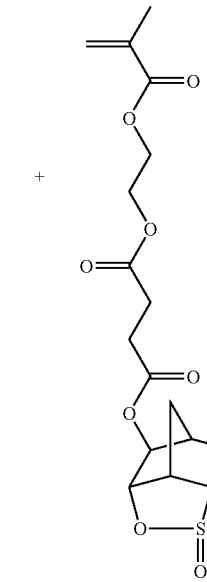
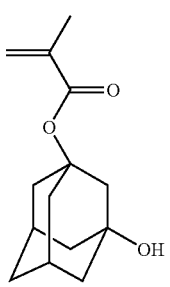
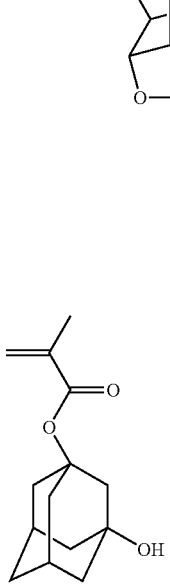

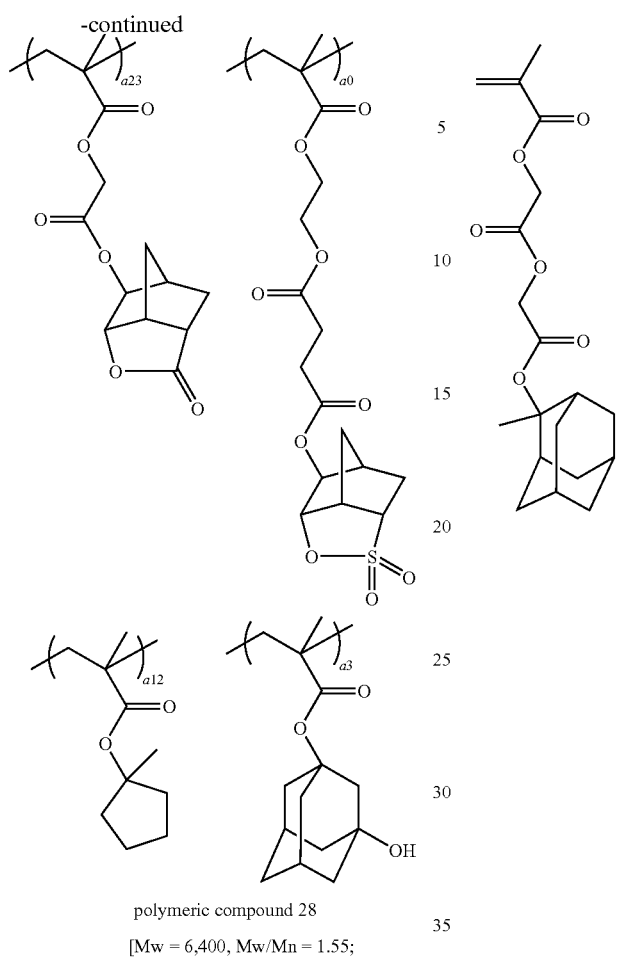
polymeric compound 28
[Mw = 6,400, Mw/Mn = 1.55;
a23/a0/a12/a3 = 33.0/24.9/32.8/9.3]
Example 30
Polymer Synthesis Example 29
[Chemical Formula 86]
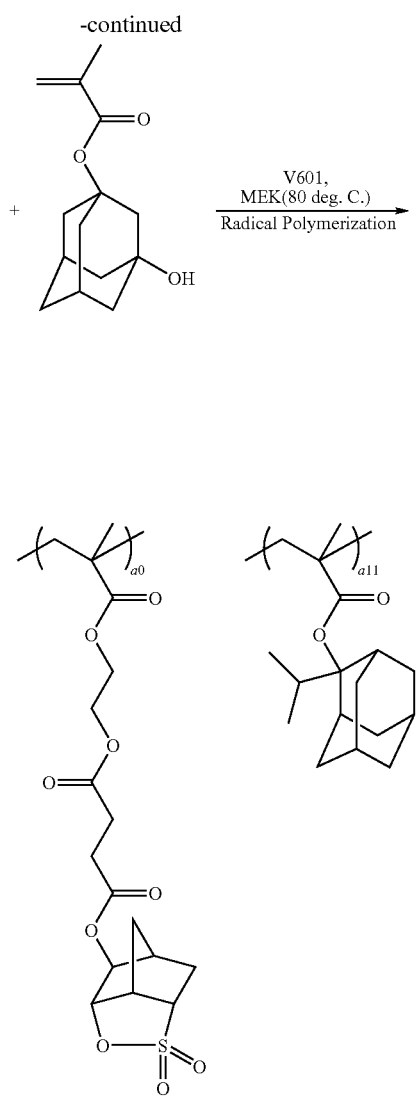
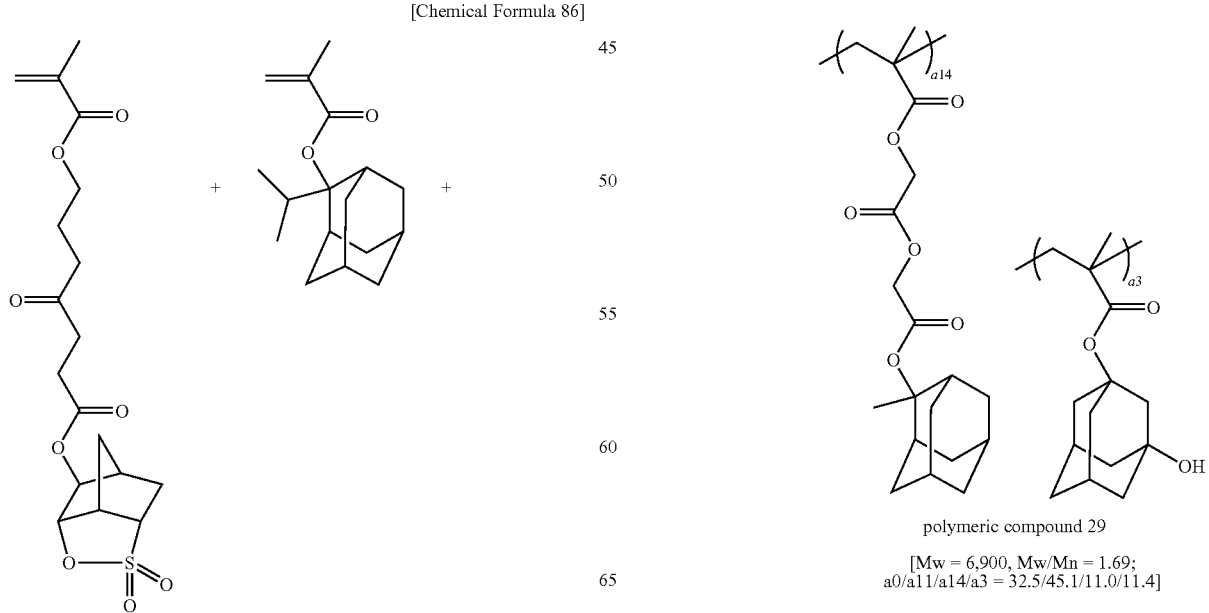
polymeric compound 29
[Mw = 6,900, Mw/Mn = 1.69;
a0/a11/a14/a3 = 32.5/45.1/11.0/11.4]

Example 31
Polymer Synthesis Example 30
[Chemical Formula 87]
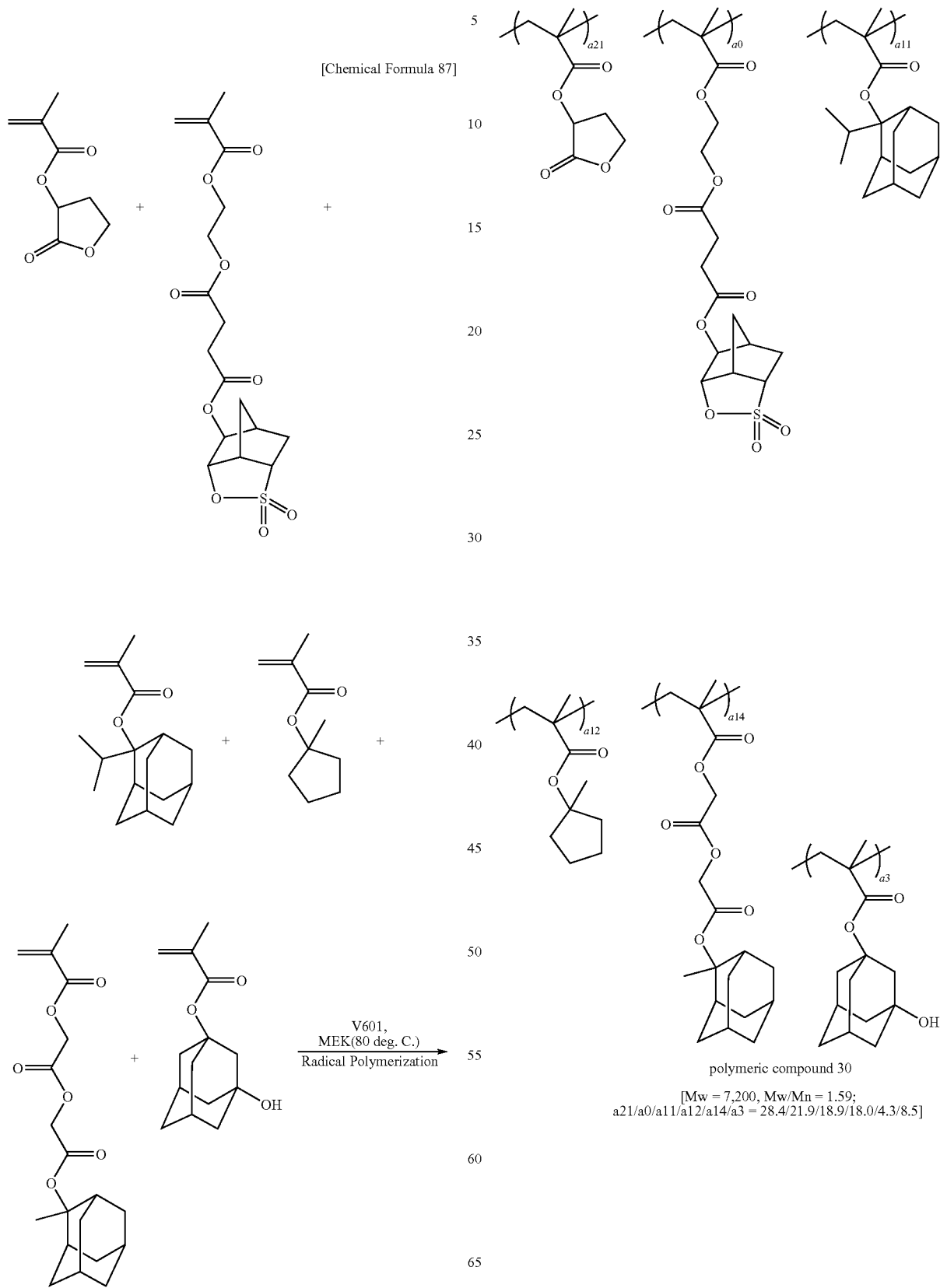
polymeric compound 30
[Mw = 7,200, Mw/Mn = 1.59;
a21/a0/a11/a12/a14/a3 = 28.4/21.9/18.9/18.0/4.3/8.5]

Example 32
Polymer Synthesis Example 31
[Chemical Formula 88]
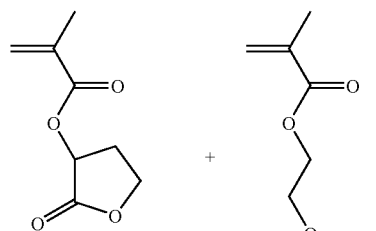
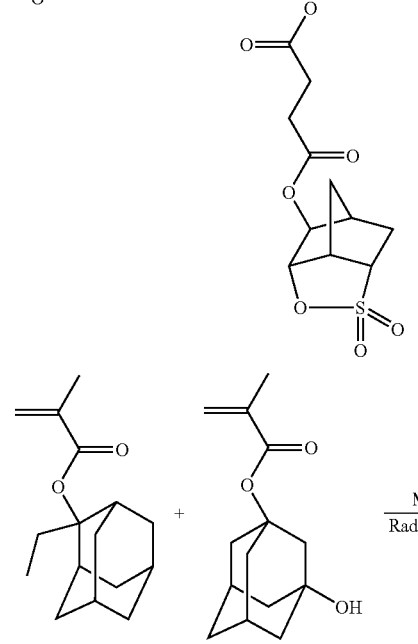
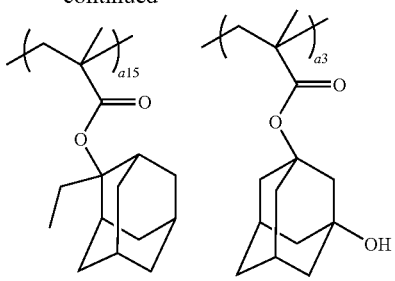
polymeric compound 31
[Mw = 6,600, Mw/Mn = 1.69;
a21/a0/a15/a3 = 33.5/21.4/28.5/16.6]
Example 33
Polymer Synthesis Example 32
[Chemical Formula 89]
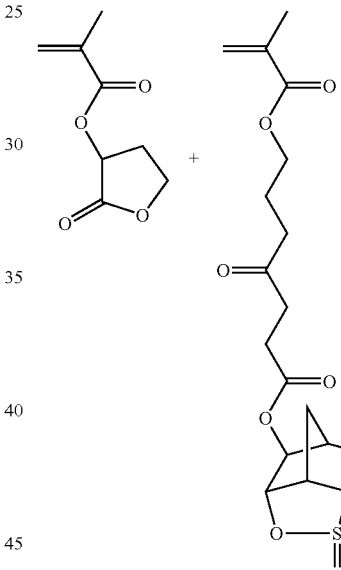
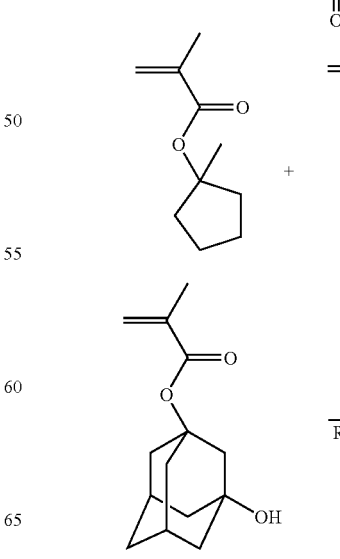

-continued

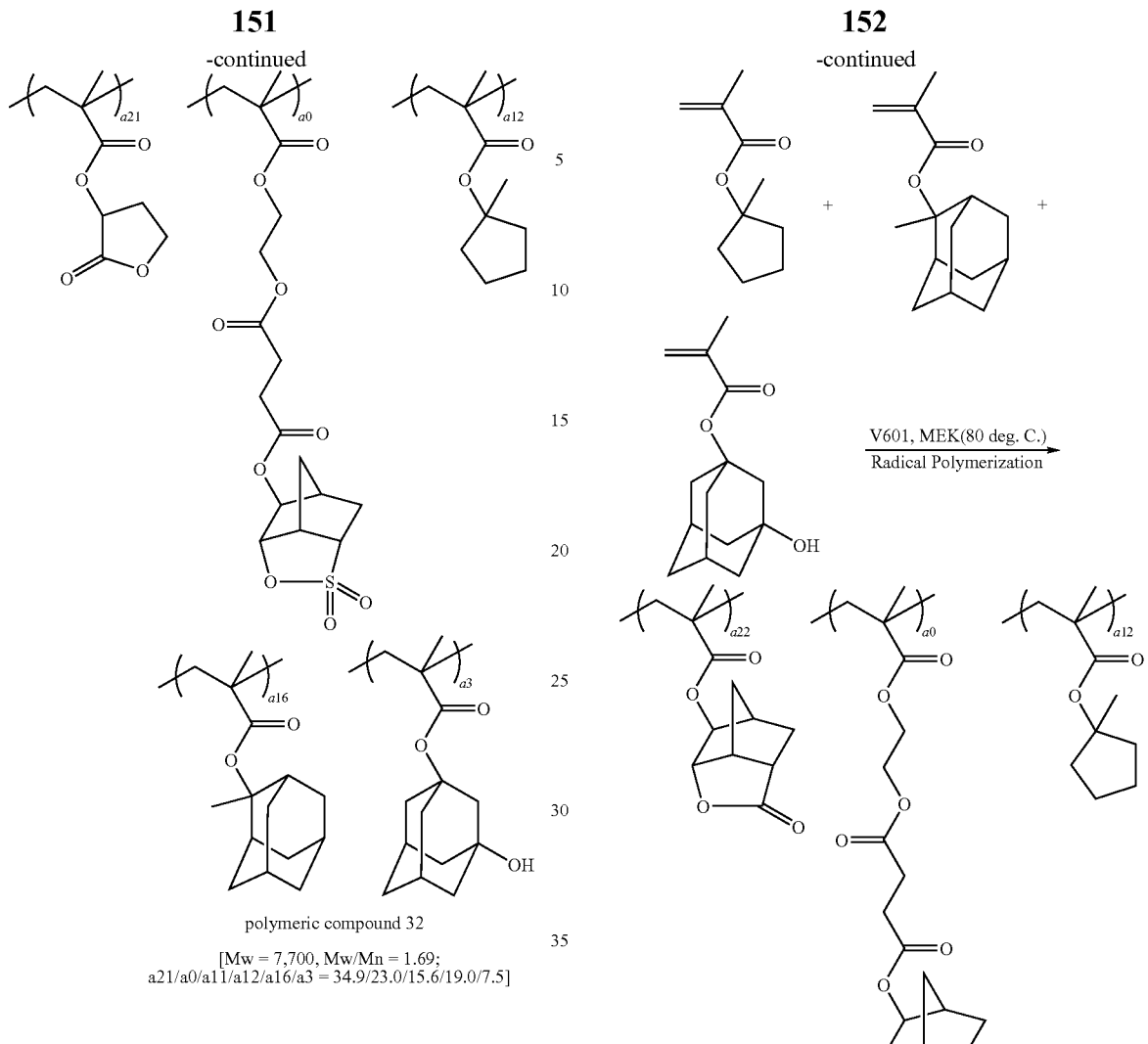

polymeric compound 32

[Mw = 7,700, Mw/Mn = 1.69;
a21/a0/a11/a12/a16/a3 = 34.9/23.0/15.6/19.0/7.5]

Example 34

Polymer Synthesis Example 33

[Chemical Formula 90]

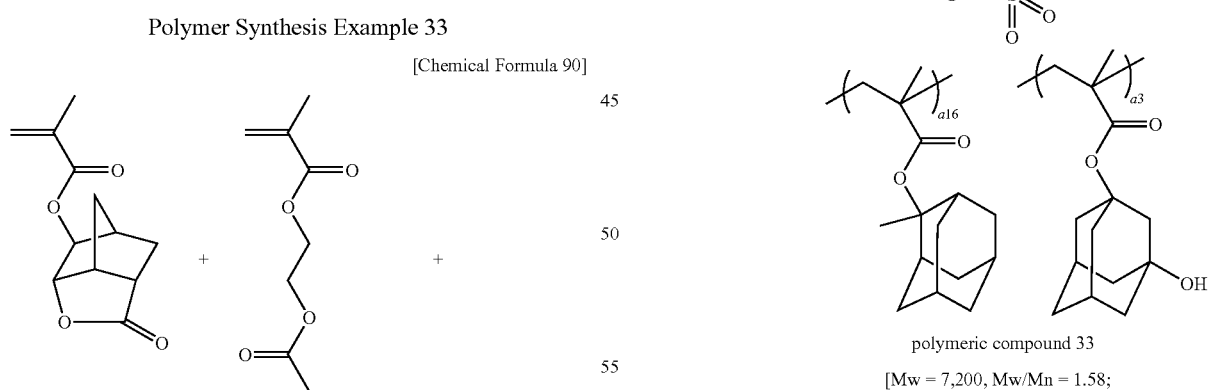

-continued polymeric compound 33

[Mw = 7,200, Mw/Mn = 1.58;
a22/a0/a12/a16/a3 = 35.0/23.9/14.5/19.2/7.4]

<Synthesis of Acid Generator Component (B)>

The acid generator (I-1-81) was synthesized according to the acid generator synthesis example described below.

[Acid Generator Synthesis Example 1]

(i) Synthesis Example of Compound (IV)

150 g of methyl fluorosulfonyl(difluoro)acetate and 375 g of pure water were maintained at 10° C. or lower in an ice bath, and 343.6 g of a 30% aqueous solution of sodium hydroxide was dropwise added thereto. Then, the resultant was refluxed at 100° C. for 3 hours, followed by cooling and neutralizing with concentrated hydrochloric acid. The resulting solution was dropwise added to 8,888 g of acetone, and the precipitate was collected by filtration and dried, thereby obtaining 184.5 g of the compound (1) shown below in the form of a white solid (purity: 88.9%, yield: 95.5%).

[Chemical Formula 91]

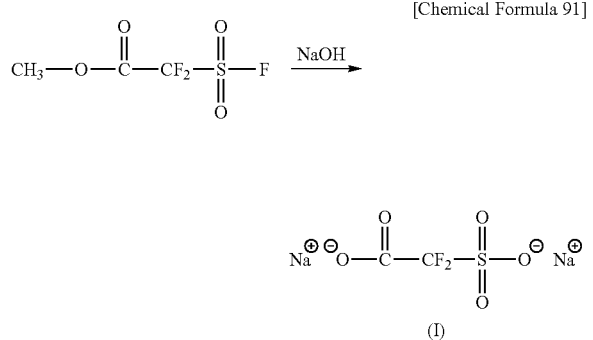

Subsequently, 56.2 g of the compound (I) and 562.2 g of acetonitrile were prepared, and 77.4 g of p-toluenesulfonic acid monohydrate were added thereto. Then, the resultant solution was refluxed for three hours at 110° C. Then, the solution was filtered, and the filtrate was concentrated and dried to obtain a solid. 900 g of t-butyl methyl ether was added to the obtained solid and stirred. Thereafter, the resultant was filtered, and the residue was dried, thereby obtaining 22.2 g of the compound (II) shown below in the form of a white solid (purity: 91.0%, yield: 44.9%).

[Chemical Formula 92]

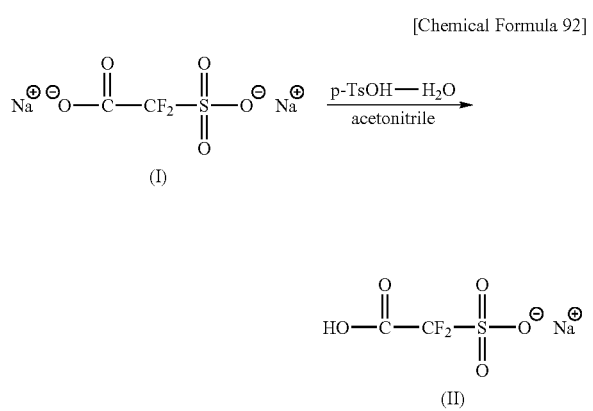

Subsequently, 4.34 g of the compound (II) (purity: 94.1%), 3.14 g of 2-benzyloxyethanol, and 43.4 g of toluene were prepared, and 0.47 g of p-toluenesulfonic acid monohydrate was added thereto. The resultant solution was then refluxed for 20 hours at 105° C. The reaction solution was filtrated, and 20 g of hexane was added to the residue. Then, the resultant was stirred. The resultant was filtrated one more time, and then the residue was dried, thereby obtaining 1.41 g of the compound (III) shown below (yield: 43.1%).

[Chemical Formula 93]

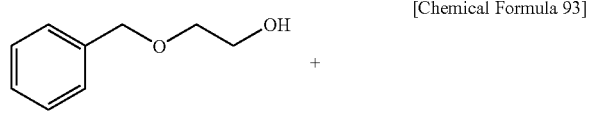

+

[Chemical Formula 94]

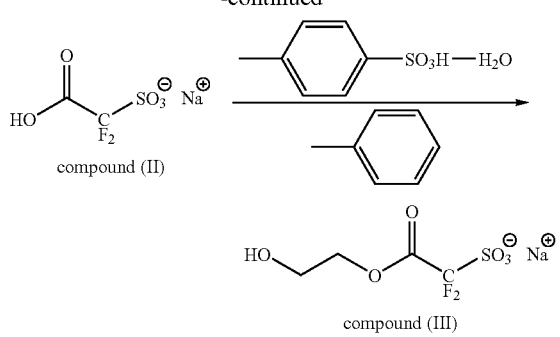

The compound (III) thus obtained was analyzed using NMR.

$^1$H-NMR (DMSO-d6, 400 MHz): δ(ppm)=4.74-4.83 (t, 1H, OH), 4.18-4.22 (t, 2H, H$^a$), 3.59-3.64 (q, 2H, H$^b$).

$^{19}$F-NMR (DMSO-d6, 376 MHz): δ(ppm)=−106.6.

From the results described above, it was confirmed that the compound (III) had the structure shown below.

[Chemical Formula 94]

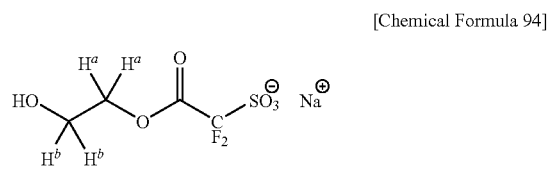

Subsequently, 0.82 g of 1-adamantanecarbonyl chloride and 0.397 g of triethylamine were dropwise added to 1.00 g of the compound (III) and 3.00 g of acetonitrile in an ice bath. After the dropwise addition, the solution was stirred for 20 hours at room temperature, and then filtrated. The filtrate was concentrated and dried, then dissolved in 30 g of dichloromethane, and washed with water three times. The organic phase was concentrated and dried, thereby obtaining 0.82 g of the compound (1V) shown below (yield: 41%).

[Chemical Formula 95]

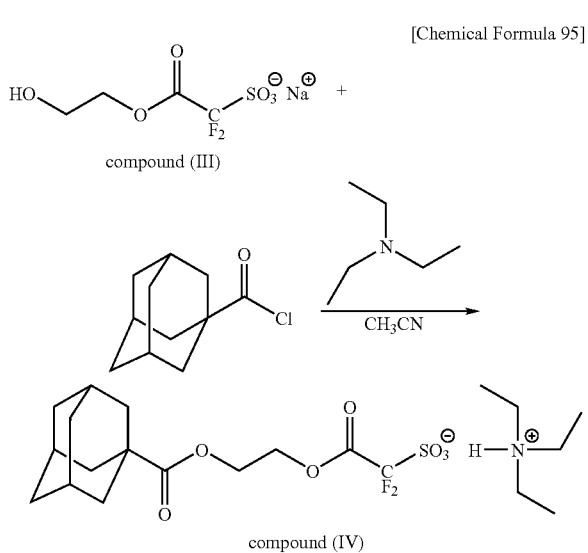

The compound (IV) thus obtained was analyzed using NMR.

$^1$H-NMR (DMSO-d6, 400 MHz): δ (ppm)=8.81 (s, 1H, H$^c$), 4.37-4.44 (t, 2H, H$^d$), 4.17-4.26 (t, 2H, H$^e$), 3.03-3.15 (q, 6H, H$^b$), 1.61-1.98 (m, 15H, Adamantane), 1.10-1.24 (t, 9H, H$^a$).

$^{19}$F-NMR. (DMSO-d6, 376 MHz): δ (ppm)=−106.61.

From the results described above, it was confirmed that the compound (IV) had the structure shown below.

[Chemical Formula 96]

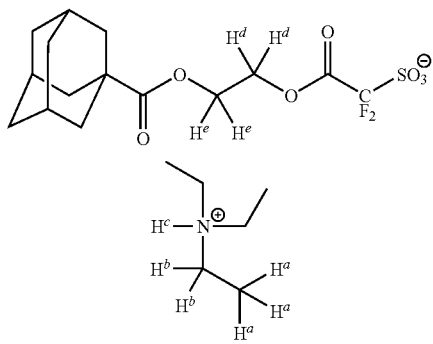

(ii) Synthesis Example of Acid Generator (I-1-81)

2 g of the compound (V) shown below was added to 20 g of dichloromethane and 20 g of water, and then stirred. 2.54 g of the compound (IV) was added thereto, and stirred for 1 hour. Then, liquid separation of the reaction solution was conducted to take out the organic solvent phase, and the resultant organic solvent phase was washed four times with 20 g of water. After being washed, the organic solvent phase was concentrated and dried, thereby obtaining 2.3 g of the acid generator (I-1-81).

The compound (I-1-81) thus obtained was analyzed using NMR.

$^1$H-NMR (DMSO-d6, 400 MHz): δ(ppm)=7.72-7.83 (m, 10H, Ar), 7.72 (s, 2H, Ar), 6.49-6.55 (m, 1H, Vinyl), 4.37-4.44 (t, 2H, CH$_2$), 4.20-4.23 (d, 1H, Vinyl), 4.00-4.26 (m, 7H, CH$_2$+Vinyl), 2.27 (s, 6H, CH$_3$), 1.61-1.98 (m, 15H, Adamantane).

$^{19}$F-NMR (DMSO-d6, 376 MHz): δ(ppm)=−106.61.

From the results described above, it was confirmed that the compound (I-1-81) had the structure shown below.

[Chemical Formula 97]

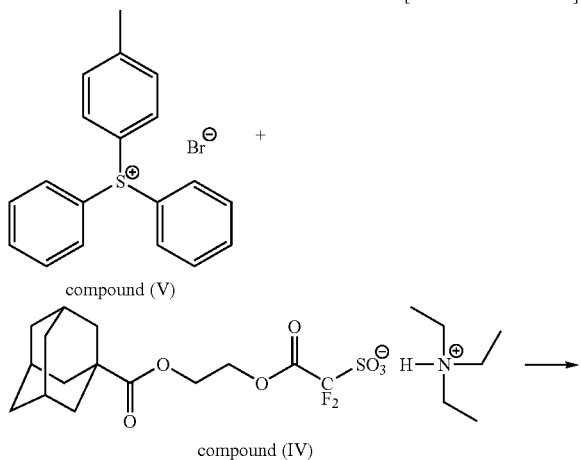

compound (V)

compound (IV)

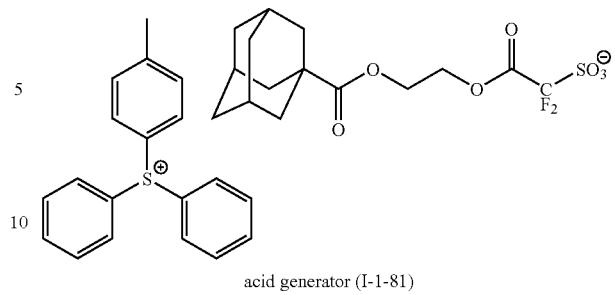

acid generator (I-1-81)

Preparation of Resist Composition

Examples 35 to 36 and Comparative Example 1

The components shown in Table 1 were mixed and dissolved to obtain positive resist compositions.

TABLE 1

| | Component (A) | Component (B) | Component (D) | Component (E) | Component (S) | |
|---|---|---|---|---|---|---|
| Example 35 | (A)-1 [100] | (B)-1 [9.14] | (D)-1 [1.2] | (E)-1 [1.32] | (S)-1 [10] | (S)-2 [2400] |
| Example 36 | (A)-2 [100] | (B)-2 [9.8] | (D)-1 [0.5] | — | (S)-1 [10] | (S)-2 [2400] |
| Comparative Example 1 | (A)-3 [100] | (B)-2 [9.8] | (D)-1 [0.5] | — | (S)-1 [10] | (S)-2 [2400] |

In Table 1, each of the abbreviations indicates the following. Also, the values within the brackets [ ] indicate blending amount (parts by weight).

(A)-1: the polymeric compound 5.

(A)-2: the polymeric compound 1.

(A)-3: a polymeric compound represented by the formula (A1-1) shown below. The weight average molecular weight (Mw) (the polystyrene equivalent value determined by gel permeation chromatography (GPC)) is 6,500, and the dispersity (Mw/Mn) is 1.97. The copolymer composition ratio (proportion (molar ratio) of each structural unit within the constitutional formula) determined by carbon 13 nuclear magnetic resonance spectrum (600 MHz_$^{13}$C-NMR) is "a21/a11/a12/a3=45.6/21.1/13.9/19.4".

[Chemical Formula 98]

(A1-1)

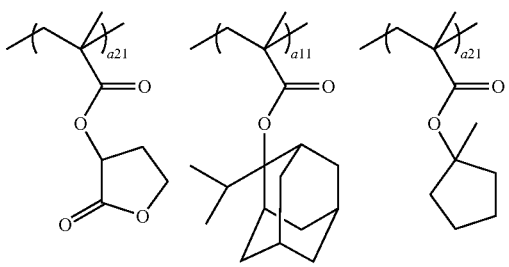

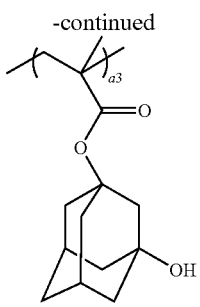

(B)-1: the acid generator (I-1-81).
(B)-2: an acid generator represented by the general formula shown below.

[Chemical Formula 99]

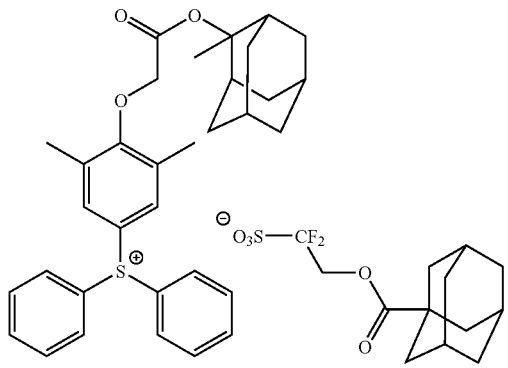

(D)-1: tri-n-pentylamine.
(E)-1: salicylic acid.
(S)-1: γ-butyrolactone.
(S-2: a mixed solvent of PGMEA/PGME=60/40 (mass ratio).

<Evaluation of Resolution>

Using each of the positive resist compositions obtained above, resist patterns for each case were formed according to the method of forming a resist pattern described below, and the resolution was evaluated.

[Resist Pattern Formation-1]

An organic anti-reflection film composition (product name: ARC29, manufactured by Brewer Science Ltd.) was applied onto an 8-inch silicon wafer using a spinner, and the composition was then baked on a hotplate at 205° C. for 60 seconds, thereby forming an organic anti-reflection film having a film thickness of 77 nm.

Then, the positive resist composition of Example 35 was applied onto the anti-reflection film using a spinner, and was then prebaked (PAB) on a hotplate at 100° C. for 60 seconds and dried, thereby forming a resist film having a film thickness of 150 nm.

Subsequently, the resist film was selectively irradiated with an ArF excimer laser (193 nm) through a mask pattern (6% half tone), using an ArF exposure apparatus NSR-302A (manufactured by Nikon Corporation; NA (numerical aperture)=0.60, ⅔ annular illumination).

A post exposure baking (PEB) treatment was then conducted at 100° C. for 60 seconds, the resist film was subjected to alkali developing for 30 seconds at 23° C. in a 2.38% by weight aqueous solution of tetramethylammonium hydroxide (TMAH) (product name: NMD-3, manufactured by Tokyo Ohka Kogyo Co., Ltd.), and was then rinsed with pure water for 30 seconds and dried by shaking.

As a result, a line and space resist pattern (hereinafter, referred to as "LS pattern") with a line width of 150 nm and a pitch of 300 nm was formed on the resist film.

In the above resist pattern formation, the optimum exposure dose "Eop" for forming the above LS pattern, namely the sensitivity, was 22 (mJ/cm²).

Furthermore, using the positive resist composition of Example 35, three kinds of patterns which target a line and space resist pattern with a line width of 250 nm and a pitch of 500 nm, an isolated pattern with a space width of 250 nm, and a large dimension pattern, respectively, were formed with the above Eop in the same manner as described above in [Resist Pattern Formation-1]. As a result, it was confirmed that all of the patterns were resolved.

[Resist Pattern Formation-2]

Each of the positive resist composition of Example 36 and Comparative Example 1 was applied, using a spinner, to the surface of an 8-inch silicon wafer that had been treated with hexamethyldisilazane (HMDS) at 90° C. for 36 seconds, and was then prebaked (PAB) on a hotplate at 90° C. for 60 seconds and dried, thereby forming a resist film having a film thickness of 200 nm.

Subsequently, the resist film was selectively irradiated with an ArF excimer laser (193 nm) through a mask pattern which targets a contact hole pattern with a hole diameter of 180 nm and a pitch of 360 nm, using an ArF exposure apparatus "NSR-302" (manufactured by Nikon; numerical aperture (NA)=0.60, σ0.75).

A post exposure baking (PEB) treatment was then conducted at 85° C. for 60 seconds, the resist film was subjected to alkali developing for 30 seconds at 23° C. in a 2.38% by weight aqueous solution of tetramethylammonium hydroxide (TMAH) (product name: NMD-3, manufactured by Tokyo Ohka Kogyo Co., Ltd.), and was then rinsed with pure water for 15 seconds and dried by shaking. Thereafter, the resist film was heated and dried at 100° C. for 60 seconds.

As a result, in each case of using the positive resist compositions of Example 36 and Comparative Example 1, a contact hole pattern was formed on the resist film.

The optimum exposure dose "Eop" for forming the above contact hole pattern, namely the sensitivity, was 32 (mJ/cm²).

Subsequently, a contact hole pattern with a hole diameter of 180 nm and a pitch of 360 nm was formed with the above Eop (32 (mJ/cm²)) in the same manner as described above in [Resist Pattern Formation-2].

The hole shapes of the contact hole pattern were observed from the upper side thereof using a scanning electron microscope (SEM) (product name: S-9220, manufactured by Hitachi, Ltd.).

As a result, it was confirmed that the resist composition of Example 36 could form a resist pattern with higher circularity and exhibit more excellent resolution, when compared with the resist composition of Comparative Example 1.

As is clear from the above descriptions, according to the present invention, there can be provided a novel polymeric compound which excels in resolution and can be used as a base component of a resist composition, a compound useful as a monomer of the polymeric compound, a resist composition including the polymeric compound, and a method of forming a resist pattern using the resist composition.

The invention claimed is:

1. A resist composition comprising a base component (A) which exhibits changed solubility in an alkali developing solution under action of an acid, and an acid generator component (B) which generates an acid upon exposure, wherein the base component (A) comprises a polymeric compound (A0) containing a structural unit (a0) represented by the general formula (a0-1) shown below:

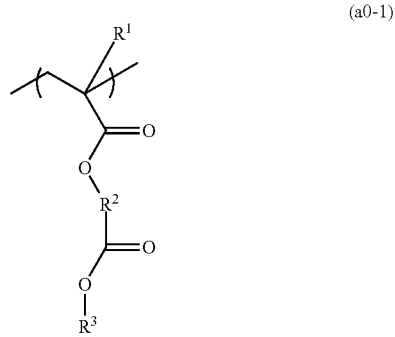
(a0-1)

(in the formula (a0-1), $R^1$ represents a hydrogen atom, a lower alkyl group of 1 to 5 carbon atoms, or a halogenated lower alkyl group of 1 to 5 carbon atoms; $R^2$ represents a bivalent linking group containing at least one kind of polar groups selected from the group consisting of —O—, —C(=O)—, —C(=O)—O—, a carbonate linkage (—O—C(=O)—O—), —S—, —S(=O)$_2$—, —S(=O)$_2$—O—, —NH—, —NR$^{04}$— (wherein, $R^{04}$ represents an alkyl group or an acyl group), and —NH—C(=O)—; and $R^3$ represents a cyclic group containing a sulfonyl group within the ring skeleton).

2. The resist composition according to claim 1, wherein $R^3$ is a cyclic group containing —O—SO$_2$— within the ring skeleton.

3. The resist composition according to claim 2, wherein said $R^3$ is a cyclic group represented by the general formula (3-1) shown below:

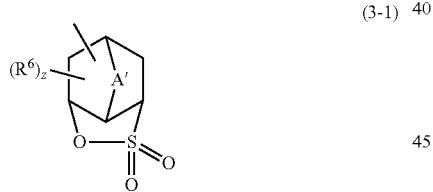
(3-1)

(in the formula (3-1), A' represents an oxygen atom, a sulfur atom, or an alkylene group of 1 to 5 carbon atoms which may contain an oxygen atom or a sulfur atom; z represents an integer of 0 to 2; $R^6$ represents an alkyl group, an alkoxy group, a halogenated alkyl group, a hydroxyl group, —COOR", —OC(=O)R", a hydroxyalkyl group or a cyano group, wherein R" represents a hydrogen atom or an alkyl group).

4. The resist composition according to claim 1, wherein the base component (A) is a base component which exhibits increased solubility in an alkali developing solution under action of an acid.

5. The resist composition according to claim 4, wherein the polymeric compound (A0) comprises the structural unit (a0) and a structural unit (a1) derived from an acrylate ester which has an acid dissociable, dissolution inhibiting group.

6. The resist composition according to claim 5, wherein the polymeric compound (A0) comprises at least two kinds of structural units as the structural unit (a1).

7. The resist composition according to claim 5, wherein the polymeric compound (A0) comprises, as the structural unit (a1), at least one kind of structural units selected from the group consisting of structural units represented by the general formulae (a1-0-11), (a1-0-12) and (a1-0-2) shown below:

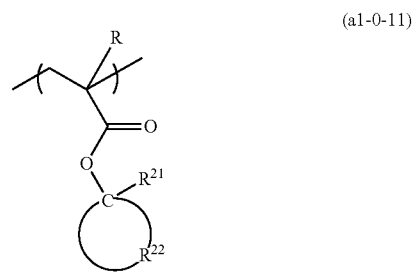
(a1-0-11)

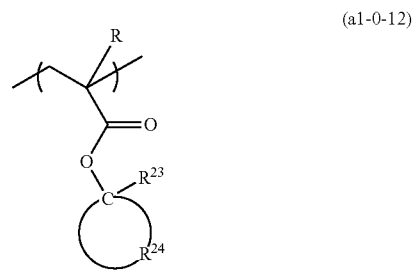
(a1-0-12)

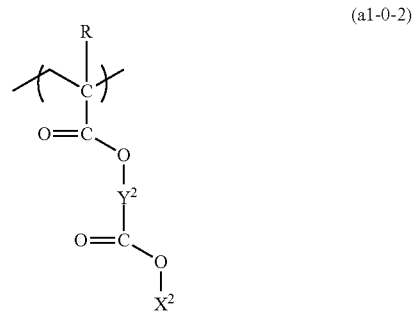
(a1-0-2)

(in the formulae, R represents a hydrogen atom, a lower alkyl group of 1 to 5 carbon atoms, or a halogenated lower alkyl group of 1 to 5 carbon atoms; $R^{21}$ represents an alkyl group; $R^{22}$ represents a group which forms an aliphatic monocyclic group together with the carbon atom to which $R^{22}$ is bonded; $R^{23}$ represents a branched alkyl group; $R^{24}$ represents a group which forms an aliphatic polycyclic group together with the carbon atom to which $R^{24}$ is bonded; $Y^2$ represents a bivalent linking group; and $X^2$ represents an acid dissociable, dissolution inhibiting group).

8. The resist composition according to claim 5, wherein the polymeric compound (A0) further comprises a structural unit (a3) derived from an acrylate ester which has a polar group-containing aliphatic hydrocarbon group.

9. The resist composition according to claim 1, further comprising a nitrogen-containing organic compound (D).

10. A method of forming a resist pattern which includes: forming a resist film on a substrate using the resist composition of claim 1; exposing the resist film; and developing the resist film with an alkali to form a resist pattern.

11. A polymeric compound comprising a structural unit (a0) represented by the structural unit (a0-1) shown below:

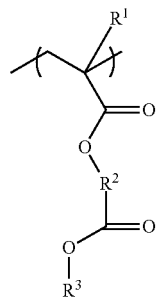
(a0-1)

(in the formula (a0-1), $R^1$ represents a hydrogen atom, a lower alkyl group of 1 to 5 carbon atoms, or a halogenated lower alkyl group of 1 to 5 carbon atoms; $R^2$ represents a bivalent linking group containing at least one kind of polar groups selected from the group consisting of —O—, —C(=O)—, —C(=O)—O—, a carbonate linkage (—O—C(=O)—O—), —S—, —S(=O)$_2$—, —S(=O)$_2$—O—, —NH—, —NR$^{04}$— (wherein, $R^{04}$ represents an alkyl group or an acyl group), and —NH—C(=O)—; and $R^3$ represents a cyclic group containing a sulfonyl group within the ring skeleton).

12. The resist composition according to claim 11, wherein $R^3$ is a cyclic group containing —O—SO$_2$— within the ring skeleton.

13. The resist composition according to claim 12, wherein $R^3$ is a cyclic group represented by the general formula (3-1) shown below:

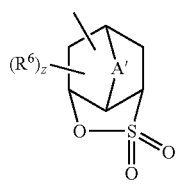
(3-1)

(in the formula (3-1), A' represents an oxygen atom, a sulfur atom, or an alkylene group of 1 to 5 carbon atoms which may contain an oxygen atom or a sulfur atom; z represents an integer of 0 to 2; $R^6$ represents an alkyl group, an alkoxy group, a halogenated alkyl group, a hydroxyl group, —COOR", —OC(=O)R", a hydroxyalkyl group or a cyano group, wherein R" represents a hydrogen atom or an alkyl group).

14. The polymeric compound according to claim 11, further comprising a structural unit (a1) derived from an acrylate ester which has an acid dissociable, dissolution inhibiting group.

15. The polymeric compound according to claim 14, wherein the polymeric compound comprises at least two kinds of structural units as the structural unit (a1).

16. The polymeric compound according to claim 14, wherein the polymeric compound comprises, as the structural unit (a1), at least one kind of structural units selected from the group consisting of structural units represented by the general formulae (a1-0-11), (a1-0-12) and (a1-0-2) shown below:

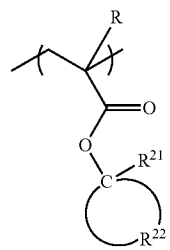
(a1-0-11)

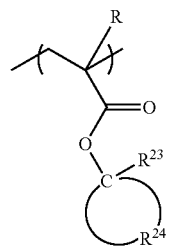
(a1-0-12)

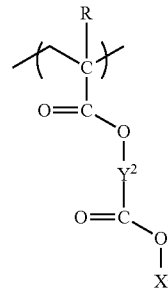
(a1-0-2)

(in the formulae, R represents a hydrogen atom, a lower alkyl group of 1 to 5 carbon atoms, or a halogenated lower alkyl group of 1 to 5 carbon atoms; $R^{21}$ represents an alkyl group; $R^{22}$ represents a group which forms an aliphatic monocyclic group together with the carbon atom to which $R^{22}$ is bonded; $R^{23}$ represents a branched alkyl group; $R^{24}$ represents a group which forms an aliphatic polycyclic group together with the carbon atom to which $R^{24}$ is bonded; $Y^2$ represents a bivalent linking group; and $X^2$ represents an acid dissociable, dissolution inhibiting group).

17. The polymeric compound according to claim 14, further comprising a structural unit (a3) derived from an acrylate ester which has a polar group-containing aliphatic hydrocarbon group.

18. A compound represented by the general formula (a0"-1) shown below:

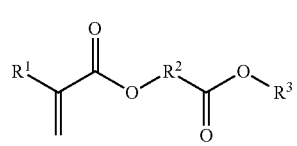
(a0"-1)

(in the formula (a0"-1), $R^1$ represents a hydrogen atom, a lower alkyl group of 1 to 5 carbon atoms, or a halogenated lower alkyl group of 1 to 5 carbon atoms; $R^2$ represents a bivalent linking group containing at least one kind of polar groups selected from the group consisting of —O—, —C(=O)—, —C(=O)—O—, a carbonate linkage (—O—C(=O)—O—), —S—, —S(=O)$_2$—, —S(=O)$_2$—O—, —NH—, —NR$^{04}$— (wherein, $R^{04}$ represents an alkyl group or an acyl group), and —NH—C(=O)—; and $R^3$ represents a cyclic group containing a sulfonyl group within the ring skeleton).

19. The resist composition according to claim 18, wherein $R^3$ is a cyclic group containing —O—SO$_2$— within the ring skeleton.

20. The resist composition according to claim 19, wherein $R^3$ is a cyclic group represented by the general formula (3-1) shown below:

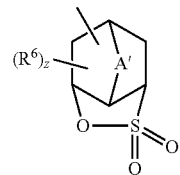

(3-1)

(in the formula (3-1), A' represents an oxygen atom, a sulfur atom, or an alkylene group of 1 to 5 carbon atoms which may contain an oxygen atom or a sulfur atom; z represents an integer of 0 to 2; $R^6$ represents an alkyl group, an alkoxy group, a halogenated alkyl group, a hydroxyl group, —COOR", —OC(=O)R", a hydroxyalkyl group or a cyano group, wherein R" represents a hydrogen atom or an alkyl group).

* * * * *

UNITED STATES PATENT AND TRADEMARK OFFICE
CERTIFICATE OF CORRECTION

| | |
|---|---|
| PATENT NO. | : 8,227,170 B2 |
| APPLICATION NO. | : 12/685579 |
| DATED | : July 24, 2012 |
| INVENTOR(S) | : Takahiro Dazai et al. |

It is certified that error appears in the above-identified patent and that said Letters Patent is hereby corrected as shown below:

In Column 4, Line 26-27, Change "—C(—O)—O—" to -- -C(=O)-,--.

In Column 4, Line 28, After "—S—," insert -- -S(=O)$_2$-,--.

In Column 4, Line 30, Change "—NH—C(—O)—;" to -- -NH-C(=O)-;--.

In Column 19, Line 60, Change "diccociable," to --dissociable,--.

In Column 80, Line 57, Change "$R^{4\prime}$" to --$R^{4\prime\prime}$--.

In Column 81, Line 47, Change "$R^{\prime\prime}$" to --$R^{1\prime\prime}$--.

In Column 81, Line 49, Change "$R^{\prime\prime}$" to --$R^{1\prime\prime}$--.

In Column 86, Line 18, Change "substitutent" to --substituent--.

In Column 88, Line 52, Change "substitutents." to --substituents.--.

In Column 88, Line 63, Change "substitutents" to --substituents--.

In Column 88, Line 66, Change "substitutent." to --substituent.--.

In Column 89, Line 21, After "-C(=O)-O-," insert -- -C(=O)-,--.

In Column 91, Line 14, Change "methansulfonate," to --methanesulfonate,--.

In Column 98, Line 66, Change "hexamethylenetetrarmine," to --hexamethylenetetramine,--.

In Column 101, Lines 54-55, Change "tetramethylammionium" to --tetramethylammonium--.

Signed and Sealed this
Twelfth Day of February, 2013

Teresa Stanek Rea
*Acting Director of the United States Patent and Trademark Office*

CERTIFICATE OF CORRECTION (continued)
U.S. Pat. No. 8,227,170 B2

In Column 104, Line 40, Change "dicyclohexylcarboxylmide" to --dicyclohexylcarboxyimide--.

In Column 104, Line 42, Change "benzoniazole" to --benzotriazole--.

In Column 108, Line 14, Change "MHz_$^3$C" to --MHz_$^{13}$C--.

In Column 154, Line 43, Change "(1V)" to --(IV)--.

In Column 155, Line 7, Change "NMR." to --NMR--.

In Column 157, Line 39, Change "(S-2:" to --(S)-2:--.